US009018409B2

(12) United States Patent
Casciato et al.

(10) Patent No.: US 9,018,409 B2
(45) Date of Patent: Apr. 28, 2015

(54) PROCESS FOR FUNCTIONALIZATION OF UNSATURATED COMPOUNDS

(75) Inventors: Stefano Casciato, Bruxelles (BE); Yannick Pouilloux, Mignaloux-Beauvoir (FR); Vincent Dubois, Ittre (BE)

(73) Assignees: Meurice R&D ASBL, Brussels (BE); Centre National de la Recherche Scientifique, Paris Cedex (FR); Université de Poitiers, Poitiers Cedex (FR)

( * ) Notice: Subject to any disclaimer, the term of this patent is extended or adjusted under 35 U.S.C. 154(b) by 0 days.

(21) Appl. No.: 13/882,128

(22) PCT Filed: Oct. 27, 2011

(86) PCT No.: PCT/EP2011/068824
§ 371 (c)(1),
(2), (4) Date: Apr. 26, 2013

(87) PCT Pub. No.: WO2012/055946
PCT Pub. Date: May 3, 2012

(65) Prior Publication Data
US 2013/0211033 A1 Aug. 15, 2013

(30) Foreign Application Priority Data

Oct. 27, 2010 (EP) .................................... 10290581

(51) Int. Cl.
C07C 69/76 (2006.01)
C07C 67/39 (2006.01)
C07C 67/26 (2006.01)
C07C 69/675 (2006.01)
C07C 69/78 (2006.01)
C08G 18/73 (2006.01)
C08G 18/36 (2006.01)
C08G 18/34 (2006.01)

(52) U.S. Cl.
CPC .............. *C07C 67/39* (2013.01); *C07C 67/26* (2013.01); *C07C 69/675* (2013.01); *C07C 69/78* (2013.01); *C07C 2101/16* (2013.01); *C07C 2101/18* (2013.01); *C08G 18/73* (2013.01); *C08G 18/36* (2013.01); *C08G 18/348* (2013.01)

(58) Field of Classification Search
CPC ...... C07C 67/26; C07C 69/675; C07C 69/75; C07C 69/78; C07C 69/28; C07C 2101/16; C07C 2101/18; C07C 67/39; C08G 18/73; C08G 18/36; C08G 18/348
See application file for complete search history.

(56) References Cited

U.S. PATENT DOCUMENTS 4,483,998 A * 11/1984 Sanderson et al. ............ 549/533
2009/0192329 A1 7/2009 Awang et al.

FOREIGN PATENT DOCUMENTS

| DE | 3642999 A1 | 6/1988 |
| DE | 10 2006 021141 A1 | 11/2007 |
| EP | 0154162 A2 | 9/1985 |
| JP | 3-007719 A | 1/1991 |
| JP | 10-001526 A | 1/1998 |
| JP | 10-114865 A | 5/1998 |
| JP | 10289436 | 10/1998 |
| WO | WO2008/079901 | * 7/2008 |
| WO | WO 2008/079901 A2 | 7/2008 |
| WO | WO2008079901 | * 7/2008 |
| WO | WO 2008/100822 | 8/2008 |
| WO | WO 2008/124294 | 10/2008 |
| WO | WO 2009/085855 | 7/2009 |
| WO | WO 2009/097041 | 8/2009 |
| WO | WO 2009/139006 | 11/2009 |

OTHER PUBLICATIONS

Punniyamurthy et al. (Cobalt(II)-Catalyzed Reaction of Enolizable Aldehydes with Alkenes in the Presence of Dioxygen: The Role of Acyl Radical, J. Org. Chern. 59, 850-853, 1994).*
International Search Report for International Application No. PCT/EP2011/068824, mailed on Apr. 3, 2012.
Butterworth et al., "Environmentally friendly catalysis using supported reagents: catalytic epoxidation using a chemically modified silica gel," Chem. Commun., pp. 1859-1860 (1996).
Kakuchi et al., "Chirality Induction in Cyclocopolymerization. 14. Template Effect of 1,2-Cycloalkanediol in the Cyclocopolymerization of Bis(4-vinylbenzoate)s with Styrene," Macromolecules, vol. 34(1), pp. 38-43 (Jan. 1, 2001).
Kockritz et al., "Epoxidation of methyl oleate with molecular oxygen in the presence of aldehydes," Eur. J. Lipid Sci. Technol., vol. 110, pp. 581-586 (2008).
Letellier et al., "Recombination Products From the Radiolysis of Tricaproin," J. Am. Oil. Chem. Soc., vol. 49, pp. 259-263 (Apr. 1972).
Mastrorilli et al., "Aerobic Oxidations of Unsaturated Substrates under Mukuyama's Conditions: the Role of the Metal and of the Sacrificial Aldehyde," Tetrahedron, vol. 51(29), pp. 7943-7950 (1995).
B.R. Moser, et al. J Amer. Oil Chem. Soc., 84: 675-680 (2007).
J. Salimon, et al. Asian Journal of Chemistry; 22(7): 5468-5476 (2010).
Duan, et al., "Synthesis and Characterization of Chemically Modified Soybean Oil, Journal of Tsinghua University Science and Technology," 49(9): 1549-1552 (2009).
Harada et al., "A CD Method for Determination of the Absolute Stereochemistry of Acyclic Glycols. 2. Application of the CD Exciton Chirality Method to Acyclic 1,2-Dibenzoates Systems," Enantiomer, 1(2): 119-138 (1996).
Birosel D., et al., "9, 10-Dihydroxystearic Acid of Naturally Occurring Fatty Acids of Twenty Different Fats and Oil," Philippine Journal of Science 95(2):159-169 (1967).
Kobayashi, et al., "The Absolute Stereostructures of the Polyacetylenic Constituents of Ginseng Radix Rubra," Tetrahedron, 53(46):15961-15700 (1997).

* cited by examiner

Primary Examiner — Brandon Fetterolf
Assistant Examiner — Blaine G Doletski
(74) Attorney, Agent, or Firm — Knobbe Martens Olson & Bear LLP

(57) ABSTRACT

The present invention relates to a process for synthesizing a multifunctional compound, including the reaction of a compound of formula (II) with atmospheric or molecular oxygen, in the presence of at least one aldehyde of formula (III), and optionally in the presence of at least one catalyst or at least one radical initiator; wherein: $R^{10}$, $R^{20}$, $R^{30}$, $R^{40}$, $R^{50}$, $L^2$, $R^{60}$, $R^7$, $R^8$, and $R^9$ are as described in the claims. The invention also relates to the use of these compounds as monomers for the preparation of polyurethane. The invention also relates to the use of these compounds as monomers of polymers or of biopolymers.

10 Claims, 3 Drawing Sheets

PROCESS FOR FUNCTIONALIZATION OF UNSATURATED COMPOUNDS

CROSS-REFERENCE TO RELATED APPLICATIONS

This application is the U.S. National Phase under 35 U.S.C. §371 of International Application PCT/EP2011/068824, filed Oct. 27, 2011, which was published in a non-English language, which claims priority to EP 10290581.7, filed Oct. 27, 2010.

FIELD OF THE INVENTION

The invention relates to a method for synthesizing functionalized compounds, starting from unsaturated molecules. The invention also relates to the use of these compounds as surfactants, plasticizers, lubricants, monomers of polymers or monomers of biopolymers, etc.

DESCRIPTION OF THE PRIOR ART

The synthesis of compounds from unsaturated molecules may be carried out in several ways. For example, it may be carried out in two steps through an epoxidation route. The first step includes an epoxidation reaction by oxygenated water in the presence of a carboxylic acid in order to form a peracid in situ that comprises the epoxidation agent. On an industrial scale, acetic acid is used in the presence of a mineral acid ($H_2SO_4$) that is necessary in order to catalyze the formation of the peracid. The second step includes the reaction opening of the oxirane cycle using a cleaving agent in the presence of a homogenous acid-base catalytic system.

The homogenous catalysts frequently used in the case of an opening of fatty epoxides are hydrochloric acid, sulfuric acid, phosphoric acid, fluoroboric acid or p-toluenesulfonic acid. Regarding the first step, the peracid is the primary cause of secondary reactions of opening the oxirane cycle during the industrial process, which causes a selectivity of fatty epoxides which rarely exceeds 80%. In addition, the mineral acid in an oxidizing environment causes serious corrosion issues, which may have consequences on use, storage and transport. Regarding the second step, the homogenous catalysts used must be neutralized, which necessitates additional steps that very often produce waste. These technologies involve many secondary reactions that unquestionably have a negative impact on the selectivity of the reaction.

The purpose of the present invention is to remedy at least one of the difficulties cited above.

SUMMARY OF THE INVENTION

The present invention relates to a process for synthesizing compounds of formula (Ia) or (Ib), a stereoisomer, a mixture thereof, an oligomer and/or a polymer thereof:

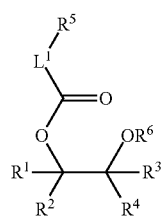

(Ia)

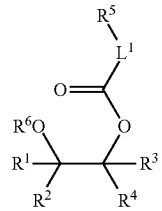

(Ib)

comprising the reaction of a compound having formula (II) with atmospheric or molecular oxygen, in the presence of at least one aldehyde of formula (III) and optionally in the presence of at least one catalyst or at least one radical initiator;

(II)

(III)

wherein:

$R^1$ is H or is selected from the group comprising $C_1$-$C_{20}$ alkyl, $C_2$-$C_{20}$ alkenyl, and $C_6$-$C_{12}$ aryl, with each group being optionally substituted by one or several groups, either identical or different, selected from the group comprising a halogen atom, —OH, —CHO, oxo, cyano, —$NR^9_2$, epoxy, $C_1$-$C_4$ alkoxy, $C_1$-$C_6$ alkyl, $C_6$-$C_{12}$ aryl, —$OCOL^1R^5$, —$OCOR^8$, and —$CO_2R^{60}$;

$R^2$ is H, cyano or a halogen atom, or is selected from the group comprising $C_1$-$C_{20}$ alkyl, $C_2$-$C_{20}$ alkenyl, $C_6$-$C_{12}$ aryl, and $C_6$-$C_{12}$ aryl$C_{1-6}$ alkyl, with each group being optionally substituted by one or several groups, either identical or different, selected from the group comprising a halogen atom, —OH, —CHO, oxo, cyano, —$NR^9_2$, epoxy, $C_1$-$C_4$ alkoxy, $C_1$-$C_6$ alkyl, $C_6$-$C_{12}$ aryl, —$OCOL^1R^5$, —$OCOR^8$, and —$CO_2R^{60}$;

$R^3$ is selected from the group comprising epoxy, —$OCOR^8$, —$CO_2R^8$, $C_1$-$C_{20}$ alkyl, $C_2$-$C_{20}$ alkenyl, $C_6$-$C_{12}$ aryl, and $C_6$-$C_{12}$aryl$C_{1-6}$ alkyl, with each group being optionally substituted by one or several groups, either identical or different, selected from the group comprising a halogen atom, —OH, —CHO, oxo, cyano, —$NR^9_2$, epoxy, $C_1$-$C_4$ alkoxy, $C_1$-$C_6$ alkyl, $C_6$-$C_{12}$ aryl, —$OCOL^1R^5$, —$OCOR^8$, and —$CO_2R^{60}$;

$R^4$ is H, cyano, a halogen atom, or is selected from the group comprising $C_1$-$C_{20}$ alkyl, $C_2$-$C_{20}$ alkenyl, and $C_6$-$C_{12}$ aryl, with each group being optionally substituted by one or several groups, either identical or different, selected from the group comprising a halogen atom, —OH, —CHO, oxo, cyano, —$NR^9_2$, epoxy, $C_1$-$C_4$ alkoxy, $C_1$-$C_6$ alkyl, $C_6$-$C_{12}$ aryl, —$OCOL^1R^5$, —$OCOR^8$, and —$CO_2R^{60}$;

or $R^1$ and $R^3$ may, with the carbons to which they are bound, form a group selected from a $C_5$-$C_{12}$ cycloalkyl and a $C_5$-$C_{12}$ cycloalkenyl, with each group being optionally substituted by one or several groups, either identical or different, selected from the group comprising a halogen atom, —OH, oxo, cyano, epoxy, —OCOL$^1$R$^5$, —OCOR$^8$, —CO$_2$R$^{60}$, C$_1$-C$_6$ alkyl, C$_1$-C$_6$ hydroxyalkyl, and C$_2$-C$_6$ alkenyl;

R$^5$ is selected from the group comprising H, a halogen atom, —OH, —CHO, epoxy, —SR$^8$, cyano, nitro, isocyanate, C$_1$-C$_{20}$ alkyl, C$_1$-C$_4$ alkoxy, C$_2$-C$_{20}$ alkenyl, C$_2$-C$_{20}$ alkynyl, heterocycloalkyl, —CO$_2$R$^8$, and —NR$^9$$_2$;

R$^6$ is H or —CO-L$^1$-R$^5$;

L$^1$ is a single covalent bond, or is selected from the group comprising C$_1$-C$_{20}$ alkylene, C$_3$-C$_{12}$ cycloalkylene, C$_2$-C$_{12}$ alkenylene, C$_5$-C$_{12}$cycloalkenylene, C$_6$-C$_{12}$ arylene, heteroarylene, and heterocycloalkylene, with each group being optionally substituted by one or several groups, either identical or different either identical or different, selected from the group comprising a halogen atom, —OH, oxo, nitro, —CHO, —OCOL$^1$R$^5$, —CO$_2$R$^{60}$, —NR$^9$$_2$, C$_1$-C$_6$ alkyl, C$_1$-C$_4$ alkoxy, C$_6$-C$_{12}$ aryl, C$_6$-C$_{12}$ aryloxy, C$_6$-C$_{12}$arylC$_{1-6}$ alkyl, C$_1$-C$_6$ hydroxyalkyl, and C$_{1-6}$ alkylC$_6$-C$_{12}$ aryl;

R$^{10}$ is H, or is selected from the group comprising C$_1$-C$_{20}$ alkyl, C$_2$-C$_{20}$ alkenyl, and C$_6$-C$_{12}$ aryl, with each group being optionally substituted by one or several groups, either identical or different either identical or different, selected from the group comprising a halogen atom, —OH, —CHO, oxo, cyano, —NR$^9$$_2$, epoxy, C$_1$-C$_4$ alkoxy, —OCOL$^2$R$^{50}$, C$_1$-C$_6$ alkyl, C$_6$-C$_{12}$ aryl, —OCOR$^8$, and —CO$_2$R$^{60}$;

R$^{20}$ is H, cyano, a halogen atom, or —CHO, or is selected from the group comprising C$_1$-C$_{20}$ alkyl, C$_2$-C$_{20}$ alkenyl, C$_6$-C$_{12}$ aryl, and C$_6$-C$_{12}$ arylC$_{1-6}$ alkyl, with each group being optionally substituted by one or several groups, either identical or different, selected from the group comprising a halogen atom, —OH, —CHO, oxo, cyano, —NR$^9$$_2$, epoxy, C$_1$-C$_4$ alkoxy, —OCOL$^2$R$^{50}$, C$_1$-C$_6$ alkyl, C$_6$-C$_{12}$ aryl, —OCOR$^8$, and —CO$_2$R$^{60}$, R$^{30}$ is selected from the group comprising epoxy, —OCOR$^8$, —CO$_2$R$^8$, C$_1$-C$_{20}$ alkyl, C$_2$-C$_{20}$ alkenyl, C$_6$-C$_{12}$ aryl, and C$_6$-C$_{12}$ arylC$_{1-6}$alkyl, with each group being optionally substituted by one or several groups, either identical or different, selected from the group comprising a halogen atom, —OH, —CHO, oxo, cyano, —NR$^9$$_2$, epoxy, C$_1$-C$_4$ alkoxy, —OCOL$^2$R$^{50}$, C$_1$-C$_6$ alkyl, C$_6$-C$_{12}$ aryl, —OCOR$^8$, and —CO$_2$R$^{60}$, R$^{40}$ is H, cyano, a halogen atom, or —CHO, or is selected from the group comprising C$_1$-C$_{20}$ alkyl, C$_2$-C$_{20}$ alkenyl, and C$_6$-C$_{12}$ aryl, with each group being optionally substituted by one or several groups, either identical or different, selected from the group comprising a halogen atom, —OH, —CHO, oxo, cyano, —NR$^9$$_2$, epoxy, C$_1$-C$_4$ alkoxy, —OCOL$^2$R$^{50}$, C$_1$-C$_6$ alkyl, C$_6$-C$_{12}$ aryl, —OCOR$^8$, and —CO$_2$R$^{60}$;

or R$^{10}$ and R$^{30}$ may, with the carbons to which they are bound, form a group selected from a C$_5$-C$_{12}$ cycloalkyl or a C$_5$-C$_{12}$ cycloalkenyl, with each group being optionally substituted by one or several groups, either identical or different, selected from the group comprising a halogen atom, —OH, —CHO, cyano, oxo, epoxy, —OCOR$^8$, —CO$_2$R$^{60}$, —OCOL$^2$R$^{50}$, C$_1$-C$_6$ alkyl, C$_1$-C$_6$ hydroxyalkyl, and C$_2$-C$_6$ alkenyl;

R$^{50}$ is selected from the group comprising H, —CHO, epoxy, a halogen atom, —OH, cyano, nitro, isocyanate, C$_1$-C$_{20}$ alkyl, C$_1$-C$_4$ alkoxy, C$_2$-C$_{20}$ alkenyl, C$_2$-C$_{20}$ alkynyl, heterocycloalkyl, —CO$_2$R$^8$, and —NR$^9$$_2$;

L$^2$ is a single covalent bond, or is selected from the group comprising C$_1$-C$_{20}$ alkylene, C$_3$-C$_{12}$ cycloalkylene, C$_2$-C$_{12}$ alkenylene, C$_5$-C$_{12}$ cycloalkenylene, C$_6$-C$_{12}$ arylene, heteroarylene, and heterocycloalkylene, with each group being optionally substituted by one or several groups, either identical or different, selected from the group comprising a halogen atom, oxo, nitro, —CHO, —OH, —NR$^9$$_2$, C$_1$-C$_6$ alkyl, C$_1$-C$_4$ alkoxy, C$_6$-C$_{12}$ arylC$_{1-6}$ alkyl, C$_{1-6}$ alkylC$_6$-C$_{12}$ aryl, C$_6$-C$_{12}$ aryloxy, C$_1$-C$_6$ hydroxyalkyl, and C$_6$-C$_{12}$ aryl;

R$^{60}$ is selected from the groups comprising H or C$_1$-C$_6$ alkyl optionally substituted by one or several groups, either identical or different, selected from the group comprising —OH, —CHO, —O—COR$^7$, and C$_1$-C$_6$ alkyl;

R$^7$ is selected from the group comprising C$_1$-C$_{24}$ alkyl, C$_2$-C$_{20}$ alkenyl, and C$_6$-C$_{12}$ aryl, with each group being optionally substituted by one or several groups, either identical or different, selected from the group comprising —OH, epoxy and —OCOL$^1$R$^5$;

R$^8$ is selected from among H or C$_1$-C$_6$ alkyl; and R$^9$ is selected from H, C$_1$-C$_6$ alkyl, or C$_6$-C$_{12}$ aryl.

The process according to the present invention draws its innovation, in relation to current processes, from the reduction of the steps of synthesis as well as from the envisaged synthesis method. The chemical reactions involved in the process according to the invention use oxygen as the transformation agent, which avoids on the one hand the risks related to the storage and transport of oxygenated water (traditionally used for the fabrication of epoxides) and on the other hand considerably reduces production cost, since oxygen may be taken from ambient air (atmospheric oxygen). According to a preferred embodiment, to be conducted under these conditions, the synthesis requires the presence of a mineral solid (catalyst). According to a preferred embodiment, the catalyst plays an essential role since on the one hand it accelerates the chemical reactions, it decreases their energy demand, and on the other hand it considerably simplifies the fabrication process. This process allows "cleaner" synthesis thus reducing fabrication costs. The multifunctional compounds produced by the reaction, also called "monomers," may also react with each other during the reaction to produce "dimers" which in turn may react with the various monomers to produce very varied oligomers (trimers, quadrimers, etc.), and polymers.

The invention therefore proposes an original, economical and ecological process for the production of multifunctional compounds, the latter may be the basis for the production of very diverse products, and in particular plastic material or lubricants, etc. The synthesized molecules are particularly beneficial as synthons for the fabrication of plastic material. Advantageously, the synthesized molecules may themselves even be oligomers or polymers. Various types of polymers may be envisaged depending on the nature of the function provided by the synthesis process. When the unsaturated and/or aldehydic compound used in the process is derived from the plant world (fatty acid esters), the plastic materials or polymers manufactured downstream from the synthesis process will therefore be produced from the start from a renewable raw material, and therefore they are qualified as biopolymers or even "bio-based polymers."

The present invention also relates to a compound of formula (Ie) or (If), a stereoisomer thereof, or a mixture thereof;

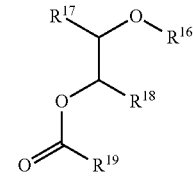

(Ie)

-continued

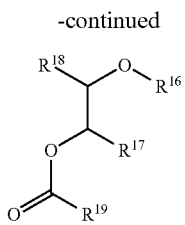

(If)

wherein:

$R^{16}$ is H or is selected from the group comprising —CO—$(CR^{21}R^{22})_q$—$R^{23}$, —CO—$C_6$-$C_{12}$aryl and —CO—$C_5$-$C_{12}$cycloalkenyl, with each group being optionally substituted by one or several groups, either identical or different, selected from the group comprising a halogen atom, —OH, —OCOR$^{19}$, —CO$_2$R$^{24}$, and $C_1$-$C_6$ alkyl;

$R^{17}$ is selected from the group comprising a $C_2$-$C_{20}$ alkyl and a $C_2$-$C_{20}$ alkenyl, with each group being optionally substituted by one or several groups, either identical or different, selected from the group comprising a $C_1$-$C_6$ alkyl, a $C_6$ aryl, —OR$^{16}$ and —CO$_2$R$^{24}$;

$R^{18}$ is H or is selected from the group comprising a $C_2$-$C_{20}$ alkyl and a $C_2$-$C_{20}$ alkenyl, with each group being optionally substituted by one or several groups, either identical or different, selected from the group comprising a $C_1$-$C_6$ alkyl, a $C_6$ aryl, —OR$^{16}$ and CO$_2$R$^{24}$;

or $R^{17}$ and $R^{18}$ may, with the carbons to which they are bound, form a group selected from a $C_5$-$C_{12}$ cycloalkyl or a $C_5$-$C_{12}$ cycloalkenyl, with each group being optionally substituted by one or several groups, either identical or different, selected from the group comprising a halogen atom, —OR$^{16}$, —OCOR$^{19}$, —CO$_2$R$^{24}$, and a $C_1$-$C_6$ alkyl;

$R^{19}$ is selected from the group comprising —(CR$^{21}$R$^{22}$)$_q$— R$^{23}$, a $C_6$-$C_{12}$ aryl, and a $C_5$-$C_{12}$ cycloalkenyl, with each group being optionally substituted by one or several groups, either identical or different, selected from the group comprising a halogen atom, —OH, —OCOR$^{19}$, —CO$_2$R$^{24}$, and $C_1$-$C_6$ alkyl;

q is a whole number comprised between 3 and 12;

each identical or different R$^{21}$ is selected from H or a $C_1$-$C_6$ alkyl;

each identical or different R$^{22}$ is selected from H or a $C_1$-$C_6$ alkyl;

$R^{23}$ is H or —OH, or is selected from the group comprising $C_1$-$C_6$ alkyl and a $C_6$-$C_{12}$ aryl, with each group being optionally substituted by one or several groups, either identical or different, selected from the group comprising a halogen atom, —OH, —OCOR$^{19}$, —CO$_2$R$^{24}$, and $C_1$-$C_6$ alkyl;

$R^{24}$ is H or a $C_1$-$C_6$ alkyl optionally substituted by one or several groups, either identical or different, selected from the group comprising —OH, —O—COR$^{25}$, and $C_1$-$C_6$ alkyl; and $R^{25}$ is selected from the group comprising $C_2$-$C_{20}$ alkyl, and $C_2$-$C_{20}$ alkenyl, with each group being optionally substituted by one or several groups, either identical or different, selected from the group comprising —OH, epoxy, —OR$^{16}$, and —OCOR$^{19}$.

According to a preferred embodiment, the present invention also relates to a compound having formula (Ie) or (If), a stereoisomer thereof, or a mixture thereof; provided that the compound is not methyl 9-(hexanoyloxy)-10-hydroxyoctadecanoate, methyl 10-(hexanoyloxy)-9-hydroxyoctadecanoate, the octanoic ester of methyl hydroxyoleate, the 2-ethyl-hexyl ester of methyl hydroxyoleate, methyl hydroxybenzoyloxy-octadodecanoate, 1,2-heptanediol dicaproate or 1,2-octanediol dicaproate.

The present invention also concerns the use of compounds according to the invention, in the preparation of polymers, of biopolymers, of surfactants, plasticizers, lubricants and biocides. Preferably, the invention concerns the use of the compounds according to the invention, in the preparation of polymers or biopolymers. This invention also concerns the use of a compound according to the invention, as a monomer for the preparation of polyurethane.

Other aspects, distinctive aspects and advantages of the present invention will be gleaned from reading the description that follows and the illustrative examples provided simply by way of illustration, and which are not intended in any way to limit the scope of the invention.

DETAILED DESCRIPTION OF THE INVENTION

Figure 1:
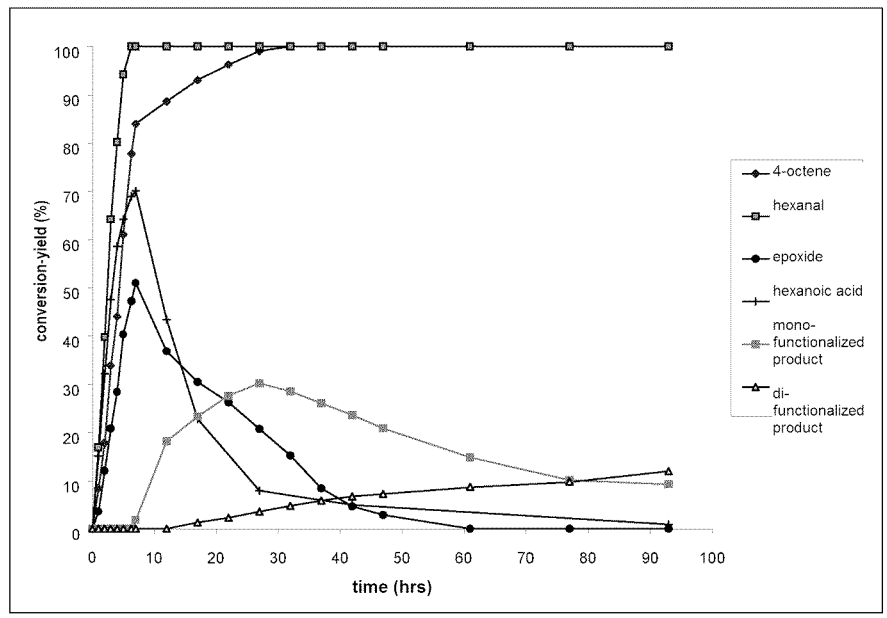
FIG. 1 presents a graph showing the kinetic reagent conversion curves and yield of products in the case of the reaction of hexanal with 4-octene in Example 3.

According to a first aspect, the present invention concerns a process for synthesizing multifunctional compounds: comprising the reaction of a compound of formula (II) with atmospheric or molecular oxygen, in the presence of at least one aldehyde of formula (III), and optionally in the presence of at least one catalyst or at least one radical initiator;

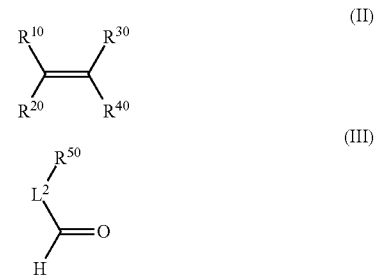

wherein:

$R^{10}$ is H, or is selected from the group comprising $C_1$-$C_{20}$ alkyl, $C_2$-$C_{20}$ alkenyl, and $C_6$-$C_{12}$ aryl, with each group being optionally substituted by one or several groups, either identical or different, selected from the group comprising a halogen atom, —OH, —CHO, oxo, cyano, —NR$^9{}_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CO$_2$R$^{60}$;

$R^{20}$ is H, cyano, a halogen atom, or —CHO, or is selected from the group comprising $C_1$-$C_{20}$ alkyl, $C_2$-$C_{20}$ alkenyl, $C_6$-$C_{12}$ aryl, and $C_6$-$C_{12}$ aryl$C_{1-6}$alkyl, with each group being optionally substituted by one or several groups, either identical or different, selected from the group comprising a halogen atom, —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CO$_2$R$^{60}$;

R$^{30}$ is selected from the group comprising epoxy, —OCOR$^8$, —CO$_2$R$^8$, $C_1$-$C_{20}$ alkyl, $C_2$-$C_{20}$ alkenyl, $C_6$-$C_{12}$ aryl, and $C_6$-$C_{12}$aryl$C_{1-6}$ alkyl, with each group being optionally substituted by one or several groups, either identical or different, selected from the group comprising a halogen atom, —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CO$_2$R$^{60}$;

R$^{40}$ is H, cyano, a halogen atom, or —CHO, or is selected from the group comprising $C_1$-$C_{20}$ alkyl, $C_2$-$C_{20}$ alkenyl, and $C_6$-$C_{12}$ aryl, with each group being optionally substituted by one or several groups, either identical or different, selected from the group comprising a halogen atom, —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CO$_2$R$^{60}$;

or R$^{10}$ and R$^{30}$ may, with the carbons to which they are bound, form a group selected from a $C_5$-$C_{12}$ cycloalkyl or a $C_5$-$C_{12}$ cycloalkenyl, with each group being optionally substituted by one or several groups, either identical or different, selected from the group comprising a halogen atom, —OH, —CHO, cyano, oxo, epoxy, —OCOR$^8$, —CO$_2$R$^{60}$, —OCOL$^2$R$^{50}$, $C_1$-$C_6$ alkyl, $C_1$-$C_6$ hydroxyalkyl, and $C_2$-$C_6$ alkenyl R$^{50}$ is selected from the group comprising H, —CHO, epoxy, a halogen atom, —OH, —SR$^8$, cyano, nitro, isocyanate, $C_1$-$C_{20}$ alkyl, $C_1$-$C_4$ alkoxy, $C_2$-$C_{20}$ alkenyl, $C_2$-$C_{20}$ alkynyl, heterocycloalkyl, —CO$_2$R$^8$, and —NR$^9_2$;

L$^2$ is a single covalent bond, or is selected from the group comprising $C_1$-$C_{20}$ alkylene, $C_3$-$C_{12}$ cycloalkylene, $C_2$-$C_{12}$ alkenylene, $C_5$-$C_{12}$ cycloalkenylene, $C_6$-$C_{12}$ arylene, heteroarylene, and heterocycloalkylene, with each group being optionally substituted by one or several groups, either identical or different, selected from the group comprising a halogen atom, oxo, nitro, —CHO, —OH, —NR$^9_2$, $C_1$-$C_6$ alkyl, $C_1$-$C_4$ alkoxy, $C_6$-$C_{12}$ aryl$C_{1-6}$alkyl, $C_6$-$C_{12}$ aryloxy, $C_{1-6}$ alkyl$C_6$-$C_{12}$ aryl, $C_1$-$C_6$ hydroxyalkyl, and $C_6$-$C_{12}$ aryl;

R$^{60}$ is selected from the group comprising H and $C_1$-$C_6$ alkyl optionally substituted by one or several groups, either identical or different, selected from the group comprising —OH, —CHO, —O—COR$^7$, and $C_1$-$C_6$ alkyl;

R$^7$ is selected from the group comprising $C_1$-$C_{24}$ alkyl, $C_2$-$C_{20}$ alkenyl, and $C_6$-$C_{12}$ aryl, with each group being optionally substituted by one or several groups, either identical or different, selected from the group comprising —OH, epoxy and —OCOL$^1$R$^5$;

R$^8$ is selected from H or $C_1$-$C_6$ alkyl; and each identical or different R$^9$ is selected from H, $C_1$-$C_6$ alkyl, or $C_6$-$C_{12}$ aryl.

Preferably, the present invention concerns a process for synthesis according to the first aspect in which the multifunctional compound or compounds are a compound of formula (Ia) of (Ib), a stereoisomer, a mixture of compounds of this family, and/or an oligomer and/or a polymer thereof.

The present invention preferably concerns a process for the synthesis of compounds of the family represented by formula (Ia) or (Ib), a stereoisomer, a mixture of compounds of this family, and/or an oligomer and/or a polymer thereof, such as the compounds of formula (Ic) or (Id),

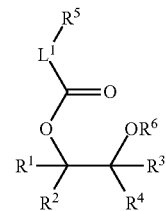

(Ia)

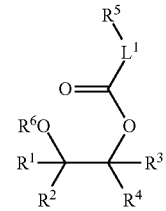

(Ib)

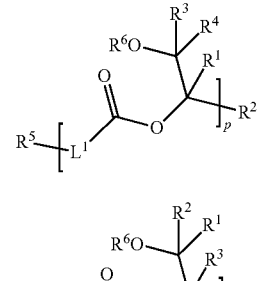

(Ic)

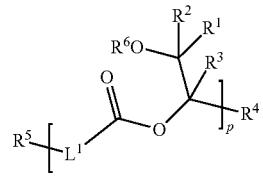

(Id)

comprising the reaction of an unsaturated molecule of formula (II) with atmospheric or molecular oxygen, in the presence of at least one aldehyde of formula (III) and optionally in the presence of at least one catalyst or at least one radical initiator; wherein:

p is a whole number comprised between 1 and 10,000, preferably p is a whole number comprised between 1 and 1,000, for example p is a whole number comprised between 1 and 100;

R$^1$ is H or is selected from the group comprising $C_1$-$C_{20}$ alkyl, $C_2$-$C_{20}$ alkenyl, and $C_6$-$C_{12}$ aryl, each group being optionally substituted by one or several groups (for example 1, 2, 3, or 4), either identical or different, selected from the group comprising a halogen atom, —OH, —CHO, oxo, cyano, —NR$^9_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$; preferably R$^1$ is H or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, cyano, —NR$^9_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$; preferably R$^1$ is H or is selected from the group comprising $C_1$-$C_{20}$ alkyl, and $C_2$-$C_{20}$ alkenyl, with each group being optionally substituted by 1, 2 or 3 groups, either identical or different, selected from the group comprising —OH, oxo, $C_1$-$C_2$ alkoxy, $C_1$-$C_6$ alkyl, —OCOL$^1$R$^5$, and —CO$_2$R$^{60}$; preferably R$^1$ is H or is selected from the group comprising $C_1$-$C_{12}$ alkyl, and $C_2$-$C_{12}$ alkenyl, with each group being optionally substituted by 1, 2 or 3 groups, either identical or different, selected from the group comprising —OH, $C_1$-$C_6$ alkyl, —OCOL$^1$R$^5$, and —CO$_2$R$^{60}$;

$R^2$ is H, cyano, or a halogen atom, or is selected from the group comprising $C_1$-$C_{20}$ alkyl, $C_2$-$C_{20}$ alkenyl, $C_6$-$C_{12}$ aryl, and $C_6$-$C_{12}$ aryl$C_{1-6}$alkyl, each group being optionally substituted by one or several groups (for example 1, 2, 3, or 4), either identical or different, selected from the group comprising a halogen atom, —OH, —CHO, oxo, cyano, —NR$^9{}_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$; preferably $R^2$ is H or is selected from the group comprising $C_1$-$C_{20}$ alkyl, $C_2$-$C_{20}$ alkenyl, $C_6$-$C_{12}$ aryl, and $C_6$-$C_{12}$ aryl$C_{1-6}$ alkyl, with each group being optionally substituted by 1, 2 or 3 groups, either identical or different, selected from the group comprising —OH, —CHO, epoxy, oxo, cyano, —NR$^9{}_2$, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$; preferably $R^2$ is H or is selected from the group comprising $C_1$-$C_{20}$ alkyl, and $C_2$-$C_{20}$ alkenyl, with each group being optionally substituted by 1, 2 or 3 groups, either identical or different, selected from the group comprising oxo, $C_1$-$C_2$ alkoxy, $C_1$-$C_6$ alkyl, —OCOL$^1$R$^5$, and —CO$_2$R$^{60}$; preferably $R^2$ is H or is selected from the group comprising $C_1$-$C_{12}$ alkyl, and $C_2$-$C_{12}$ alkenyl, with each group being optionally substituted by 1, 2 or 3 groups, either identical or different, selected from $C_1$-$C_6$ alkyl, —OCOL$^1$R$^5$, or —CO$_2$R$^{60}$; preferably $R^2$ is H or a $C_1$-$C_{12}$ alkyl, optionally substituted by 1, 2 or 3 groups, either identical or different, selected from $C_1$-$C_6$ alkyl, —OCOL$^1$R$^5$, or —CO$_2$R$^{60}$, preferably $R^2$ is H;

$R^3$ is selected from the group comprising epoxy, —OCOR$^8$, —CO$_2$R$^8$, $C_1$-$C_{20}$ alkyl, $C_2$-$C_{20}$ alkenyl, $C_6$-$C_{12}$ aryl, and $C_6$-$C_{12}$ aryl$C_{1-6}$ alkyl, each group being optionally substituted by one or several groups (for example 1, 2, 3, or 4), either identical or different, selected from the group comprising a halogen atom, —OH, —CHO, oxo, cyano, —NR$^9{}_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$; preferably $R^3$ is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, epoxy, $C_1$-$C_4$ alkoxy, $C_1$-$C_6$ alkyl, $C_6$-$C_{12}$ aryl, —OCOL$^1$R$^5$ and —CO$_2$R$^{60}$; preferably $R^3$ is selected from the group comprising $C_1$-$C_{20}$ alkyl, and $C_2$-$C_{20}$ alkenyl, with each group being optionally substituted by 1, 2 or 3 groups, either identical or different, selected from the group comprising —OH, oxo, $C_1$-$C_2$ alkoxy, $C_1$-$C_6$ alkyl, —OCOL$^1$R$^5$ and —CO$_2$R$^{60}$; preferably $R^3$ is selected from the group comprising $C_1$-$C_{12}$ alkyl, and $C_2$-$C_{12}$ alkenyl, with each group being optionally substituted by 1, 2 or 3 groups, either identical or different, selected from —OH, $C_1$-$C_6$ alkyl, —OCOL$^1$R$^5$, or —CO$_2$R$^{60}$;

$R^4$ is H, cyano, or a halogen atom, or is selected from the group comprising $C_1$-$C_{20}$ alkyl, $C_2$-$C_{20}$ alkenyl, and $C_6$-$C_{12}$ aryl, each group being optionally substituted by one or several groups (for example 1, 2, 3, or 4), either identical or different, selected from the group comprising a halogen atom, —OH, —CHO, oxo, cyano, —NR$^9{}_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$; preferably $R^4$ is H, or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, epoxy, $C_1$-$C_4$ alkoxy, $C_1$-$C_6$ alkyl, $C_6$-$C_{12}$ aryl, —OCOL$^1$R$^5$, and —CO$_2$R$^{60}$; preferably $R^4$ is H, or is selected from the group comprising $C_1$-$C_{20}$ alkyl, and $C_2$-$C_{20}$ alkenyl, with each group being optionally substituted by 1, 2 or 3 groups, either identical or different, selected from the group comprising oxo, $C_1$-$C_2$ alkoxy, $C_1$-$C_6$ alkyl, —OCOL$^1$R$^5$, and —CO$_2$R$^{60}$; preferably $R^4$ is H, or is selected from the group comprising $C_1$-$C_{12}$ alkyl, and $C_2$-$C_{12}$ alkenyl, with each group being optionally substituted by 1, 2 or 3 groups, either identical or different, selected from $C_1$-$C_6$ alkyl, —OCOL$^1$R$^5$, or —CO$_2$R$^{60}$; preferably $R^4$ is H or $C_1$-$C_{12}$ alkyl, optionally substituted by 1, 2 or 3 groups, either identical or different, selected from $C_1$-$C_6$ alkyl, —OCOL$^1$R$^5$, or —CO$_2$R$^{60}$; preferably $R^4$ is H; or else $R^1$ and $R^3$ may, with the carbons to which they are bound, form a group selected from a $C_5$-$C_{12}$ cycloalkyl or a $C_5$-$C_{12}$ cycloalkenyl, each group being optionally substituted by one or several groups (for example 1, 2, 3, or 4), either identical or different, selected from the group comprising a halogen atom, —OH, oxo, cyano, epoxy, —OCOL$^1$R$^5$, —OCOR$^8$, —CO$_2$R$^{60}$, $C_1$-$C_6$ alkyl, $C_1$-$C_6$ hydroxyalkyl, and $C_2$-$C_6$ alkenyl; or else $R^1$ and $R^3$ may preferably, with the carbons to which they are bound, form a group selected from a $C_5$-$C_{12}$ cycloalkyl or a $C_5$-$C_{12}$ cycloalkenyl, with each group being optionally substituted by 1, 2, 3 or 4 groups, either identical or different, selected from the group comprising an —OH, oxo, epoxy, —OCOL$^1$R$^5$, —OCOR$^8$, —CO$_2$R$^{60}$, $C_1$-$C_6$ alkyl, and $C_2$-$C_6$ alkenyl; or else $R^1$ and $R^3$ may preferably, with the carbons to which they are bound, form a group selected from a $C_5$-$C_{10}$ cycloalkyl or a $C_5$-$C_{10}$ cycloalkenyl, with each group being optionally substituted by 1, 2 or 3 groups, either identical or different, selected from —OH, epoxy, $C_1$-$C_6$ alkyl, or $C_2$-$C_6$ alkenyl;

$R^5$ is selected from the group comprising H, a halogen atom, —OH, —CHO, epoxy, —SR$^8$, cyano, nitro, isocyanate, $C_1$-$C_{20}$ alkyl, $C_1$-$C_4$ alkoxy, $C_2$-$C_{20}$ alkenyl, $C_2$-$C_{20}$ alkynyl, heterocycloalkyl, —CO$_2$R$^8$, and —NR$^9{}_2$; preferably $R^5$ is selected from the group comprising Cl, F, I, Br, —OH, —SH, —CHO, epoxy, cyano, nitro, isocyanate, $C_1$-$C_4$ alkoxy, $C_2$-$C_{12}$ alkenyl, $C_2$-$C_{12}$ alkynyl, heterocycloalkyl, —CO$_2$R$^8$, and —NR$^9{}_2$; preferably, $R^5$ is selected from the group comprising Cl, F, I, Br, —OH, —CHO, epoxy, —SH, cyano, and nitro; preferably —OH, —SH, epoxy, cyano or nitro; preferably —OH, —SH, epoxy or cyano;

$R^6$ is H or —CO-L$^1$-R$^5$;

$L^1$ is a single covalent bond, or is selected from the group comprising $C_1$-$C_{20}$ alkylene, $C_3$-$C_{12}$ cycloalkylene, $C_2$-$C_{12}$ alkenylene, $C_5$-$C_{12}$ cycloalkenylene, $C_6$-$C_{12}$ arylene, heteroarylene, and heterocycloalkylene, each group being optionally substituted by one or several groups (for example 1, 2, 3, or 4), either identical or different, selected from the group comprising a halogen atom, —OH, oxo, nitro, —CHO, —OCOL$^1$R$^5$, —CO$_2$R$^{60}$, —NR$^9{}_2$, $C_1$-$C_6$ alkyl, $C_1$-$C_4$ alkoxy, $C_6$-$C_{12}$ aryl, $C_6$-$C_{12}$ aryloxy, $C_6$-$C_{12}$ aryl$C_{1-6}$ alkyl, $C_1$-$C_6$ hydroxyalkyl, and $C_{1-6}$ alkyl$C_6$-$C_{12}$aryl; preferably $L^1$ is a single covalent bond, or is selected from the group comprising $C_1$-$C_{20}$ alkylene, $C_3$-$C_{12}$ cycloalkylene, $C_5$-$C_{12}$ cycloalkenylene and $C_6$-$C_{12}$ arylene, with each group being optionally substituted by 1, 2, 3 or 4 groups, either identical or different, selected from the group comprising a halogen atom, —OH, oxo, —CHO, —OCOL$^1$R$^5$, —CO$_2$R$^{60}$, —NR$^9{}_2$, $C_1$-$C_6$ alkyl, $C_1$-$C_4$ alkoxy, $C_1$-$C_6$ hydroxyalkyl, and $C_6$-$C_{12}$ aryl; preferably $L^1$ is a single covalent bond, or is selected from the group comprising $C_1$-$C_{11}$ alkylene, $C_3$-$C_{12}$ cycloalkylene, and $C_6$-$C_{12}$ arylene, with each group being optionally substituted by 1, 2, 3 or 4 groups, either identical or different, selected from the group comprising a halogen atom, —OH, —CHO, —OCOL$^1$R$^5$, —CO$_2$R$^{60}$, $C_1$-$C_6$ alkyl, and $C_6$-$C_{12}$ aryl; preferably $L^1$ is a single covalent bond, or is a $C_1$-$C_{11}$ alkylene, or a $C_3$-$C_{12}$ cycloalkylene; optionally substituted by 1, 2, or 3 groups, either identical or different, selected from the group comprising a halogen atom, —OH, —CHO, —OCOL$^1$R$^5$, —CO$_2$R$^{60}$, $C_1$-$C_6$ alkyl, and $C_6$-$C_{12}$ aryl;

$R^{10}$ is H, or is selected from the group comprising $C_1$-$C_{20}$ alkyl, $C_2$-$C_{20}$ alkenyl, and $C_6$-$C_{12}$ aryl, each group being optionally substituted by one or several groups (for example 1, 2, 3, or 4), either identical or different, selected from the group comprising a halogen atom, —OH, —CHO, oxo, cyano, —$NR^9{}_2$, epoxy, $C_1$-$C_4$ alkoxy, —$OCOL^2R^{50}$, $C_1$-$C_6$ alkyl, $C_6$-$C_{12}$ aryl, —$OCOR^8$, and —$CO_2R^{60}$; preferably $R^{10}$ is H, or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, cyano, —$NR^9{}_2$, epoxy, $C_1$-$C_4$ alkoxy, —$OCOL^2R^{50}$, $C_1$-$C_6$ alkyl, $C_6$-$C_{12}$ aryl, —$OCOR^8$, and —$CO_2R^{60}$; preferably $R^{10}$ is H, or is selected from the group comprising $C_1$-$C_{20}$ alkyl, and $C_2$-$C_{20}$ alkenyl, with each group being optionally substituted by 1, 2 or 3 groups, either identical or different, selected from the group comprising —OH, —CHO, oxo, —$OCOL^2R^{50}$, $C_1$-$C_2$ alkoxy, $C_1$-$C_6$ alkyl, and —$CO_2R^{60}$; preferably $R^{10}$ is H, or is selected from the group comprising $C_1$-$C_{12}$ alkyl, and $C_2$-$C_{12}$ alkenyl, with each group being optionally substituted by 1, 2 or 3 groups, either identical or different, selected from —CHO, oxo, $C_1$-$C_6$ alkyl, or —$OCOL^2R^{50}$;

$R^{20}$ is H, cyano, a halogen atom, or —CHO, or is selected from the group comprising $C_1$-$C_{20}$ alkyl, $C_2$-$C_{20}$ alkenyl, $C_6$-$C_{12}$ aryl, and $C_6$-$C_{12}$ aryl$C_{1-6}$alkyl, each group being optionally substituted by one or several groups (for example 1, 2, 3, or 4), either identical or different, selected from the group comprising a halogen atom, —OH, —CHO, oxo, cyano, —$NR^9{}_2$, epoxy, $C_1$-$C_4$ alkoxy, —$OCOL^2R^{50}$, $C_1$-$C_6$ alkyl, $C_6$-$C_{12}$ aryl, —$OCOR^8$, and —$CO_2R^{60}$; preferably $R^{20}$ is H or —CHO or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, cyano, —$NR^9{}_2$, epoxy, $C_1$-$C_4$ alkoxy, —$OCOL^2R^{50}$, $C_1$-$C_6$ alkyl, $C_6$-$C_{12}$ aryl, $OCOR^8$, and —$CO_2R^{60}$; preferably $R^{20}$ is H or —CHO, or is selected from the group comprising $C_1$-$C_{20}$ alkyl, and $C_2$-$C_{20}$ alkenyl, with each group being optionally substituted by 1, 2 or 3 groups, either identical or different, selected from —OH, oxo, —CHO, —$OCOL^2R^{50}$ $C_1$-$C_2$ alkoxy, or $C_1$-$C_6$ alkyl; preferably $R^{20}$ is H or —CHO, or is selected from the group comprising $C_1$-$C_{12}$ alkyl, and $C_2$-$C_{12}$ alkenyl, with each group being optionally substituted by 1, 2 or 3 groups, either identical or different, selected from —CHO, $C_1$-$C_6$ alkyl, or —$OCOL^2R^{50}$;

$R^{30}$ is selected from the group comprising epoxy, —$OCOR^8$, —$CO_2R^8$, $C_1$-$C_{20}$ alkyl, $C_2$-$C_{20}$ alkenyl, $C_6$-$C_{12}$ aryl, and $C_6$-$C_{12}$ aryl$C_{1-6}$alkyl, each group being optionally substituted by one or several groups (for example 1, 2, 3, or 4), either identical or different, selected from the group comprising a halogen atom, —OH, —CHO, oxo, cyano, —$NR^9{}_2$, epoxy, $C_1$-$C_4$ alkoxy, —$OCOL^2R^{50}$, $C_1$-$C_6$ alkyl, $C_6$-$C_{12}$ aryl, —$OCOR^8$, and —$CO_2R^{60}$; preferably $R^{30}$ is selected from the group comprising epoxy, $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, $C_1$-$C_6$ alkyl, —CHO, oxo, epoxy, $C_1$-$C_4$ alkoxy, —$OCOL^2R^{50}$, $C_6$-$C_{12}$ aryl, —$OCOR^8$, and —$CO_2R^{60}$; preferably $R^{30}$ is selected from the group comprising $C_1$-$C_{20}$ alkyl, and $C_2$-$C_{20}$ alkenyl, with each group being optionally substituted by 1, 2 or 3 groups, either identical or different, selected from oxo, $C_1$-$C_2$ alkoxy, $C_1$-$C_6$ alkyl, —CHO, —$OCOL^2R^{50}$ or —$CO_2R^{60}$; preferably $R^{30}$ is selected from the group comprising $C_1$-$C_{12}$ alkyl, and $C_2$-$C_{12}$ alkenyl, with each group being optionally substituted by 1, 2 or 3 groups, either identical or different, selected from $C_1$-$C_6$ alkyl, —CHO, —$OCOL^2R^{50}$, or —$CO_2R^{60}$;

$R^{40}$ is H, cyano, a halogen atom, or —CHO, or is selected from the group comprising $C_1$-$C_{20}$ alkyl, $C_2$-$C_{20}$ alkenyl, and $C_6$-$C_{12}$ aryl, each group being optionally substituted by one or several groups (for example 1, 2, 3, or 4), either identical or different, selected from the group comprising a halogen atom, —OH, —CHO, oxo, cyano, —$NR^9{}_2$, epoxy, $C_1$-$C_4$ alkoxy, —$OCOL^2R^{50}$, $C_1$-$C_6$ alkyl, $C_6$-$C_{12}$ aryl, —$OCOR^8$, and —$CO_2R^{60}$; preferably $R^{40}$ is H or —CHO, or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, oxo, epoxy, $C_1$-$C_4$ alkoxy, $C_1$-$C_6$ alkyl, $C_6$-$C_{12}$ aryl, —$OCOL^2R^{50}$, and —$CO_2R^{60}$; preferably $R^{40}$ is H or —CHO, or is selected from the group comprising $C_1$-$C_{20}$ alkyl, and $C_2$-$C_{20}$ alkenyl, with each group being optionally substituted by 1, 2 or 3 groups, either identical or different, selected from the group comprising oxo, $C_1$-$C_2$ alkoxy, $C_1$-$C_6$ alkyl, —$OCOL^2R^{50}$, and —$CO_2R^{60}$; preferably $R^{40}$ is H or —CHO, or is selected from the group comprising $C_1$-$C_{12}$ alkyl, and $C_2$-$C_{12}$ alkenyl, with each group being optionally substituted by 1, 2 or 3 groups, either identical or different, selected from $C_1$-$C_6$ alkyl, —$OCOL^2R^{50}$, or —$CO_2R^{60}$; preferably $R^{40}$ is H, —CHO or $C_1$-$C_{12}$ alkyl, optionally substituted by 1, 2 or 3 groups, either identical or different, selected from $C_1$-$C_6$ alkyl, —$OCOL^2R^{50}$, or —$CO_2R^{60}$; preferably $R^{40}$ is H or —CHO; or $R^{10}$ and $R^{30}$ may, with the carbons to which they are bound, form a group selected from a $C_5$-$C_{12}$ cycloalkyl or a $C_5$-$C_{12}$ cycloalkenyl, each group being optionally substituted by one or several groups (for example 1, 2, 3, or 4), either identical or different, selected from the group comprising a halogen atom, —OH, —CHO, cyano, oxo, epoxy, —$OCOR^8$, —$CO_2R^{60}$, —$OCOL^2R^{50}$, $C_1$-$C_6$ alkyl, $C_1$-$C_6$ hydroxyalkyl, and $C_2$-$C_6$ alkenyl; or else $R^{10}$ and $R^{30}$ may preferably, with the carbons to which they are bound, form a group selected from a $C_5$-$C_{12}$ cycloalkyl or a $C_5$-$C_{12}$ cycloalkenyl, with each group being optionally substituted by 1, 2, 3 or 4 groups, either identical or different, selected from the group comprising —OH, —CHO, oxo, epoxy, —$OCOL^2R^{50}$, $C_1$-$C_6$ alkyl, and $C_2$-$C_6$ alkenyl; preferably $R^{10}$ and $R^{30}$ may, with the carbons to which they are bound, form a group selected from a $C_5$-$C_{10}$ cycloalkyl or a $C_5$-$C_{10}$ cycloalkenyl, with each group being optionally substituted by 1, 2 or 3 groups, either identical or different, selected from the group comprising —OH, —CHO, epoxy, $C_1$-$C_6$ alkyl, and $C_2$-$C_6$ alkenyl;

$R^{50}$ is selected from the group comprising H, —CHO, epoxy, a halogen atom, —OH, cyano, nitro, isocyanate, $C_1$-$C_{20}$ alkyl, $C_1$-$C_4$ alkoxy, $C_2$-$C_{20}$ alkenyl, $C_2$-$C_{20}$ alkynyl, heterocycloalkyl, —$CO_2R^8$, and —$NR^9{}_2$; preferably $R^{50}$ is selected from the group comprising Cl, F, I, Br, —OH, —CHO, epoxy, —SH, cyano, nitro, isocyanate, $C_1$-$C_4$ alkoxy, $C_2$-$C_{12}$ alkenyl, $C_2$-$C_{12}$ alkynyl, heterocycloalkyl, —$CO_2R^8$, and —$NR^9{}_2$; preferably, $R^{50}$ is selected from the group comprising Cl, F, I, Br, —OH, —CHO, —SH, cyano, and nitro, preferably —OH, —CHO, —SH, epoxy, cyano or nitro, preferably —OH, —SH or cyano;

$L^2$ is a single covalent bond, or is selected from the group comprising $C_1$-$C_{20}$ alkylene, $C_3$-$C_{12}$ cycloalkylene, $C_2$-$C_{12}$ alkenylene, $C_5$-$C_{12}$ cycloalkenylene, $C_6$-$C_{12}$ arylene, heteroarylene, and heterocycloalkylene, each group being optionally substituted by one or several groups (for example 1, 2, 3, or 4), either identical or different, selected from the group comprising a halogen atom, oxo, nitro, —CHO, —OH, —$NR^9{}_2$, $C_1$-$C_6$ alkyl, $C_1$-$C_4$ alkoxy, $C_6$-$C_{12}$ aryl$C_{1-6}$alkyl, $C_{1-6}$ alkyl$C_6$-$C_{12}$aryl, $C_6$-$C_{12}$ aryloxy, $C_1$-$C_6$ hydroxyalkyl, and $C_6$-$C_{12}$ aryl; preferably $L^2$ is a single covalent bond, or is selected from the group comprising $C_1$-$C_{20}$ alkylene, $C_3$-$C_{12}$ cycloalkylene, $C_5$-$C_{12}$ cycloalkenylene, and $C_6$-$C_{12}$ arylene, with each group being optionally substituted by 1, 2, 3 or 4 groups, either identical or different, selected from the group comprising a halogen atom, —OH, —CHO, nitro, —CO$_2$R$^{60}$, —NR$^9{}_2$, $C_1$-$C_6$ alkyl, $C_1$-$C_4$ alkoxy, $C_1$-$C_6$ hydroxyalkyl, and $C_6$-$C_{12}$ aryl; preferably $L^2$ is a single covalent bond, or is selected from the group comprising $C_1$-$C_{11}$ alkylene, $C_3$-$C_{12}$ cycloalkylene, and $C_6$-$C_{12}$ arylene, with each group being optionally substituted by 1, 2, 3 or 4 groups, either identical or different, selected from the group comprising a halogen atom, —OH, —CHO, —CO$_2$R$^{60}$, $C_1$-$C_6$ alkyl, and $C_6$-$C_{12}$ aryl; preferably $L^2$ is a single covalent bond, or is a $C_1$-$C_{11}$ alkylene, or a $C_3$-$C_{12}$ cycloalkylene; optionally replaced by 1, 2 or 3 groups, either identical or different, chosen from the group comprising a halogen atom, —OH, —CHO, —CO$_2$R$^{60}$, $C_1$-$C_6$ alkyl, and $C_6$-$C_{12}$ aryl;

$R^{60}$ is selected from the groups comprising H or $C_1$-$C_6$ alkyl optionally substituted by one or several groups (for example 1, 2, 3, or 4), either identical or different, chosen from the group comprising —OH, —CHO, —O—COR$^7$, and $C_1$-$C_6$ alkyl; preferably $R^{60}$ is selected from the groups comprising H or $C_1$-$C_4$ alkyl, optionally substituted by 1, 2 or 3 groups, either identical or different, selected from the group comprising —OH, —CHO, —O—COR$^7$, and $C_1$-$C_4$ alkyl;

$R^7$ is selected from the group comprising $C_1$-$C_{24}$ alkyl, $C_2$-$C_{20}$ alkenyl, and $C_6$-$C_{12}$ aryl, with each group being optionally substituted by one or several groups, either identical or different, chosen from the group comprising —OH, epoxy and —OCOL$^1$R$^5$; $R^7$ is preferably selected from the group comprising $C_4$-$C_{24}$ alkyl, $C_4$-$C_{20}$ alkenyl, and $C_6$-$C_{12}$ aryl, with each group being optionally substituted by 1, 2 or 3 identical or different groups, selected from —OH, epoxy, or —OCOL$^1$R$^5$;

$R^7$ is preferably selected from the group comprising $C_6$-$C_{24}$ alkyl, and $C_6$-$C_{20}$ alkenyl, with each group being optionally substituted by 1, 2 or 3 identical or different groups, selected from —OH, epoxy, or —OCOL$^1$R$^5$; preferably $R^7$ is selected from the group comprising $C_{10}$-$C_{24}$ alkyl, and $C_{10}$-$C_{20}$ alkenyl, with each group being optionally substituted by 1, 2 or 3 identical or different groups, selected from —OH, epoxy, or —OCOL$^1$R$^5$; $R^7$ is preferably selected from the group comprising $C_{18}$-$C_{24}$ alkyl, and $C_{18}$-$C_{20}$ alkenyl, with each group being optionally substituted by 1, 2 or 3 identical or different groups, selected from —OH, epoxy, or —OCOL$^1$R$^5$;

$R^8$ is selected from H or $C_1$-$C_6$ alkyl; preferably $R^8$ is selected from H or $C_1$-$C_4$ alkyl; preferably $R^8$ is selected from H or $C_1$-$C_2$ alkyl; and each identical or different $R^9$ is selected from H, $C_1$-$C_6$ alkyl, or $C_6$-$C_{12}$ aryl, preferably each identical or different $R^9$ is selected from H or $C_1$-$C_4$ alkyl; preferably each identical or different $R^9$ is selected from H or $C_1$-$C_2$ alkyl.

The term "$C_1$-$C_{20}$ alkyl" refers to a linear or branched, saturated hydrocarbon radical, comprising from 1 to 20 carbon atoms, such as methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl.

The term "$C_1$-$C_{20}$ alkenyl" refers to a linear or branched hydrocarbon radical, comprising one or several double bonds, having from 2 to 20 carbon atoms. Branched means that one or several lower alkyl groups, such as methyl, ethyl or propyl, are bound to a linear alkenyl chain. By way of example of a $C_1$-$C_{20}$ alkenyl one may cite the ethenyl group, 1-propenyl, 2-propenyl, 1-butenyl, 2-butenyl, 1-pentenyl, 2-pentenyl, 3-methyl-3-butenyl, 1-hexenyl, 2-hexenyl, 1-heptenyl, 2-heptenyl, 3-heptenyl, 1-octenyl, 4-octenyl, 4-nonenyl, 5-decenyl, 5-undecenyl, 6-dodecenyl, tetradecenyl, 9-hexadecenyl, 9-octadecenyl, 13-docosaenyl, 15-tetracosaenyl, 9,12-octadecadienyl, 9,12,15-octadecatrienyl, 6,9,12-octadecatrienyl, 8,11,14-eicosatrienyl, 5,8,11,14-eicosatetraenyl, 5,8,11,14,17-eicosapentaenyl, and 4,7,10,13,16,19-docosahexaenoyl.

The term "$C_5$-$C_{12}$ cycloalkyl" refers to a saturated mono- or polycyclic hydrocarbon radical, having from 5 to 12 carbon atoms. By way of example of a monocyclic cycloalkyl, one may cite for example cyclopentyl, cyclohexyl, cycloheptyl, cyclooctyl, cyclodecyl, and cyclododecyl. By way of example of a polycyclic cycloalkyl group, one may cite in particular 1-decaline, norbornyl, or adamant-(1 or 2-)yl.

The term "$C_5$-$C_{12}$ cycloalkenyl" refers to a group derived from a cycloalkyl group, as defined above, presenting one or several double bonds. For example, this could be the cyclopentenyl group, cyclohexenyl, cyclopenta-1,3-dienyl, cycloheptenyl, cyclooctenyl, cycloocta-1,4-dienyl, cyclodecenyl, cyclodeca-1,5-dienyl.

The term "$C_2$-$C_{20}$ alkynyl" refers to a linear or branched hydrocarbon chain comprising one or several trible bonds. Branched means that one or several lower alkyl groups, such as methyl, ethyl or propyl, are bound to a linear alkynyl chain. Examples of alkynyl groups are in particular the groups ethynyl, 1-propynyl, 1-butynyl, 2-butynyl, etc.

The term "$C_6$-$C_{12}$ aryl" refers to an aromatic monocyclic or polycyclic hydrocarbon radical, having 6 to 12 atoms of carbon, more preferably 6 carbon atoms. The aryl groups include in particular include the phenyl, naphtyl and biphenyl groups.

The term "$C_{1-6}$ alkyl$C_6$-$C_{12}$aryl" refers to an aryl group substituted by at least one $C_1$-$C_6$ alkyl group, with the aryl and alkyl groups being as defined above.

The term "$C_6$-$C_{12}$ aryl$C_{1-6}$alkyl" or "aralkyl" refers to an alkyl group substituted by at least one $C_6$-$C_{12}$ aryl group, with the aryl and alkyl groups being as defined above. As an example of aralkyl groups, one may consider in particular benzyl, 2-phenethyl and naphthalenemethyl.

The term "$C_1$-$C_4$ alkoxy" refers to an alkyl-O— group in which the alkyl term has the meaning given above. Examples of $C_1$-$C_4$ alkoxy groups are the methoxy, ethoxy, propoxy, and butoxy groups.

The term "$C_6$-$C_{12}$ aryloxy" refers to an aryl-O— group in which the aryl term has the meaning given above. An example of a $C_6$-$C_{12}$ aryloxy group is phenoxy.

The term "heterocycloalkyl" refers to mono-, bi- or polycyclic hydrocarbon systems, saturated or unsaturated, presenting at least one heteroatom on the cycle(s), such as nitrogen, sulfur or oxygen. They are non-aromatic. For the heterocycle, one can cite in particular the piperidine group, piperazine, pyrrolidine, pyrrolidinone, morpholine, phthalane, phthalide, thiazolidinedione, sulfolane, benzo[1,3]dioxolane, benzo[1,4]dioxane, [2,3]dihydrobenzofurane, quinazolinone, benzothiadiazinone, 1-methyl-piperidin-4-yl or 1-methyl-piperidin-4-ylmethyl.

The term "heteroaryl" refers to one or several aromatic unsaturated cycles comprising one or several heteroatoms, either identical or different, selected from N, O and S, such as the pyridinyl, pyrimidinyl, furyl, thienyl, benzothienyl, oxazolyl, benzoxazolyl, isoxazolyl, thiazolyl, pyrolyl, pyrazolyl, imidazolyl, triazolyl, and tetrazolyl groups.

The term "$C_1$-$C_{11}$ alkylene" refers to a linear or branched, saturated, divalent alkyl group. Examples of alkylene groups are, in particular, the methylene, ethylene, 1-methyl ethylene, propylene, etc. groups.

The term "$C_2$-$C_{12}$ alkenylene" refers to a divalent alkenyl group, with the alkenyl group being as defined above.

The term "$C_3$-$C_{12}$ cycloalkylene" refers to a divalent cycloalkyl group, with the cycloalkyl group being as defined above.

The term "$C_6$-$C_{12}$ arylene" refers to a divalent aryl group, with the aryl group being as defined above.

The term "heterocycloalkylene" refers to a divalent heterocycloalkyl group, with the heterocycloalkyl group being as defined above.

The term "heteroarylene" refers to a divalent heteroarylene group, with the heteroarylene group being as defined above.

The term "hydroxyalkyl" designates groups in which the alkyl group is as defined above, and in which at least one carbon atom is substituted by a hydroxyl radical, for example hydroxymethyl, hydroxyethyl, 2-hydroxy-butyl.

The term "halogen" or "halogen atom" refers to a chlorine, bromine, fluorine or iodine atom.

The term "oxo" refers to a =O group.

The term "cyano" refers to a —C≡N group.

The term "epoxy" refers to a

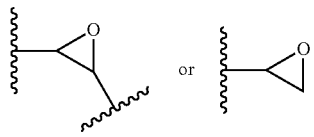

group.

The term "polymer" is understood to mean a molecule of formula (Ic) or (Id),

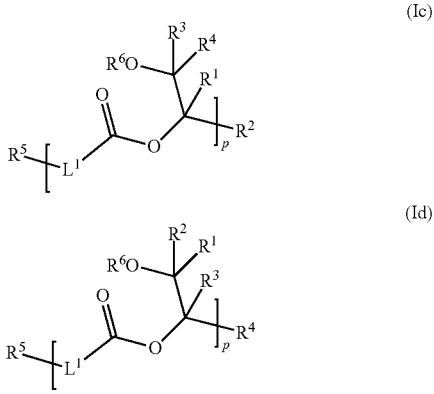

where p is repeated a large number of times (up to several thousands). For example, p is a whole number comprised between 1 and 10,000, preferably p is a whole number comprised between 1 and 1,000, for example p is a whole number comprised between 1 and 100. Preferably the polymer of the compound of formula (Ia) or (Ib) is an oligomer. "Oligomer" is understood to mean a molecule of formula (Ic) or (Id) in which p is repeated less than 20 times (p is a whole number less than 20).

The foregoing definitions are applicable to the description, the examples and the claims of the invention. In order to facilitate understanding, the nomenclature of groups, reagents, solvents and products is the international nomenclature or the nomenclature commonly used by a person skilled in the art.

According to a preferred embodiment, the invention relates to a process of synthesizing compounds of the family represented by formula (Ia) or (Ib), a stereoisomer, a mix of compounds belonging to this family, and/or an oligomer and/or a polymer thereof, wherein:

$R^1$ is H or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, cyano, —$NR^9_2$, epoxy, $C_1$-$C_4$ alkoxy, $C_1$-$C_6$ alkyl, $C_6$-$C_{12}$ aryl, —$OCOL^1R^5$, —$OCOR^8$, and —$CO_2R^{60}$;

$R^2$ is H or is selected from the group comprising $C_1$-$C_{20}$ alkyl, $C_2$-$C_{20}$ alkenyl, $C_6$-$C_{12}$ aryl, and $C_6$-$C_{12}$ aryl$C_{1-6}$alkyl, with each group being optionally substituted by 1, 2 or 3 groups, either identical or different, selected from the group comprising —OH, —CHO, epoxy, oxo, cyano, —$NR^9_2$, $C_1$-$C_4$ alkoxy, $C_1$-$C_6$ alkyl, $C_6$-$C_{12}$ aryl, —$OCOL^1R^5$, —$OCOR^8$, and —$CO_2R^{60}$;

$R^3$ is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, epoxy, $C_1$-$C_4$ alkoxy, $C_1$-$C_6$ alkyl, $C_6$-$C_{12}$ aryl, —$OCOL^1R^5$ and —$CO_2R^{60}$;

$R^4$ is H, or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, epoxy, $C_1$-$C_4$ alkoxy, $C_1$-$C_6$ alkyl, $C_6$-$C_{12}$ aryl, —$OCOL^1R^5$, and —$CO_2R^{60}$;

or $R^1$ and $R^3$ may, with the carbons to which they are bound, form a group selected from a $C_5$-$C_{12}$ cycloalkyl or a $C_5$-$C_{12}$ cycloalkenyl, with each group being optionally substituted by 1, 2, 3 or 4 groups, either identical or different, selected from the group comprising an —OH, oxo, epoxy, —$OCOL^1R^5$, —$OCOR^8$, —$CO_2R^{60}$, $C_1$-$C_6$ alkyl, and $C_2$-$C_6$ alkenyl;

$R^5$ is selected from the group comprising Cl, F, I, Br, —OH, —SH, —CHO, epoxy, cyano, nitro, isocyanate, $C_1$-$C_4$ alkoxy, $C_2$-$C_{12}$ alkenyl, $C_2$-$C_{12}$ alkynyl, heterocycloalkyl, —$CO_2R^8$, and —$NR^9_2$;

$R^6$ is H or —CO-$L^1$-$R^5$;

$L^1$ is a single covalent bond, or is selected from the group comprising $C_1$-$C_{20}$ alkylene, $C_3$-$C_{12}$ cycloalkylene, $C_5$-$C_{12}$ cycloalkenylene, and $C_6$-$C_{12}$ arylene, with each group being optionally substituted by 1, 2, 3 or 4 groups, either identical or different, selected from the group comprising a halogen atom, —OH, oxo, —CHO, —$OCOL^1R^5$, —$CO_2R^{60}$, $C_1$-$C_6$ alkyl, $C_1$-$C_4$ alkoxy, $C_1$-$C_6$ hydroxyalkyl, and $C_6$-$C_{12}$ aryl;

$R^{60}$ is selected from the groups comprising H and $C_1$-$C_4$ alkyl optionally substituted by 1, 2 or 3 groups, either identical or different, selected from the group comprising —OH, —CHO, —O—$COR^7$, and $C_1$-$C_4$ alkyl;

$R^7$ is selected from the group comprising $C_4$-$C_{24}$ alkyl, $C_4$-$C_{20}$ alkenyl, and $C_6$-$C_{12}$ aryl, with each group being optionally substituted by 1, 2 or 3 identical or different groups, chosen from the group comprising —OH, epoxy and —$OCOL^1R^5$;

$R^8$ is selected from H or $C_1$-$C_4$ alkyl; and each identical or different $R^9$ is selected from H or $C_1$-$C_4$ alkyl.

According to a preferred embodiment, the invention concerns a process for the synthesis of compounds of the family represented by formula (Ia) or (Ib), a stereoisomer, a combination of compounds of this family, and/or an oligomer and/or a polymer thereof, wherein:

$R^1$ is H or is selected from the group comprising $C_1$-$C_{20}$ alkyl, and $C_2$-$C_{20}$ alkenyl, with each group being optionally substituted by 1, 2 or 3 groups, either identical or different, selected from the group comprising —OH, oxo, $C_1$-$C_2$ alkoxy, $C_1$-$C_6$ alkyl, —OCOL$^1$R$^5$, and —CO$_2$R$^{60}$;

$R^2$ is H or is selected from the group comprising $C_1$-$C_{20}$ alkyl, and $C_2$-$C_{20}$ alkenyl, with each group being optionally substituted by 1, 2 or 3 groups, either identical or different, selected from the group comprising oxo, $C_1$-$C_2$ alkoxy, $C_1$-$C_6$ alkyl, —OCOL$^1$R$^5$, and —CO$_2$R$^{60}$;

$R^3$ is selected from the group comprising $C_1$-$C_{20}$ alkyl, and $C_2$-$C_{20}$ alkenyl, with each group being optionally substituted by 1, 2 or 3 groups, either identical or different, selected from the group comprising —OH, oxo, $C_1$-$C_2$ alkoxy, $C_1$-$C_6$ alkyl, —OCOL$^1$R$^5$ and —CO$_2$R$^{60}$;

$R^4$ is H, or is selected from the group comprising $C_1$-$C_{20}$ alkyl, and $C_2$-$C_{20}$ alkenyl, with each group being optionally substituted by 1, 2 or 3 groups, either identical or different, selected from the group comprising oxo, $C_1$-$C_2$ alkoxy, $C_1$-$C_6$ alkyl, —OCOL$^1$R$^5$, and —CO$_2$R$^{60}$;

or $R^1$ and $R^3$ may, with the carbons to which they are bound, form a group selected from a $C_5$-$C_{10}$ cycloalkyl and a $C_5$-$C_{10}$ cycloalkenyl, with each group being optionally substituted by 1, 2 or 3 groups, either identical or different, chosen from the group comprising —OH, epoxy, $C_1$-$C_6$ alkyl, and $C_2$-$C_6$ alkenyl;

$R^5$ is selected from the group comprising Cl, F, I, Br, —OH, —CHO, epoxy, —SH, cyano, and nitro, preferably —OH, —SH, epoxy, cyano, and nitro, preferably —OH, —SH, epoxy, or cyano;

$R^6$ is H or —CO-L$^1$-R$^5$;

$L^1$ is a single covalent bond, or is selected from the group comprising $C_1$-$C_{11}$ alkylene, $C_3$-$C_{12}$ cycloalkylene, and $C_6$-$C_{12}$ arylene, with each group being optionally substituted by 1, 2, 3 or 4 groups, either identical or different, selected from the group comprising a halogen atom, —OH, —CHO, —OCOL$^1$R$^5$, —CO$_2$R$^{60}$, $C_1$-$C_6$ alkyl, and $C_6$-$C_{12}$ aryl;

$R^{60}$ is selected from the group comprising H and $C_1$-$C_4$ alkyl optionally substituted by 1, 2 or 3 groups, either identical or different, selected from the group comprising —OH, —CHO, —O—COR$^7$, and $C_1$-$C_4$ alkyl;

$R^7$ is selected from the group comprising $C_6$-$C_{24}$ alkyl, and $C_6$-$C_{20}$ alkenyl, with each group being optionally substituted by 1, 2 or 3 groups, either identical or different, selected from the group comprising —OH, epoxy and —OCOL$^1$R$^5$;

$R^8$ is selected from H or $C_1$-$C_4$ alkyl; and each $R^9$ that is identical or different is selected from H or $C_1$-$C_4$ alkyl.

The invention therefore relates to a process for the preparation of compounds of formula (Ia), (Ib), (Ic) or (Id), or a combination thereof, since said procedure includes the reaction of at least one unsaturated molecule of formula (II) with atmospheric or molecular oxygen, in the presence of at least one aldehyde of formula (III), and optionally in the presence of at least one catalyst or at least one radical initiator. According to a particular embodiment, the unsaturated molecule of formula (II) may be the same molecule as the aldehyde of formula (III).

According to a particular embodiment, the process comprises the reaction of an unsaturated molecule of formula (II) with atmospheric or molecular oxygen, in the presence of at least one aldehyde of formula (III) and optionally in the presence of at least one catalyst or at least one radical initiator, wherein:

$R^{10}$ is H, or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CO$_2$R$^{60}$;

$R^{20}$ is H or —CHO or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, OCOR$^8$, and —CO$_2$R$^{60}$;

$R^{30}$ is selected from the group comprising epoxy, $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, $C_1$-$C_6$ alkyl, —CHO, oxo, epoxy, $C_1$-$C_4$ alkoxy, —OCOL$^2$R$^{50}$, $C_6$-$C_{12}$ aryl, —OCOR$^8$, and —CO$_2$R$^{60}$;

$R^{40}$ is H or —CHO, or is selected from the group comprising $C_1$-$C_{20}$ alkyl, $C_2$-$C_{20}$ alkenyl, and $C_6$-$C_{12}$ aryl, with each group being optionally substituted by 1, 2 or 3 groups, either identical or different, selected from the group comprising —OH, oxo, epoxy, $C_1$-$C_4$ alkoxy, $C_1$-$C_6$ alkyl, $C_6$-$C_{12}$ aryl, —OCOL$^2$R$^{50}$, and —CO$_2$R$^{60}$;

or $R^{10}$ and $R^{30}$ may, with the carbons to which they are bound, form a group selected from a $C_5$-$C_{12}$ cycloalkyl or a $C_5$-$C_{12}$ cycloalkenyl, with each group being optionally substituted by 1, 2, 3 or 4 groups, either identical or different, selected from the group comprising —OH, —CHO, oxo, epoxy, —OCOL$^2$R$^{50}$, $C_1$-$C_6$ alkyl, and $C_2$-$C_6$ alkenyl;

$R^{50}$ is selected from the group comprising Cl, F, I, Br, —OH, —CHO, epoxy, —SH, cyano, nitro, isocyanate, $C_2$-$C_{12}$ alkenyl, $C_2$-$C_{12}$ alkynyl, heterocycloalkyl, —CO$_2$R$^8$, and —NR$^9_2$;

$L^2$ is a single covalent bond, or is selected from the group comprising $C_1$-$C_{20}$ alkylene, $C_3$-$C_{12}$ cycloalkylene, $C_5$-$C_{12}$ cycloalkenylene, and $C_6$-$C_{12}$ arylene, with each group being optionally substituted by 1, 2, 3 or 4 groups, either identical or different, selected from the group comprising a halogen atom, —OH, —CHO, nitro, —CO$_2$R$^{60}$, —NR$^9_2$, $C_1$-$C_6$ alkyl, $C_1$-$C_4$ alkoxy, $C_1$-$C_6$ hydroxyalkyl, and $C_6$-$C_{12}$ aryl;

$R^{60}$ is selected from the groups comprising H and $C_1$-$C_4$ alkyl, optionally substituted by 1, 2 or 3 identical or different groups, selected from the group comprising —OH, —CHO, —O—COR$^7$, and $C_1$-$C_4$ alkyl;

$R^7$ is selected from the group comprising $C_4$-$C_{24}$ alkyl, $C_4$-$C_{20}$ alkenyl, and $C_6$-$C_{12}$ aryl, with each group being optionally substituted by 1, 2, or 3 groups, either identical or different, selected from the group comprising —OH, epoxy, and —OCOL$^1$R$^5$;

$R^8$ is selected from H or $C_1$-$C_4$ alkyl; and
each identical or different $R^9$ is selected from H or $C_1$-$C_4$ alkyl.

According to a preferred embodiment, the process comprises the reaction of an unsaturated molecule of formula (II) with atmospheric or molecular oxygen, in the presence of at least one aldehyde of formula (III) and optionally in the presence of at least one catalyst, or at least one radical initiator, wherein:

$R^{10}$ is H, or is selected from the group comprising $C_1$-$C_{20}$ alkyl, and $C_2$-$C_{20}$ alkenyl, with each group being optionally substituted by 1, 2 or 3 groups, either identical or different, selected from the group comprising —OH, —CHO, oxo, —OCOL$^2$R$^{50}$, $C_1$-$C_2$ alkoxy, and $C_1$-$C_6$ alkyl;

$R^{20}$ is H or —CHO, or is selected from the group comprising $C_1$-$C_{20}$ alkyl, and $C_2$-$C_{20}$ alkenyl, with each group being optionally substituted by 1, 2 or 3 groups, either identical or different, selected from the group comprising —OH, oxo, —CHO, —OCOL$^2$R$^{50}$, $C_1$-$C_2$ alkoxy, and $C_1$-$C_6$ alkyl;

$R^{30}$ is selected from the group comprising $C_1$-$C_{20}$ alkyl, and $C_2$-$C_{20}$ alkenyl, with each group being optionally substituted by 1, 2 or 3 groups, either identical or different, selected from the group comprising oxo, $C_1$-$C_2$ alkoxy, $C_1$-$C_6$ alkyl, —CHO, —OCOL$^2$R$^{50}$ and —CO$_2$R$^{60}$;

R$^{40}$ is H or —CHO, or is selected from the group comprising $C_1$-$C_{20}$ alkyl, and $C_2$-$C_{20}$ alkenyl, with each group being optionally substituted by 1, 2 or 3 groups, either identical or different, selected from $C_1$-$C_2$ oxo alkoxy, $C_1$-$C_6$ alkyl, —OCOL$^2$R$^{50}$, or —CO$_2$R$^{60}$; or R$^{10}$ and R$^{30}$ may, with the carbons to which they are bound, form a group selected from a $C_5$-$C_{10}$ cycloalkyl or a $C_5$-$C_{10}$ cycloalkenyl with each group being optionally substituted by 1, 2 or 3 groups, either identical or different, selected from the group comprising —OH, —CHO, epoxy, $C_1$-$C_6$ alkyl, and $C_2$-$C_6$ alkenyl;

R$^{50}$ is selected from the group comprising Cl, F, I, Br, —OH, —CHO, epoxy, —SH, cyano, and nitro;

L$^2$ is a single covalent bond, or is selected from the group comprising $C_1$-$C_{11}$ alkylene, $C_3$-$C_{12}$ cycloalkylene, and $C_6$-$C_{12}$ arylene, with each group being optionally substituted by 1, 2, 3 or 4 groups, either identical or different, selected from the group comprising a halogen atom, —OH, nitro, —CHO, —CO$_2$R$^{60}$, $C_1$-$C_6$ alkyl, and $C_6$-$C_{12}$ aryl;

R$^{60}$ is selected from the groups comprising H and $C_1$-$C_4$ alkyl optionally substituted by 1, 2 or 3 groups, either identical or different, selected from the group comprising —OH, —CHO, —O—COR$^7$, and $C_1$-$C_4$ alkyl;

R$^7$ is selected from the group comprising $C_6$-$C_{24}$ alkyl, and $C_6$-$C_{20}$ alkenyl, with each group being optionally substituted by 1 or 2 groups, either identical or different, selected from the group comprising —OH, epoxy and —OCOL$^1$R$^5$;

R$^8$ is selected from H or $C_1$-$C_4$ alkyl; and each identical or different R$^9$ is selected from H or $C_1$-$C_4$ alkyl.

According to one particular embodiment, the process may be carried out at atmospheric pressure. According to another particular embodiment, the process may be carried out under pressure or under a constant flow of oxygen or of air. The oxygen flow rate may be controlled, for example by a flow meter. Advantageously, the reaction medium is kept at saturation with dissolved oxygen.

According to a particular embodiment, the process comprises the reaction of at least one saturated molecule of formula (II) with atmospheric or molecular oxygen, in the presence of at least one aldehyde of formula (III).

According to another particular embodiment, the process comprises the reaction of at least one unsaturated molecule of formula (II) with atmospheric or molecular oxygen, in the presence of at least one aldehyde of formula (III), and in the presence of at least one catalyst or in the presence of at least one radical initiator, such as azobisisobutyronitrile (AIBN), azobiscyanocyclohexane (ACHN) or azobis(4-cyanopentanoic) acid (ACVA). According to a preferred embodiment, the reaction is conducted in the presence of a catalyst, preferably a solid catalyst.

According to this embodiment, the process is a heterogeneous catalytic process. Therefore the catalyst is not consumed in the reaction and is not dissolved in the reaction medium. Since it remains in solid form, it is easy to separate it from the reaction medium with no loss of the catalyst and without pollution of the reaction medium by dissolved species or catalyst residue. The solid catalyst may be eliminated by simple filtration or immobilization in a catalyst bed allowing it to be recycled in both cases.

Preferably, the bulk or supported catalyst is a catalyst based on a metal from Groups 6 through 12 of the periodic table of elements and one can preferably cite catalysts based on ruthenium, palladium, platinum, cobalt, manganese, nickel, copper, zinc or iron, deposited for example on a solid support such as aluminas, activated carbons, oxides of zinc, of magnesium and of titanium, silicas, zeolites or polymeric resins.

According to a particular embodiment, the catalyst is selected from the group comprising catalysts based on ruthenium, palladium, platinum, cobalt, manganese, nickel, copper, zinc or iron or activated carbon. According to a preferred embodiment, the catalyst is based on ruthenium, supported nickel or cobalt, or activated carbon. The catalyst is preferably a catalyst based on ruthenium or supported cobalt.

According to a preferred embodiment, the catalyst is based on ruthenium supported on silica prepared from ruthenium chloride and a colloidal silica suspension.

According to another preferred embodiment, the catalyst is a catalyst based on supported nickel, for example a catalyst based on nickel supported on activated carbon.

The catalyst may be introduced into the reaction at a ratio of 0 to 10% by weight of the quantity of unsaturated molecules engaged, for example from 0.1 to 10%, preferably at a ratio of 0.1 to 8%, preferably at a ratio of 0.1 to 5%, Advantageously from 0.5 to 3%, preferably at a ratio of 0.5 to 1%.

According to a particular embodiment, the compound of formula (II) may be a $C_3$-$C_{20}$ alkene or a $C_5$-$C_{12}$ cycloalkene, with each alkene or cycloalkene being optionally substituted by one or several groups, either identical or different, selected from the group comprising a halogen atom, —CHO, —OH, cyano, oxo, epoxy, —OCOR$^8$, $C_1$-$C_6$ alkyl, $C_2$-$C_6$ alkenyl, $C_6$-$C_{12}$ aryl, —OCOL$^2$R$^{50}$, and —CO$_2$R$^{60}$; with each alkyl, alkenyl, or aryl being optionally substituted by one or several groups, either identical or different, selected from the group comprising a halogen atom, oxo, —CHO, —OH, $C_1$-$C_6$ alkyl, $C_6$-$C_{12}$ aryl —OCOL$^2$R$^{50}$, —OCOR$^8$, and —CO$_2$R$^{60}$.

According to a particular embodiment, the compound of formula (II) is selected from the group comprising 1-pentene, 1-hexene, 1-heptene, 1-octene, 1-nonene, 1-decene, 1-undecene, 1-dodecene, 1-octadecene, 1-nonadecene, 1-tridecene, 1-tetradecene, 1-hexadecene, 1-octadecene, 3-butene-1,2-diol, 2-butene-1,4-diol, 2-bromo-2-butene, 1,4-dichloro-2-butene, 2,3-dimethyl-2-butene, 2-chloro-2-butene, 3,4-epoxy-1-butene, 1,1-diacetoxy-2-butene, 2,3-dibromo-2-butene-1,4-diol, 1-chloro-2-butene, 2-methyl-3-buten-2-ol, 3-buten-2-ol, 3-buten-2-one, 3-butenenitrile, 2,3-dimethyl-1,3-butadiene, 2-pentene, 2,4,4-trimethyl-2-pentene, 2-methyl-2-pentene, 3-ethyl-2-pentene, 5-o-tolyl-2-pentene, 4-methyl-2-pentene, 1-penten-3-ol, 3-methyl-3-penten-2-one, 4-methyl-3-penten-2-one, 2-hexene, 1,2-epoxy-5-hexene, 3,4-bis(4-hydroxyphenyl)-3-hexene, 5-hexen-2-one, 3-hexen-1-ol, cyclohexene, 3-cyclohexene-1-carboxaldehyde, 3-cyclohexene-1-methanol, 4-vinyl-1-cyclohexene, cyclohexene-1-carbonitrile, 1-cyclohexenylacetonitrile, p-mentha-1,8-diene (limonene), p-mentha-1,8-diene-7-ol, 1,4-cyclohexadiene, 1-isopropyl-4-methyl-1,3-cyclohexadiene (terpinene), p-benzoquinone, 6-methyl-5-hepten-2-one, bicyclo[2.2.1]hept-2-ene (norbornene), (1r, 5r)-2,6,6-trimethylbicyclo[3.1.1]hept-2-ene (pinene), 4-octene, 1,7-octadiene, 1-octen-3-yl acetate, cyclooctene, cyclooctadiene, 4-nonene, 10-undecen-1-ol, 7-tetradecene, 1,7-hexadecadiene, 1-amino-9-octadecene (oleylamine), ethyl acrylate, ethyl methacrylate, isoprene, myrcene, styrene, [alpha]-methylstyrene, vinyl acetate. For example, the compound of formula (II) is selected from the group comprising 1-octene, 3-butenenitrile, 2,3-dimethyl-1,3-butadiene, 2-hexene, 3-hexen-1-01, cyclohexene, 3-cyclohexene-1-carboxaldehyde, 1-cyclohexenylacetonitrile, p-mentha-1,8-diene (limonene), 1-isopropyl-4-methyl-1,3-cyclohexadiene (terpinene), 6-methyl-5-hepten-2-one, bicyclo[2.2.1]hept-2-ene (norbornene), (1r,5r)-2,6,6-trimethylbicyclo[3.1.1]hept-2-ene (pinene), 4-octene, cyclooctene, cyclooctadiene, 4-nonene, ethyl acrylate, ethyl methacrylate, isoprene, myrcene, styrene, [alpha]-methylstyrene. For example, the compound of formula (II) is selected from the group comprising 1-octene, 2-hexene, cyclohexene, 3-cyclohexene-1-carboxaldehyde, 1-cyclohexenylacetonitrile, p-mentha-1,8-diene (limonene), 6-methyl-5-hepten-2-one, bicyclo[2.2.1]hept-2-ene (norbornene), (1r,5r)-2,6,6-trimethylbicyclo[3.1.1]hept-2-ene (pinene), 4-octene, cyclooctene, cyclooctadiene, myrcene, styrene, and [alpha]-methylstyrene. For example, the compound of formula (II) is selected from the group comprising cyclohexene, 4-octene, cyclooctene, cyclooctadiene, myrcene, and styrene.

According to a particular embodiment, the compound of formula (II) is an unsaturated fatty body, preferably having the formula $R^{10}CH=CH-(CH_2)_u-CO_2R^{60}$ in which u is a whole number comprised between 2 and 11, preferably selected from 2, 3, 4, 5, 6, 7, 8, 9, or 10, and $R^{10}$ and $R^{60}$ have the same meaning as above.

The term "unsaturated fatty body" is used generically and it also designates unsaturated fatty acids per se, alone or in combination with saturated fatty acids, as well as their by-products, i.e. their $C_1$-$C_6$ ester alkylic, or glyceric form, as mono-, di- or triglycerides, or glycolic and/or mixtures thereof. The concept of "unsaturated fatty acid" within the meaning of the present description includes specifically the unsaturated compounds present in plant and animal oils and esters of fatty acids contained in these oils, as well as the corresponding fatty acids (non-sterified carboxylic acids). As examples of unsaturated fatty acids that may be used in the present invention, one may cite unsaturated fatty acids presenting a single double bond such as the following acids: linderic, myristoleic, palmitoleic, oleic, petroselenic, doeglic, gadoleic, erucic acids; unsaturated fatty acids presenting two double bonds such as linoleic acid; unsaturated fatty acids presenting 3 double bonds, such as linolenic acid; unsaturated fatty acids presenting more than 4 double bonds, such as isanic, stearodonic, arachidonic, chypanodonic acids; unsaturated fatty acids containing a hydroxyl group, such as ricinoleic acid, their $C_1$-$C_6$ alkylic ester, or their mono-, di- or triglyceride form, or a combination thereof. According to a particular embodiment, unsaturated fatty acids are selected from the group comprising undecylenic acid ($\Delta^9$ undecylenic), lauroleic acid ($\Delta^9$ dodecenoic), myristoleic acid ($\Delta^9$ tetradecenoic), palmitoleic acid ($\Delta^9$ hexacedecenoic), petroselinic acid ($\Delta^6$ octadecenoic), oleic acid ($\Delta^{9c}$ octadecenoic), elaidic ($\Delta^{9t}$ octadecenoic), vaccenic acid ($\Delta^{11t}$ octadecenoic), ricinoleic acid ($OH^{12}$,$\Delta^{9t}$ octadecenoic), linoleic acid ($\Delta^{9c}$,$\Delta^{12c}$ octadecadienoic), linolenic acid ($\Delta^{9c}$,$\Delta^{12c}$,$\Delta^{15c}$ octadecatrienoic), gondoic acid ($\Delta^{11}$ eicosenoic), erucic acid ($\Delta^{13}$ docosenoic), vernolic acid (12, 13-epoxy-9-cis-octadecenoic), coronoric acid (9,10-epoxy-12-cis-octadecenoic), alchornoic acid (14,15-epoxy-11-cis-eicosanoic) their $C_1$-$C_6$ alkylic ester or their mono-, di- or triglyceride form, or a combination thereof. According to a particular embodiment, unsaturated fatty acids are selected from the group comprising undecylenic acid ($\Delta^9$ undecylenic), lauroleic acid ($\Delta^9$ dodecenoic), myristoleic acid ($\Delta^9$ tetradecenoic), palmitoleic acid ($\Delta^9$ hexacedecenoic), oleic acid ($\Delta^{9c}$ octadecenoic), elaidic acid ($\Delta^{9t}$ octadecenoic), vaccenic acid ($\Delta^{11t}$ octadecenoic), ricinoleic acid ($OH^{12}$,$\Delta^{9t}$ octadecenoic), linoleic acid ($\Delta^{9c}$,$\Delta^{12c}$ octadecadienoic), linolenic acid ($\Delta^{9c}$,$\Delta^{2c}$,$\Delta^{5c}$ octadecatrienoic), erucic acid ($\Delta^{13}$ docosenoic), vernolic acid (12, 13-epoxy-9-cis-octadecenoic), their $C_1$-$C_6$ alkylic ester or their mono-, di- or triglyceride form, or a combination thereof. According to a particular embodiment, the unsaturated fatty acids are selected from the group comprising lauroleic acid ($\Delta^9$ dodecenoic), palmitoleic acid ($\Delta^9$ hexacedecenoic), oleic acid ($\Delta^{9c}$ octadecenoic), ricinoleic acid ($OH^{12}$, $\Delta^{9t}$ octadecenoic), linoleic acid ($\Delta^{9c}$,$\Delta^{12c}$, octadecadienoic), linolenic acid ($\Delta^{9c}$,$\Delta^{12c}$,$\Delta^{15c}$ octadecatrienoic), their $C_1$-$C_6$ alkalic ester, or their mono-, di- or triglyceride form, or a combination thereof. According to a particular embodiment, the unsaturated fatty acids are selected from the group comprising oleic acid ($\Delta^{9c}$ octadecenoic), linoleic acid ($\Delta^{9c}$, $\Delta^{12c}$ octadecadienoic), linolenic acid ($\Delta^{9c}$,$\Delta^{12c}$,$\Delta^{15c}$ octadecatrienoic), their $C_1$-$C_6$ alkylic ester or their mono-, di- or triglyceride form, or a combination thereof.

By way of examples of sources from plant origins, one may mention, among others, rapeseed, sunflower, peanut, olive, hazelnut, corn, soy, flaxseed, linseed, hemp, grapeseed, coconut, palm, cotton grain, bamboo, jojoba, sesame, castor oil, cilantro, safflower oil, tung oil. It is also possible to start with the esters corresponding to said acids, in particular methyl, ethyl or propyl esters, and one may also more specifically cite products of alcoholysis, more specifically of methanolysis, in particular of oils.

According to a particular embodiment, the aldehyde of formula (III) is selected from the group comprising formaldehyde, acetaldehyde, propanal, butyraldehyde, valeraldehyde, hexanal, heptanaldehyde, octanal, nonanaldehyde, decanal, undecanaldehyde, laurinaldehyde, tridecanaldehyde, isobutyraldehyde, lisovaleraldehyde, 2-methylbutyraldehyde, pivalaldehyde, 2-ethylbutaraldehyde, 2-ethylhexanaldehyde, isodecanaldehyde, acroleeine, crotonaldehyde, trans-2-hexen-1-al, trans,trans-2,4-hexadien-1-al, cis-4-heptenal, trans-2-nonen-1-al, cis-4-decenal, citronellal, hydroxycitronellal, 1-cyclohexene-1-carboxaldehyde, 3-cyclohexene-1-carboxaldehyde, benzaldehyde, 3-hydroxybenzaldehyde, 4-hydroxybenzaldehyde, 4-methyl-2-phenyl-2-pentenal, para-tertiarybutyl-alpha-methyl hydrocinnamic aldehyde, amyl cinnamic aldehyde, glyoxal, glutaraldehyde, furfuraldehyde, 3-(methylthio)propionaldehyde, 2-ethylacroleine, 3-methylcrotonaldehyde, 2-methyl-2-butenal, methyl 4-oxobutanoate, cinnamaldehyde, 3-dimethylaminoacroleine, cyclopentanecarboxaldehyde, 2,3,4,5,6-pentafluorobenzaldehyde, 4-bromo-2,6-difluorobenzaldehyde, 3,5-dibromobenzaldehyde, 3,5-dibromo-4-hydroxybenzaldehyde, 2,6-dinitrobenzaldehyde, 4-chlorobenzaldehyde, 2-chloro-4-hydroxybenzaldehyde, 4-fluorobenzaldehyde, 5-fluorosalicylaldehyde, 4-nitrobenzaldehyde, 4-hydroxy-3-nitrobenzaldehyde, 3,5-dihydroxybenzaldehyde, 2,4,6-trihydroxybenzaldehyde, 2-aminobenzaldehyde, 2,4-heptadienal, 2,2-dimethyl-4-pentenal, 2-cyanobenzaldehyde, isophtalaldehyde, terephthalaldehyde, 4-formylbenzoic acid, 5-formylsalicylic acid, o,m,p-tolualdehyde, phenylacetaldehyde, 2,4-dihydroxy-6-methylbenzaldehyde, 3-vinylbenzaldehyde, hydrocinnamaldehyde, 4-hydroxy-3,5-dimethylbenzaldehyde, mesitaldehyde, 2,4,6-trimethoxybenzaldehyde, 1-naphtaldehyde, biphenyl-4-carboxaldehyde, 3-phenoxybenzaldehyde, 4-(4-formylphenoxy)benzaldehyde, diphenylacetaldehyde, 9-anthracenecarboxaldehyde, 9-phenanthrenecarboxaldehyde, 5-(hydroxymethyl)furfural (HMF), and tris(4-formylphenyl)amine. For example, the aldehyde of formula (III) is selected from the group comprising acetaldehyde, propanal, butyraldehyde, valeraldehyde, hexanal, heptanaldehyde, octanal, nonanaldehyde, decanal, undecanaldehyde, laurinaldehyde, tridecanaldehyde, isobutyraldehyde, isovaleraldehyde, 2-methylbutyraldehyde, pivalaldehyde, 2-ethylbutaraldehyde, 2-ethylhexanaldehyde, isodecanaldehyde, acroleine, crotonaldehyde, trans-2-hexen-1-al, trans,trans-2,4-hexadien-1-al, cis-4-heptenal, trans-2-nonen-1-al, cis-4-decenal, citronellal, hydroxycitronellal, 1-cyclohexene-1-carboxaldehyde, 3-cyclohexene-1-carboxaldehyde, benzaldehyde, 3-hydroxybenzaldehyde, 4-hydroxybenzaldehyde, 4-methyl-2-phenyl-2-pentenal, glutaraldehyde, furfuraldehyde, 2-ethylacroleine, 3-methylcrotonaldehyde, 2-methyl-2-butenal, cinnamaldehyde, 2,3,4,5,6-pentafluorobenzaldehyde, 4-bromo-2,6-difluorobenzaldehyde, 3,5-dibromobenzaldehyde, 3,5-dibromo-4-hydroxybenzaldehyde, 2,6-dinitrobenzaldehyde, 4-chlorobenzaldehyde, 2-chloro-4-hydroxybenzaldehyde, 4-fluorobenzaldehyde, 5-fluorosalicylaldehyde, 4-nitrobenzaldehyde, 4-hydroxy-3-nitrobenzaldehyde, 3,5-dihydroxybenzaldehyde, 2,4,6-trihydroxybenzaldehyde, 2-aminobenzaldehyde, 1-cyclohexene-1-carboxaldehyde, 2-cyanobenzaldehyde, 4-formylbenzonitrile, terephthalaldehyde, 4-formylbenzoic acid, 2,4-dihydroxy-6-methylbenzaldehyde, 3-vinylbenzaldehyde, 1-naphtaldehyde, and 5-(hydroxymethyl)furfural (HMF). According to a preferred embodiment, the aldehyde of formula (III) is selected from the group comprising hexanal, decanal, citronellal, hydroxycitronellal, 3-cyclohexene-1-carboxaldehyde, benzaldehyde, 3-hydroxybenzaldehyde, 4-hydroxybenzaldehyde, furfuraldehyde, cinnamaldehyde, 3,5-dibromo-4-hydroxybenzaldehyde, 4-chlorobenzaldehyde2-chloro-4-hydroxybenzaldehyde, 4-fluorobenzaldehyde, 5-fluorosalicylaldehyde, 4-nitrobenzaldehyde, 4-hydroxy-3-nitrobenzaldehyde, 3,5-dihydroxybenzaldehyde, 2,4,6-trihydroxybenzaldehyde, 2-aminobenzaldehyde, 1-cyclohexene-1-carboxaldehyde, terephthalaldehyde, 4-formylbenzoic acid, 3-vinylbenzaldehyde, 1-naphtaldehyde, and 5-(hydroxymethyl)furfural (HMF). For example, the aldehyde of formula (III) is selected from the group comprising hexanal, decanal, citronellal, hydroxycitronellal, 3-cyclohexene-1-carboxaldehyde, benzaldehyde, 4-hydroxybenzaldehyde, cinnamaldehyde, 4-chlorobenzaldehyde, terephthalaldehyde, 4-formylbenzoic acid, and 5-(hydroxymethyl)furfural (HMF). For example, the aldehyde of formula (III) is selected from the group comprising hexanal, decanal, citronellal, hydroxycitronellal, 3-cyclohexene-1-carboxaldehyde, terephthalaldehyde, and benzaldehyde.

According to a particular embodiment, the compound of formula (III) is an aldehyde having the formula $R^{50}$—$(CR^{12}R^{11})_n$—CHO, in which each identical or different $R^{12}$ is selected from H or $C_1$-$C_6$ alkyl, each identical or different $R^{11}$ is selected from H, a halogen atom, —CHO, —OH, or $C_1$-$C_6$ alkyl, $C_6$-$C_{12}$ aryl, $C_6$-$C_{12}$ aryl$C_{1-6}$alkyl, $C_{1-6}$ alkyl$C_6$-$C_{12}$aryl, n is a whole number comprised between 1 and 20, and $R^{50}$ has the same meaning as stated above. According to a particular embodiment, n is selected from 1, 2, 3, 4, 5, 6, 7, 8, 9, 10, 11, 12, 13, 14, 15, 16, 17, 18, 19, or 20. According to a particular embodiment, $R^{12}$, identical or different, is selected from H or $C_1$-$C_4$ alkyl; each identical or different $R^{11}$ is selected from H or $C_1$-$C_4$ alkyl, $C_6$-$C_{12}$ aryl, $C_{1-4}$ alkyl$C_6$-$C_{12}$aryl. According to a particular embodiment, $R^{50}$ is selected from the group comprising Cl, F, I, Br, —OH, —SH, cyano, nitro, isocyanate, $C_1$-$C_4$ alkoxy, $C_2$-$C_{20}$ alkenyl, $C_2$-$C_{20}$ alkynyl, —$CO_2R^8$, epoxy, or —$NR^9{}_2$. For example, $R^{50}$ is selected from the group comprising Cl, F, I, Br, —OH, —SH, cyano, or nitro, preferably —OH, —SH, cyano or nitro, preferably —OH, —SH or cyano.

According to a particular embodiment, the aldehyde of formula (III) is used in an equimolar quantity, less than or more than the compound of formula (II).

According to a particular embodiment, the compound of formula (Ia) or (Ib) is prepared in situ (monotope synthesis process more commonly known by its English name of a "one-pot" reaction).

According to a particular embodiment, the reaction involves two successive steps comprising: epoxidation of the compound of formula (II) in the presence of molecular or atmospheric oxygen, and at least one aldehyde of formula (III) and optionally in the presence of at least one catalyst; and the opening of the epoxide (oxirane cycle) optionally in the presence of at least one catalyst, which catalyst may be the same as or different from that in the epoxidation step. The process allows the synthesis of multifunctional compounds in a single step through successive epoxidation and acylation reactions on unsaturated molecules.

One of the innovations of the invention resides in the use of an aldehyde that considerably increases the efficacy of the first step of the reaction and that, then, is used as an agent to open the oxirane cycle, since the aldehyde is transformed into an acid during the first step, as illustrated in Diagram 1. One of the innovations of the invention resides as well in the fact that the epoxide and the acid are only reaction intermediaries. They are generated in situ during the reaction. Another innovation is in the fact that during epoxidation, the opening reaction has already taken place.

Diagram 1: "One pot" reaction mechanism of an unsaturated molecule in the presence of an aldehyde according to a particular embodiment of the invention.

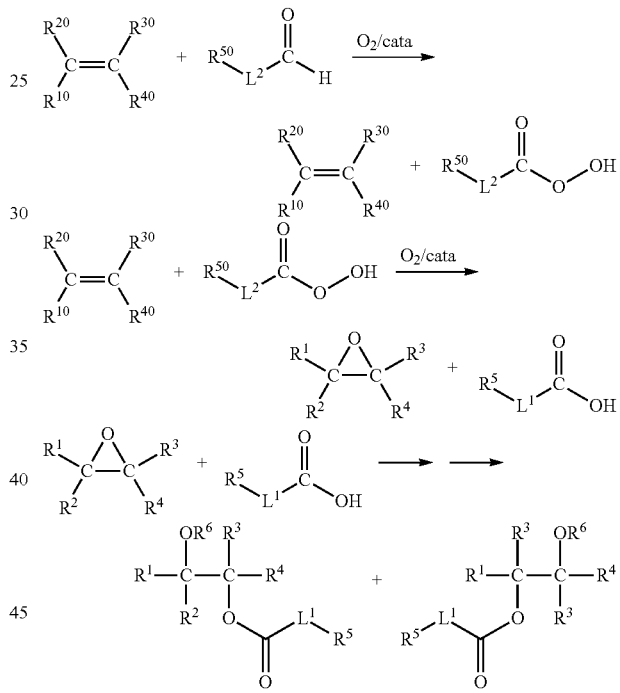

So, the opening agent is generated in situ by the transformation of aldehyde first into peracid, since it can either regenerate the catalyst or react with the unsaturation of the compound (II) to be transformed into an acid. During the second step, the opening of the epoxide, the acid function allows the opening and the grafting of the molecule onto the molecule of the epoxidated formula (II), by the creation of an ester link and a vicinal alcohol function, since the function at the end of the ester chain represents a new reaction center ($R^5$). According to a particular embodiment, the vicinal hydroxyl can also react, thus producing a compound of formula (Ia) and/or (Ib) in which $R^6$ is —CO-$L^1$-$R^5$.

According to a particular embodiment, the epoxidation step is carried out at a temperature of between 0 and 200° C., preferably between 20 and 150° C., preferably between 40 and 100° C., preferably between 50 and 80° C.

According to a particular embodiment, the epoxide opening step is carried out at a temperature of between 0 and 300°

C., preferably between 30 and 300° C., preferably between 30 and 250° C., preferably between 30 and 200° C., preferably between 30 and 170° C.

According to a particular embodiment, in the case of a "one pot" reaction, the epoxidation step and the epoxide opening step are carried out at the same temperature.

Preferably, the opening step is carried out in the presence of nitrogen. The presence of nitrogen allows secondary reactions to be minimized, such as lipidic oxidation in the case of the use of triglycerides or their derivatives (autoxidation, photo-oxidation).

According to a particular embodiment, the present process is carried out in the absence of a solvent. Advantageously, the process involves a one pot reaction of compounds of formula (II), using molecular or atmospheric oxygen as the oxidation agent in the presence of a solid catalyst, an aldehyde and in the absence of a solvent. Advantageously, the process involves a one pot reaction of unsaturated fatty bodies, using molecular or atmospheric oxygen as the oxidation agent in the presence of a solid catalyst, an aldehyde and in the absence of any solvent.

According to a particular embodiment, the solid catalyst is immobilized in a reactor, the compound of formula (II) and the aldehyde of formula (III) are sent into the reactor then the air or molecular oxygen is introduced, either by bubbling at atmospheric pressure, or under pressure. According to a particular embodiment, the environment is brought to the reaction temperature, preferably between 0 and 200° C., preferably between 20 and 150° C., preferably between 40 and 100° C., preferably between 50 and 80° C.

Samples may be taken regularly in order to gauge the progress of the epoxidation reaction. When it is complete, the air may be replaced by an inert gas, typically nitrogen, and the environment may be brought to a higher temperature, preferably between 30 and 200° C. in order to cause the epoxide opening reaction by the acid generated in situ. The catalyst may optionally be added in this step to catalyze the opening reaction. This catalyst may be solid, such as a zeolite, a hydrotalcite, an activated carbon a functionalized silica or a polymeric resin such as basic and/or acidic polymer resins such as those sold under the name Amberlyst® or Amberlite® or a combination thereof. This catalyst may be homogenous such as a mineral base (KOH, NaOH), a primary, secondary or tertiary amine (hexylamine, dihexylamine, trihexylamine) or a combination thereof.

Once the reaction is completed, the environment may be brought back to ambient temperature and taken from the reactor, which may again receive reagents without any specific treatment, since the catalyst may be reused without reactivation.

According to a particular embodiment, for example for industrial use, the process is carried out continuously or in two or several separate reactors.

The present invention relates also to the use of a process as described above for the preparation of polyhydroxylated polyesters.

The present invention also relates to compounds of formula (Ia), (Ib), (Ic) or (Id) that can be obtained through the process according to the invention, and their use, for example, in the preparation of polymers or biopolymers, in particular polyurethanes, of polyhydroxylated polyesters, bioplastics, surfactants, plasticizers or lubricants. According to a preferred embodiment, the invention also relates to the compounds of formula (Ia), (Ib), (Ic) or (Id) directly obtained via the process according to the invention, and their use, for example, in the preparation of polymers or biopolymers, in particular of polyurethanes, of polyhydroxylated polyesters, or bioplastics, of surfactants, plasticizers or lubricants. Preferably, the invention relates to the use of a compound of formula (Ia) or (Ib) directly obtained according to the process according to the invention, as a monomer for the preparation of polyurethane.

The invention also relates to a compound of formula (Ie) or (If), a stereoisomer thereof, or a mixture thereof,

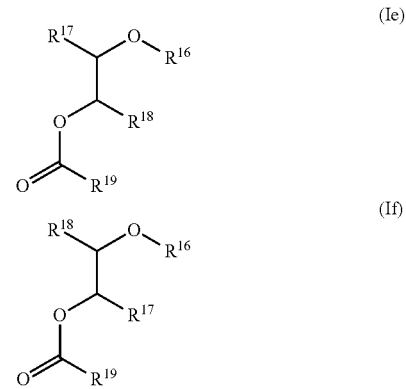

wherein:

$R^{16}$ is H or is selected from the group comprising —CO—$(CR^{21}R^{22})_q$—$R^{23}$, —CO—, $C_6$-$C_{12}$ aryl, and —CO—$C_5$-$C_{12}$ cycloalkenyl, with each group being optionally substituted by one or several groups, either identical or different, selected from the group comprising a halogen atom, —OH, —OCOR$^{19}$, —CO$_2$R$^{24}$, and $C_1$-$C_6$ alkyl; preferably $R^{16}$ is H or is selected from the group comprising —CO—$(CR^{21}R^{22})_q$—$R^{23}$, —CO—$C_6$-$C_{10}$ aryl, and —CO—$C_5$-$C_{10}$ cycloalkenyl, with each group being optionally substituted by one or several groups, either identical or different, selected from the group comprising a halogen atom, —OH, —OCOR$^{19}$, —CO$_2$R$^{24}$, and $C_1$-$C_6$ alkyl; preferably $R^{16}$ is H or is selected from the group comprising —CO—$(CR^{21}R^{22})_q$R$^{23}$, —CO—$C_6$ aryl, and $C_5$-$C_8$ cycloalkenyl, with each group being optionally substituted by one or several groups, either identical or different, selected from the group comprising a halogen atom, —OH, —OCOR$^{19}$, —CO$_2$R$^{24}$, and $C_1$-$C_4$ alkyl;

$R^{17}$ is selected from the group comprising a $C_2$-$C_{20}$ alkyl and a $C_2$-$C_{20}$ alkenyl, with each group being optionally substituted by one or several identical or different groups, selected from a $C_1$-$C_6$ alkyl, a $C_6$ aryl, —OR$^{16}$, or —CO$_2$R$^{24}$; preferably $R^{17}$ is selected from the group comprising a $C_2$-$C_{12}$ and a $C_2$-$C_{20}$ alkenyl, with each group being optionally substituted by 1, 2, 3 or 4 groups, either identical or different, selected from a $C_1$-$C_6$ alkyl, a $C_6$ aryl, —OR$^{16}$, or —CO$_2$R$^{24}$; preferably $R^{17}$ is selected from the group comprising a $C_2$-$C_{12}$ alkyl and a $C_2$-$C_{20}$ alkenyl, with each group being optionally substituted by 1, 2, 3 or 4 groups, either identical or different, selected from a $C_1$-$C_6$ alkyl, —OR$^{16}$, or —CO$_2$R$^{24}$; $R^{17}$ is preferably a $C_2$-$C_{10}$ alkyl optionally substituted by 1, 2, or 3 groups, that is a $C_2$-$C_{10}$ alkyl, optionally substituted by 1, 2, or 3 identical or different groups, selected from a $C_1$-$C_4$ alkyl, or —CO$_2$R$^{24}$;

$R^{18}$ is H or is selected from the group comprising a $C_2$-$C_{20}$ alkyl and a $C_2$-$C_{20}$ alkenyl, with each group being optionally substituted by one or several identical or different groups, selected from a $C_1$-$C_6$ alkyl, a $C_6$ aryl, —OR$^{16}$, or —CO$_2$R$^{24}$; preferably $R^{18}$ is H or is selected from the group comprising a $C_2$-$C_{12}$ and a $C_2$-$C_{20}$ alkenyl, with each group being optionally substituted by 1, 2, 3 or 4 groups, either identical or different, selected from a $C_1$-$C_6$ alkyl, a $C_6$ aryl, —OR$^{16}$, or —$CO_2R^{24}$; preferably $R^{18}$ is H or is selected from the group comprising a $C_2$-$C_{12}$ and a $C_2$-$C_{20}$ alkenyl, with each group being optionally substituted by 1, 2, 3 or 4 groups, either identical or different, selected from a $C_1$-$C_6$ alkyl, —$OR^{16}$, or —$CO_2R^{24}$; preferably $R^{18}$ is H or a $C_2$-$C_{10}$ alkyl optionally substituted by 1, 2, or 3 identical or different groups, selected from a $C_1$-$C_4$ alkyl or —$CO_2R^{24}$; or $R^{17}$ and $R^{18}$ may, with the carbons to which they are bound, form a group selected from a $C_5$-$C_{12}$ cycloalkyl or $C_5$-$C_{12}$ cycloalkenyl, with each group being optionally substituted by one or several groups, either identical or different, selected from the group comprising a halogen atom, —$OR^{16}$, —$OCOR^{19}$, —$CO_2R^{24}$, and $C_1$-$C_6$ alkyl; preferably $R^{17}$ and $R^{18}$ may, with the carbons to which they are bound, form a group selected from a $C_5$-$C_{10}$ cycloalkyl or a $C_5$-$C_{10}$ cycloalkenyl, with each group being optionally substituted by 1, 2, 3, or 4 groups, either identical or different, selected from the group comprising a halogen atom, —$OR^{16}$, —$OCOR^{19}$, —$CO_2R^{24}$, and $C_1$-$C_6$ alkyl; preferably $R^{17}$ and $R^{18}$ may, with the carbons to which they are bound, form a group selected from a $C_5$-$C_8$ cycloalkyl or $C_5$-$C_8$ cycloalkenyl, with each group being optionally substituted by 1, 2 or 3 groups, either identical or different, selected from the group comprising —OH, —$OCOR^{19}$, —$CO_2R^{24}$, and $C_1$-$C_4$ alkyl;

$R^{19}$ is selected from the group comprising -$(CR^{21}R^{22})_q$—$R^{23}$, a $C_6$-$C_{12}$ aryl, and a $C_5$-$C_{12}$ cycloalkenyl, with each group being optionally substituted by one or several groups, either identical or different, selected from the group comprising a halogen atom, —OH, —$OCOR^{19}$, —$CO_2R^{24}$, and $C_1$-$C_6$ alkyl; preferably $R^{19}$ is selected from the group comprising —$(CR^{21}R^{22})_q$—$R^{23}$, a $C_6$-$C_{10}$ aryl, and a $C_5$-$C_{10}$, cycloalkenyl, with each group being optionally substituted by 1, 2, 3 or 4 groups, that are identical or different, selected from the group comprising a halogen atom, —OH, —$OCOR^{19}$, —$CO_2R^{24}$, and $C_1$-$C_6$ alkyl; preferably $R^{19}$ is selected from the group comprising —$(CR^{21}R^{22})_q$—$R^{23}$, a $C_6$ aryl, and a $C_5$-$C_8$ cycloalkenyl, with each group being optionally substituted by 1, 2, 3, or 4 groups, either identical or different, selected from the group comprising a halogen atom, —OH, —OCOR19, —CO2R24, and $C_1$-$C_4$ alkyl;

q is a whole number comprises between 3 and 12; preferably q is a whole number comprised between 4 and 12, for example q may be 4, 5, 6, 7, 8, 9, 10, 11 or 12;

each identical or different $R^{21}$ is selected from H or a $C_1$-$C_6$ alkyl; preferably each identical or different $R^{21}$ is selected from H or a $C_1$-$C_4$ alkyl;

each identical or different $R^{22}$ is selected from H or a $C_1$-$C_6$ alkyl; preferably each identical or different $R^{22}$ is selected from H or a $C_1$-$C_4$ alkyl;

$R^{23}$ is H or —OH, or is selected from the group comprising a $C_1$-$C_6$ alkyl and a $C_6$-$C_{12}$ aryl, with each group being optionally substituted by one or several groups, either identical or different, selected from the group comprising a halogen atom, —OH, —$OCOR^{19}$, —$CO_2R^{24}$, and $C_1$-$C_6$ alkyl; preferably $R^{23}$ is selected from H, —OH or a $C_1$-$C_4$ alkyl optionally substituted by 1, 2 or 3 groups, either identical or different, selected from the group comprising a halogen atom, —OH, —$OCOR^{19}$, —$CO_2R^{24}$, and $C_1$-$C_6$ alkyl;

$R^{24}$ is H or a $C_1$-$C_6$ alkyl optionally substituted by one or several groups, either identical or different, selected from the group comprising —OH, —O—$COR^{25}$, and $C_1$-$C_6$ alkyl; preferably $R^{24}$ is H or a $C_1$-$C_4$ alkyl, optionally substituted by 1, 2, or 3 identical or different groups, selected from —OH, —O—$COR^{25}$, or $C_1$-$C_4$; alkyl; preferably $R^{24}$ is H or a $C_1$-$C_4$ alkyl optionally substituted by 1, 2, or 3 identical or different groups, selected from —OH, —O—$COR^{25}$, or $C_1$-$C_4$ alkyl;

$R^{25}$ is selected from the group comprising $C_2$-$C_{20}$ alkyl; and $C_2$-$C_{20}$ alkenyl, with each group being optionally substituted by one or several groups, either identical or different, selected from the group comprising —OH, epoxy, —$OR^{16}$, and —$OCOR^{19}$; preferably $R^{25}$ is selected from the group comprising $C_2$-$C_{20}$ alkyl and $C_2$-$C_{20}$ alkenyl, with each group being optionally substituted by 1, 2 or 3 groups, either identical or different, selected from the group comprising —OH, epoxy, —$OR^{16}$, and —$OCOR^{19}$.

The invention also relates to a compound having formula (Ie) or (If), a stereoisomer thereof, a mixture thereof, an oligomer and/or a polymer thereof.

According to a preferred embodiment, the invention relates to a compound having formula (Ie) or (If), an oligomer and/or a polymer thereof, wherein $R^{16}$ is H or is selected from the group comprising —CO—$(CR^{21}R^{22})_q$—$R^{23}$, —CO—$C_6$-$C_{12}$ aryl, and —CO—$C_5$-$C_{12}$ cycloalkenyl, with each group being optionally substituted by one or several groups, either identical or different, selected from the group comprising a halogen atom, —OH, —$OCOR^{19}$, —$CO_2R^{24}$, and $C_1$-$C_6$ alkyl;

$R^{17}$ is a $C_3$-$C_{20}$ alkyl optionally substituted by one or several identical or different groups, selected from a $C_1$-$C_6$ alkyl, —$OR^{16}$, or —$CO_2R^{24}$; preferably $R^{17}$ is a $C_3$-$C_{12}$ alkyl, optionally substituted by one or several identical or different groups, selected from a $C_1$-$C_6$ alkyl, —$OR^{16}$, or —$CO_2R^{24}$;

$R^{18}$ is H or a $C_3$-$C_{20}$ alkyl optionally substituted by one or several identical or different groups, selected from a $C_1$-$C_6$ alkyl —$OR^{16}$, or —$CO_2R^{24}$; preferably $R^{18}$ is H or a $C_3$-$C_{12}$ alkyl optionally substituted by one or several identical or different groups, selected from a $C_1$-$C_6$ alkyl, —$OR^{16}$, or —$CO_2R^{24}$; or $R^{17}$ and $R^{18}$ may, with the carbons to which they are bound, form a group selected from a $C_5$-$C_{12}$ cycloalkyl or a $C_5$-$C_{12}$ cycloalkenyl with each group being optionally substituted by one or several groups, either identical or different, selected from the group comprising a halogen atom, —$OR^{16}$, —$OCOR^{19}$, —$CO_2R^{24}$, and $C_1$-$C_6$ alkyl; or $R^{17}$ and $R^{18}$ may preferably, with the carbons to which they are bound, form a group selected from a $C_5$-$C_{12}$ cycloalkyl or a $C_5$-$C_{12}$ cycloalkenyl, with each group being optionally substituted by 1, 2, 3 or 4 identical or different groups, selected from —OH, —$OCOR^{19}$, —$CO_2R^{24}$, or $C_1$-$C_6$ alkyl;

$R^{19}$ is selected from the group comprising —$(CR^{21}R^{22})_q$—$R^{23}$, a $C_6$-$C_{12}$ aryl, and a $C_5$-$C_{12}$ cycloalkenyl, with each group being optionally substituted by one or several groups, either identical or different, selected from the group comprising a halogen atom, —OH, —$OCOR^{19}$, —$CO_2R^{24}$, and $C_1$-$C_6$ alkyl; preferably $R^{19}$ is selected from the group comprising —$(CR^{21}R^{22})_q$—$R^{23}$, a $C_6$ aryl, and a $C_5$-$C_{12}$ cycloalkenyl, with each group being optionally substituted by one or several groups, either identical or different, selected from the group comprising —OH, —$OCOR^{19}$, —$CO_2R^{24}$, and $C_1$-$C_6$ alkyl;

q is a whole number comprised between 3 and 12; for example q is 3, 4, 5, 6, 7, 8, 9, 10 or 11;

each identical or different $R^{21}$ is selected from H or a $C_1$-$C_6$ alkyl;

each identical or different $R^{22}$ is selected from H or a $C_1$-$C_6$ alkyl;

$R^{23}$ is H or —OH, or is selected from the group comprising a $C_1$-$C_6$ alkyl and a $C_6$-$C_{12}$ aryl, with each group being optionally substituted by one or several groups, either identical or different, selected from the group comprising a halogen atom, —OH, —$OCOR^{19}$, —$CO_2R^{24}$, and $C_1$-$C_6$ alkyl;

$R^{24}$ is H or a $C_1$-$C_6$ alkyl optionally substituted by one or several identical or different groups, selected from —OH, —O—$COR^{25}$, or $C_1$-$C_6$ alkyl; and $R^{25}$ is selected from the group comprising $C_2$-$C_{20}$ alkyl, and $C_2$-$C_{20}$ alkenyl, with each group being optionally substituted by one or several groups, either identical or different, selected from the group comprising —OH, epoxy, —$OR^{16}$, and —$OCOR^{19}$;

provided that the compound is not methyl 9-(hexanoyloxy)-10-hydroxyoctadecanoate, methyl 10-(hexanoyloxy)-9-hydroxyoctadecanoate, the octanoic ester of methyl hydroxy-oleate, the 2-ethyl-hexyl ester of methyl hydroxy-oleate, methyl hydroxybenzoyloxy-octadodecaneate, 1,2-heptanediol dicaproate and 1,2-octanediol dicaproate.

According to a preferred embodiment, the invention relates to a compound of formula (Ie) or (If), wherein: $R^{16}$ is H; and $R^{17}$ is selected from the group comprising a $C_2$-$C_{20}$ alkyl and a $C_2$-$C_{20}$ alkenyl, with each group being optionally substituted by one or several identical or different groups, selected from a $C_1$-$C_6$ alkyl, a $C_6$ aryl, or —$OR^{16}$, preferably $R^{17}$ is selected from the group comprising a $C_2$-$C_{12}$ and a $C_2$-$C_{20}$ alkenyl, with each group being optionally substituted by 1, 2, 3 or 4 groups, either identical or different, selected from a $C_1$-$C_6$ alkyl, or a $C_6$ aryl, —$OR^{16}$; preferably $R^{17}$ is selected from the group comprising a $C_2$-$C_{12}$ and a $C_2$-$C_{20}$ alkenyl, with each group being optionally substituted by 1, 2, 3 or 4 groups, either identical or different, selected from a $C_1$-$C_6$ alkyl, or —$OR^{16}$; preferably $R^{17}$ is a $C_2$-$C_{10}$ alkyl, optionally substituted by 1, 2, or 3 identical or different groups, selected from a $C_1$-$C_4$ alkyl;

$R^{18}$ is H or is selected from the group comprising a $C_2$-$C_{20}$ alkyl and a $C_2$-$C_{20}$ alkenyl, with each group being optionally substituted by one or several identical or different groups, selected from a $C_1$-$C_6$ alkyl, a $C_6$, aryl or —$OR^{16}$; preferably $R^{18}$ is H or is selected from the group comprising a $C_2$-$C_{12}$ and a $C_2$-$C_{20}$ alkenyl, with each group being optionally substituted by 1, 2, 3 or 4 groups, either identical or different, selected from a $C_1$-$C_6$ alkyl, a $C_6$ aryl, or —$OR^{16}$, preferably $R^{18}$ is H or is selected from the group comprising a $C_2$-$C_{12}$ and a $C_2$-$C_{20}$ alkenyl, with each group being optionally substituted by 1, 2, 3 or 4 groups, either identical or different, selected from a $C_1$-$C_6$ alkyl, or —$OR^{16}$; preferably $R^{18}$ is H or a $C_2$-$C_{10}$ alkyl, optionally substituted by 1, 2, or 3 identical or different groups, selected from a $C_1$-$C_4$ alkyl; or $R^{16}$ is H or is selected from the group comprising —CO—$(CR^{21}R^{22})_q$—$R^{23}$, —CO—$C_6$-$C_{12}$ aryl, and —CO—$C_5$-$C_{12}$ cycloalkenyl, with each group being optionally substituted by one or several groups, either identical or different, selected from the group comprising a halogen atom, —OH, —$OCOR^{19}$, —$CO_2R^{24}$, and $C_1$-$C_6$ alkyl; and $R^{17}$ and $R^{18}$ form with the carbons to which they are bound a group selected from a $C_5$-$C_{12}$ cycloalkyl or a $C_5$-$C_{12}$ cycloalkenyl, with each group being optionally substituted by one or several groups, either identical or different, selected from the group comprising a halogen atom, —$OR^{16}$, —$OCOR^{19}$, —$CO_2R^{24}$, and $C_1$-$C_6$ alkyl; or $R^{17}$ and $R^{18}$ may preferably, with the carbons to which they are bound, form a group selected from a $C_5$-$C_{10}$ cycloalkyl or a $C_5$-$C_{10}$ cycloalkenyl, with each group being optionally substituted by 1, 2, 3, or 4 groups, either identical or different, selected from the group comprising a halogen atom, —$OR^{16}$—$OCOR^{19}$, —$CO_2R^{24}$, and $C_1$-$C_6$ alkyl; or $R^{17}$ and $R^{18}$ may preferably, with the carbons to which they are bound, form a group selected from a $C_5$-$C_8$ cycloalkyl or a $C_5$-$C_8$ cycloalkenyl, with each group being optionally substituted by 1, 2 or 3 groups, either identical or different, selected from the group comprising —OH, —$OCOR^{19}$, —$CO_2R^{24}$, and $C_1$-$C_4$ alkyl;

$R^{19}$ is selected from the group comprising —$(CR^{21}R^{22})_q$—$R^{23}$, a $C_6$-$C_{12}$ aryl, and a $C_5$-$C_{12}$ cycloalkenyl, with each group being optionally substituted by one or several groups, either identical or different, selected from the group comprising a halogen atom, —OH, —$OCOR^{19}$, —$CO_2R^{24}$, and $C_1$-$C_6$ alkyl; preferably $R^{19}$ is selected from the group comprising —$(CR^{21}R^{22})_q$—$R^{23}$, a $C_6$-$C_{10}$ aryl, and a $C_5$-$C_{10}$ cycloalkenyl, with each group being optionally substituted by 1, 2, 3, or 4 identical or different groups, selected from the group comprising a halogen atom, —OH, —$OCOR^{19}$, —$CO_2R^{24}$, and $C_1$-$C_6$ alkyl; preferably $R^{19}$ is selected from the group comprising —$(CR^{21}R^{22})_q$—$R^{23}$, a $C_6$ aryl, and a $C_5$-$C_8$ cycloalkenyl, with each group being optionally substituted by 1, 2, or 3 identical or different groups, selected from the group comprising a halogen atom, —OH, —$OCOR^{19}$, —$CO_2R^{24}$, and $C_1$-$C_4$ alkyl;

q is a whole number comprised between 3 and 12; preferably q is a whole number comprised between 4 and 12, for example q may be 4, 5, 6, 7, 8, 9, 10, 11 or 12;

each identical or different $R^{21}$ is selected from H or a $C_1$-$C_6$ alkyl; preferably each identical or different $R^{21}$ is selected from H or a $C_1$-$C_4$ alkyl;

each identical or different $R^{22}$ is selected from H or a $C_1$-$C_6$ alkyl; preferably each identical or different $R^{22}$ is selected from H or a $C_1$-$C_4$ alkyl;

$R^{23}$ is H or —OH, or is selected from the group comprising a $C_1$-$C_6$ alkyl and a $C_6$-$C_{12}$ aryl, with each group being optionally substituted by one or several groups, either identical or different, selected from the group comprising a halogen atom, —OH, —$OCOR^{19}$, —$CO_2R^{24}$, and $C_1$-$C_6$ alkyl; preferably $R^{23}$ is selected from H, —OH or a $C_1$-$C_4$ alkyl optionally substituted by 1, 2 or 3 groups, either identical or different, selected from the group comprising a halogen atom, —OH, —$OCOR^{19}$, —$CO_2R^{24}$, and $C_1$-$C_6$ alkyl;

$R^{24}$ is H or a $C_1$-$C_6$ alkyl optionally substituted by one or several groups, either identical or different, selected from the group comprising —OH, —O—$COR^{25}$, and $C_1$-$C_6$ alkyl; preferably $R^{24}$ is H or a $C_1$-$C_4$ alkyl, optionally substituted by 1, 2, or 3 identical or different groups, selected from —OH, —O—$COR^{25}$, or $C_1$-$C_4$ alkyl; preferably $R^{24}$ is H or a $C_1$-$C_4$ alkyl optionally substituted by 1, 2, or 3 identical or different groups, selected from —OH, —O—$COR^{25}$, or $C_1$-$C_4$ alkyl;

$R^{25}$ is selected from the group comprising $C_2$-$C_{20}$ alkyl; and $C_2$-$C_{20}$ alkenyl, with each group being optionally substituted by one or several groups, either identical or different, selected from the group comprising —OH, epoxy, —$OR^{16}$, and —$OCOR^{19}$; preferably $R^{25}$ is selected from the group comprising $C_2$-$C_{20}$ alkyl, and $C_2$-$C_{20}$ alkenyl, with each group being optionally substituted by 1, 2 or 3 groups, either identical or different, selected from the group comprising —OH, epoxy, —$OR^{16}$, and —$OCOR^{19}$.

According to a preferred embodiment, the invention relates to a compound having formula (Ie) or (If), wherein:

$R^{16}$ is H or is selected from the group comprising —CO—$(CR^{21}R^{22})_q$—$R^{23}$, —CO—$C_6$-$C_{12}$ aryl, and —CO—$C_5$-$C_{12}$ cycloalkenyl, with each group being optionally substituted by one or several groups, either identical or different, selected from the group comprising a halogen atom, —OH, —$OCOR^{19}$, —$CO_2R^{24}$, and $C_1$-$C_6$ alkyl;

$R^{17}$ is a $C_3$-$C_{20}$ alkyl optionally substituted by one or several identical or different groups, selected from a $C_1$-$C_6$ alkyl, —$OR^{16}$, or —$CO_2R^{24}$; preferably $R^{17}$ is a $C_3$-$C_{12}$ alkyl, optionally substituted by one or several identical or different groups, selected from a $C_1$-$C_6$ alkyl, —$OR^{16}$, or —$CO_2R^{24}$;

$R^{18}$ is H or a $C_3$-$C_{20}$ alkyl optionally substituted by one or several identical or different groups, selected from a $C_1$-$C_6$ alkyl, —$OR^{16}$, or —$CO_2R^{24}$; preferably $R^{18}$ is H or a $C_3$-$C_{12}$ alkyl optionally substituted by one or several identical or different groups, selected from a $C_1$-$C_6$ alkyl, —$OR^{16}$, or —$CO_2R^{24}$;

or $R^{17}$ and $R^{18}$ may, with the carbons to which they are bound, form a group selected from a $C_5$-$C_{12}$ cycloalkyl or a $C_5$-$C_{12}$ cycloalkenyl, with each group being optionally substituted by one or several groups, either identical or different, selected from the group comprising a halogen atom, —$OR^{16}$, —$OCOR^{19}$, —$CO_2R^{24}$, and $C_1$-$C_6$ alkyl; or $R^{17}$ and $R^{18}$ may preferably, with the carbons to which they are bound, form a group selected from a $C_5$-$C_{12}$ cycloalkyl or a $C_5$-$C_{12}$ cycloalkenyl, with each group being optionally substituted by 1, 2, 3 or 4 groups, either identical or different, selected from —OH, —$OCOR^{19}$, —$CO_2R^{24}$, or $C_1$-$C_6$ alkyl;

$R^{19}$ is selected from the group comprising —$(CR^{21}R^{22})_q$—$R^{23}$, a $C_6$-$C_{12}$ aryl, and a $C_5$-$C_{12}$ cycloalkenyl, with each group being optionally substituted by one or several groups, either identical or different, selected from the group comprising a halogen atom, —OH, —$OCOR^{19}$, —$CO_2R^{24}$, and $C_1$-$C_6$ alkyl; preferably $R^{19}$ is selected from the group comprising —$(CR^{21}R^{22})_q$—$R^{23}$, a $C_6$ aryl, and a $C_5$-$C_{12}$ cycloalkenyl, with each group being optionally substituted by one or several groups, either identical or different, selected from the group comprising —OH, —$OCOR^{19}$, —$CO_2R^{24}$, and $C_1$-$C_6$ alkyl;

q is a whole number comprised between 3 and 12; for example q is 3, 4, 5, 6, 7, 8, 9, 10 or 11;

each identical or different $R^{21}$ is selected from H or a $C_1$-$C_6$ alkyl;

each identical or different $R^{22}$ is selected from H or a $C_1$-$C_6$ alkyl;

$R^{23}$ is H or —OH, or is selected from the group comprising a $C_1$-$C_6$ alkyl and a $C_6$-$C_{12}$ aryl, with each group being optionally substituted by one or several groups, either identical or different, selected from the group comprising a halogen atom, —OH, —$OCOR^{19}$, —$CO_2R^{24}$, and $C_1$-$C_6$ alkyl;

$R^{24}$ is H or a $C_1$-$C_6$ alkyl optionally substituted by one or several groups, either identical or different, selected from —OH, —O—$COR^{25}$, or $C_1$-$C_6$ alkyl; and $R^{25}$ is selected from the group comprising $C_2$-$C_{20}$ alkyl, and $C_2$-$C_{20}$ alkenyl, with each group being optionally substituted by one or several groups, either identical or different, selected from the group comprising —OH, epoxy, —$OR^{16}$, and —$OCOR^{19}$.

The present invention also relates to an oligomer and/or a polymer of compounds of formula (Ie) or (If), such as the compounds of formula (Ig) or (Ih),

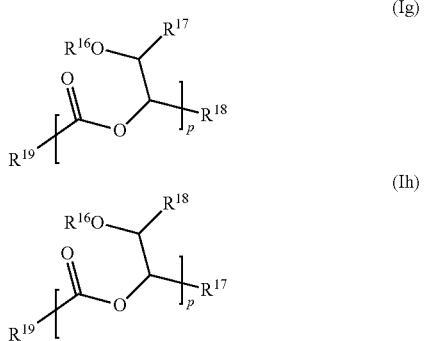

in which $R^{16}$, $R^{17}$, $R^{18}$, $R^{19}$, are as described above and p is a whole number comprised between 1 and 10,000, preferably p is a whole number comprised between 1 and 1,000, for example p is a whole number comprised between 1 and 100.

According to a particular embodiment, the present invention relates to a compound of formula (Ie) or (If) selected from the group comprising 9-hydroxy-10-(7-hydroxy-3,7-dimethyloctanoyloxy)methyl octadecanoate, 10-hydroxy-9-(7-hydroxy-3,7-dimethyloctanoyloxy)methyl octadecanoate, methyl 9-(decanoyloxy)-10-hydroxyoctadecanoate; methyl 10-(decanoyloxy)-9-hydroxyoctadecanoate, 2-hydroxyoctyl hexanoate, 1-hydroxyoctan-2-yl hexanoate; 5-hydroxyoctan-4-yl hexanoate; octane-4,5-diyl dihexanoate; 2-hydroxycyclooctyl hexanoate; cyclooctane-1,2-diyl dihexanoate; 4-formyl-2-hydroxycyclohexyl cyclohex-3-enecarboxylate; 5-formyl-2-hydroxycyclohexyl; 7-oxa-bicyclo[4.1.0]heptane-3-carboxylate; 4-(cyclohex-3-enecarbonyloxy)-3-hydroxycyclohexanecarboxylic acid; and 3-(7-oxa-bicyclo[4.1.0]heptane-3-carbonyloxy)-4-hydroxycyclohexanecarboxylic acid.

According to a particular embodiment, the present invention relates to a compound of formula (Ia), or (Ib), that may be obtained through the present process, having formula (Ie) or (If).

According to a particular embodiment, the compounds of formula (Ia), (Ib), (Ic), (Id), (Ie), (If), (Ig) or (Ih) may be used for the preparation of polymers, biopolymers, surfactants, plasticizers or lubricants, or for the preparation of polyurethane.

According to a preferred embodiment, the present invention concerns the use of a compound of formula (Ia), (Ib), (Ic), (Id), (Ie), (If), (Ig) or (Ih), or of methyl 9-(hexanoyloxy)-10-hydroxyoctadecanoate, methyl 10-(hexanoyloxy)-9-hydroxyoctadecanoate, the octanoic ester of methyl hydroxyoleate, the 2-ethyl-hexyl ester of methyl hydroxyoleate, methyl hydroxybenzoyloxy-octadodecaneate, 1,2-heptanediol dicaproate and 1,2-octanediol dicaproate; as a monomer for the preparation of polyurethane.

Polyurethane is understood to mean polymers resulting primarily from the reaction of compounds of formula (Ia), (Ib), (Ic), (Id), (Ie), (If), (Ig) or (Ih) or a combination thereof with isocyanates. Polyurethane is also understood to mean polymers resulting from the reaction of compounds of formula (Ia), (Ib), (Ie), (Id), (Ie), (If), (Ig) or (Ih) or a combination thereof with isocyanates that contain, aside from urethane functions, other types of functions, in particular triisocyanate cycles formed by the trimerization of isocyanates.

The invention also relates to a formulation comprising:
at least one compound of formula (Ia), (Ib), (Ic), (Id), (Ie), (If), (Ig) or (Ih) or a combination thereof, and
at least one isocyanate.

These formulations may be used to prepare polyurethanes, in particular thermoplastic or thermohardened polyurethanes. The formulations according to the invention may also include one or several polyols traditionally used to prepare polyurethanes. Polyether-polyols and polyester-polyols may also be cited.

All isocyanates traditionally used to manufacture polyurethanes may be implemented in the use or formulations according to the invention. Preferably, the isocyanate is a polyisocyanate. The polyisocyanate used may be selected from aliphatic, aromatic, cycloaliphatic and those isocyanates that contain an isocyanurate cycle in their molecule; having at least two isocyanate functions in their molecule, likely to react with one or several hydroxyl functions of a compound of formula (Ia), (Ib), (Ic), (Id), (Ie), (If), (Ig) or (Ih) to form a three-dimensional polyurethane network causing the reticulation of the formulation.

In regards to polyisocyanates well suited in the context of the present invention, one can specifically cite: hexamethylenediisocyanate (HMDI, HDI, or 1,6-diisocyanatohexane), diphenylmethanediisocyanate (MDI) in the form of its 2,4',2,2' and 4,4' isomers or a mixture thereof, toluene diisocyanate (TDI), isophoronediisocyanate (IPDI), dicyclohexylmethanediisocyanate (DCI); naphthalene 1,5-diisocyanate (NDI), p-phenylene diisocyanate (PPDI), 3,3'-dimethyldiphenyl-4,4'-diisocyanate (DDDI), or 4,4'-dibenzyl diisocyanate (DBDI), or a mixture thereof.

According to a preferred embodiment, compounds of formula (Ia), (Ib), (Ic), (Id), (Ie), (If), (Ig) or (Ih) originate from the plant world. The end products that use these polymers are therefore advantageously polymers that originate from the plant world. The product of the reaction, preferably a "one pot" reaction, mentioned above, on a vegetable oil, is a functionalized molecule, so that it may be used as raw material for the fabrication of plastic material. This molecule is classified as a synthon (building block). Various types of plastics (bioplastics) may be envisaged depending on the nature of the function provided by the synthesis procedure.

The following examples are given for purposes of illustration and are non-limiting of this invention, and are subject to variants easily accessible to a person skilled in the art.

EXAMPLES

Example 1

This example presents a comparison of various catalysts consisting of a metal deposited on a silicon media. All catalysts were prepared using ionic exchange starting from a colloidal silica stabilized with ammonium ions and metal chloride corresponding to the active species. These items were tested in regards to the functionalization reaction of methyl oleate by hydroxycitronellal which lead to the synthesis of 9-hydroxy-10-(7-hydroxy-3,7-dimethyloctanoyloxy) methyl octadecanoate and of 10-hydroxy-9-(7-hydroxy-3,7-dimethyloctanoyloxy)methyl octadecanoate as illustrated in Diagram 2.

Diagram 2: Functionalization of methyl oleate in the presence of hydroxycitronellal by successive epoxidation and acylation.

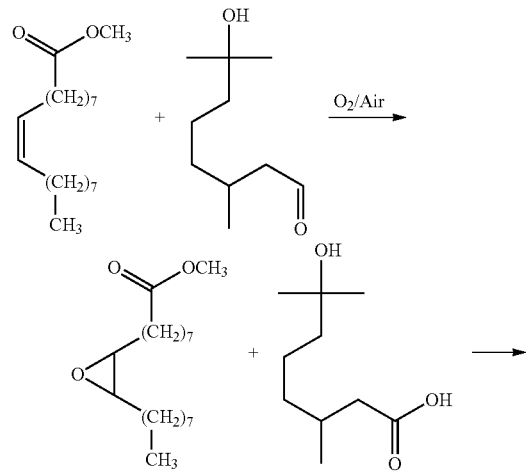

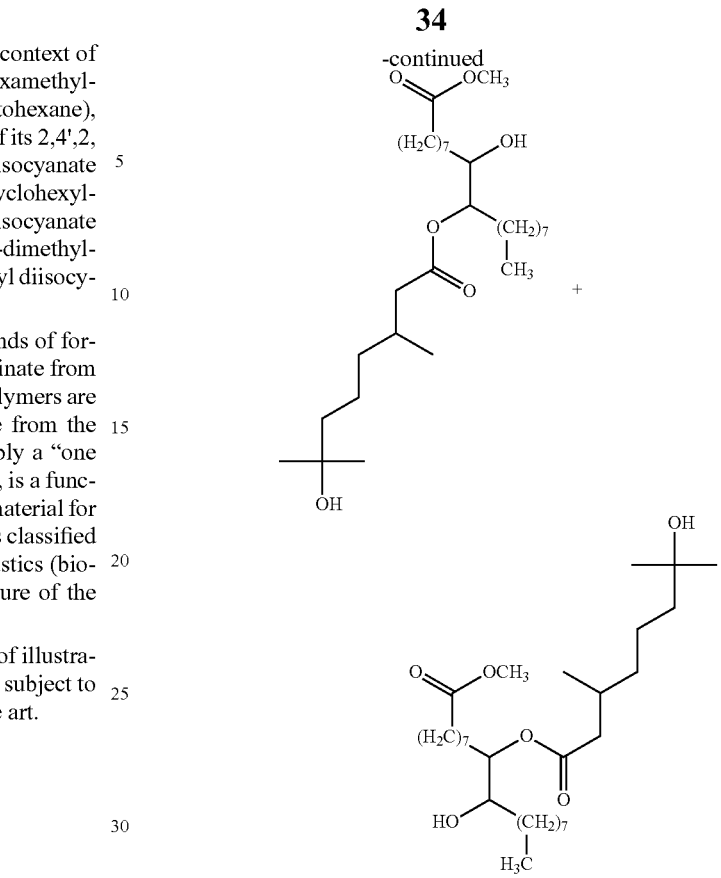

The reaction was carried out in a 100 ml glass reactor with mechanical agitation. Twenty-five grams (25.0 g) of methyl ester of sunflower oil HTO (high oleic content—purity: 85% methyl oleate) as well as 13.0 g of hydroxycitronellal (FCC Grade: Purity≥95%—Sigma-Aldrich, Ref. W258318) were introduced into the reactor. The solid catalyst of the metal type supported on silica contains 5% by weight of the quantity of methyl oleate engaged, i.e. 250 mg. The environment was heated to 80° C. with continuous air bubbling. The air flow was controlled by a ball flow meter at 70 ml/min. After 7 hours of reaction time, the air flow was stopped and the reaction medium was raised to 150° C. These parameters were maintained for 5 additional hours. Samples of the reaction medium were taken at regular intervals in order to determine the status of the reaction. The reagent conversion rates and the yield rates of the desired products after 7 and 12 hours of reaction time are shown in Table 1:

TABLE 1

| Type of catalyst | Reaction time (hr.) | Conversion into methyl oleate (%) | Conversion into hydroxy-citronellal[a] (%) | Epoxide yield (%) | Functionalized products yield (%) |
|---|---|---|---|---|---|
| no catalyst | 7 | 37 | 70 | 27 | 11 |
|  | 12 | 46 | 92 | 9 | 24 |
| Ru/SiO$_2$ | 7 | 75 | 95 | 52 | 24 |
|  | 12 | 80 | 100 | 13 | 39 |
| Co/SiO$_2$ | 7 | 76 | 100 | 31 | 19 |
|  | 12 | 77 | 100 | 16 | 29 |
| Zn/SiO$_2$ | 7 | 66 | 99 | 30 | 20 |
|  | 12 | 69 | 100 | 10 | 27 |
| Ni/SiO$_2$ | 7 | 51 | 90 | 34 | 15 |
|  | 12 | 59 | 98 | 13 | 25 |

TABLE 1-continued

| Type of catalyst | Reaction time (hr.) | Conversion into methyl oleate (%) | Conversion into hydroxy-citronellal[a] (%) | Epoxide yield (%) | Functionalized products yield[b] (%) |
|---|---|---|---|---|---|
| Cr/SiO$_2$ | 7 | 49 | 89 | 31 | 15 |
|  | 12 | 56 | 97 | 13 | 25 |
| Cu/SiO$_2$ | 7 | 34 | 90 | 24 | 16 |
|  | 12 | 38 | 97 | 11 | 22 |
| Rh/SiO$_2$ | 7 | 34 | 86 | 18 | 17 |
|  | 12 | 40 | 96 | 8 | 26 |

[a]values calculated using gas chromatography
[b]values calculated using steric exclusion chromatography The composition of the reaction medium was determined by gas phase chromatographic analysis. The Agilent Technologies 6870N chromatograph is equipped with a capillary column (SGE-BPX-70-length: 30 m, inside diameter: 0.25 mm, film thickness: 0.25 μm), of a split/splitless injector and a flame ionization detector (temperature of the injector and the detector: 280° C.). The temperature program of the furnace was as follows: 80° C. (0 min.)-13° C./min.-180° C. (6 min.)-13° C./min.-220° C. (6 min.)-17° C./min.-250° C. (10 min.).

The hold time for the various products under the conditions described above are as follows: dodecane (2.9 min.); hydroxycitronellal (8.9 min.); methyl oleate (12.6 min.); methyl trans-9,10epoxy-stearate (18.9 min.); methyl cis-9,10-epoxy-stearate (19.2 min).

The conversion of reagents at time t is expressed as follows: (number of initial moles of reagent−number of moles of reagent at time t)/number of initial moles of reagent*100.

The epoxide yield at time t was calculated as follows: number of moles of epoxide at time t/(number of initial moles of methyl oleate*relative response coefficient of 9,10-epoxystearate in relation to methyl oleate)*100.

The functionalized products, i.e. the methyl octadecanoate 9-hydroxy-10-(7-hydroxy-3,7-dimethyloctanoyloxy) and the methyl octadecanoate 10-hydroxy-9-(7-hydroxy-3,7-dimethyloctanoyloxy), were analyzed by steric exclusion chromatography.

The Waters Alliance 2695 chromatograph is equipped with a refraction index detector (RI 410) and with two different columns (Styrage®-HR 0.5 and Styragel®-HR 1). The temperature of the furnace containing the columns is set at 30° C. and tetrahydrofurane (THF) is used as an eluent at a flow rate of 0.8 ml/min.

Under these conditions, the hold times were as follows: products with high molecular weight (>1000 uma; 15.1 min); functionalized products (16.2 min.); methyl oleate and methyl 9,10-epoxy-stearate (18.1 min.); hydroxycitronellal (19.0 min.).

The functionalized products yield is the relative surface area of the chromatographic peak expressed as a percentage of the total of all peaks.

Example 2

This example describes the synthesis of functionalized compounds starting from the methyl oleate. Several aldehydic reagents were tested, comprising hexanal, decanal and benzaldehyde. These three tests lead to the formation of the following products, respectively: methyl 9-(hexanoyloxy)-10-hydroxyoctadecanoate and methyl 10-(hexanoyloxy)-9-hydroxyoctadecanoate if hexanal is used; methyl 9-(decanoyloxy)-10-hydroxyoctadecanoate and methyl 10-(decanoyloxy)-9-hydroxyoctadecanoate for decanal; and lastly methyl 9-(benzoyloxy)-10-hydroxyoctadecanoate and methyl 10-(benzoyloxy)-9-hydroxyoctadecanoate when benzaldehyde was used. These three reactions are presented in Diagrams 3, 4 and 5.

Diagram 3: Functionalization of methyl oleate in the presence of hexanal, by successive epoxidation and acylation.

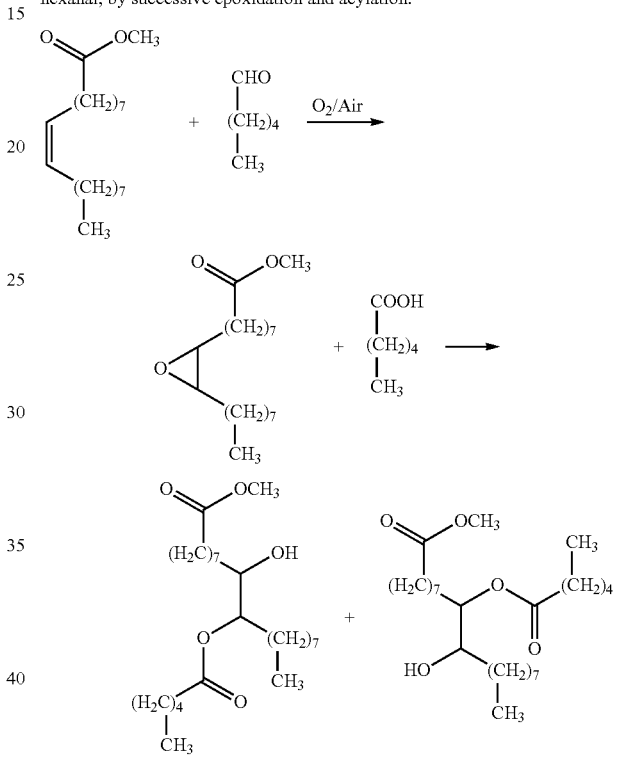

Diagram 4: Functionalization of methyl oleate in the presence of decanal by successive epoxidation and acylation.

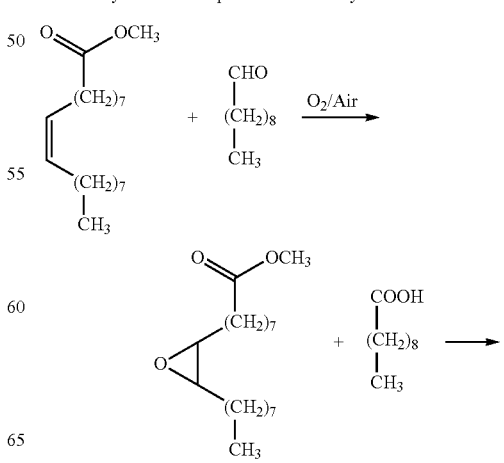

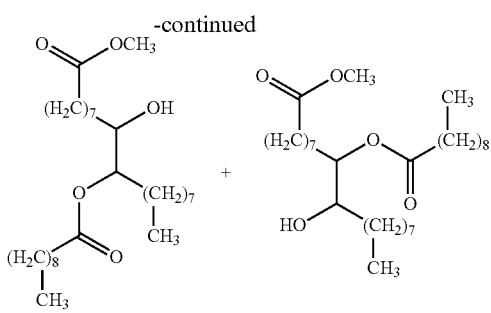

Diagram 5: Functionalization of methyl oleate in the presence of benzaldehyde by successive epoxidation and acylation.

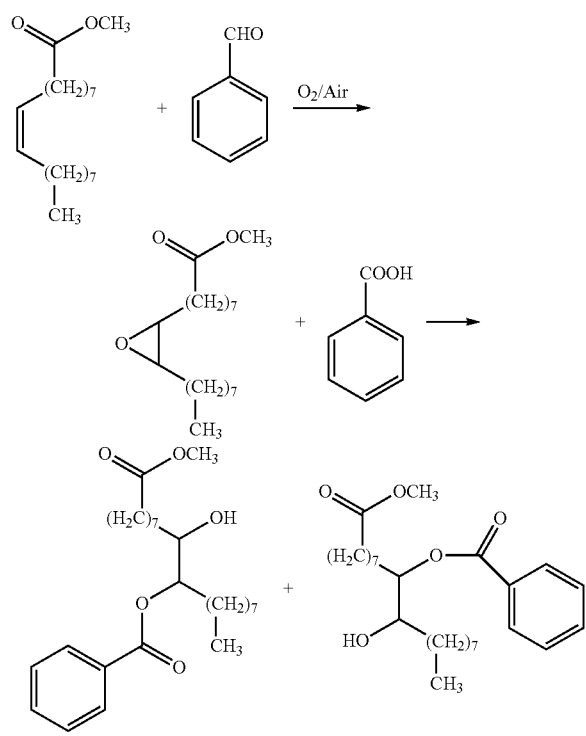

The reaction was carried out in a 100 ml glass reactor with mechanical agitation. In all cases, a weight of 25.0 g of methyl ester of sunflower oil HTO (high oleic content—purity: 85% methyl oleate) was placed in the reactor. A quantity of aldehyde was added; the quantity is equivalent to approximately one and one-half the number of moles of methyl oleate used. So, for the hexanal presence test, a quantity equal to 7.1 g of hexanal (purity: 98%-Sigma-Aldrich-ref.: 115606) was placed in the reactor. For decanal, this quantity was equivalent to 11.2 g (purity: 98%0 Sigma-Aldrich-ref. D7384) and in the case of benzaldehyde, 8.6 g of benzaldehyde (purity: 99%-Sigma-Aldrich-ref.: B 1334) were added. The solid ruthenium on silica catalyst, containing 1.5% by weight of ruthenium, was added to the reaction mix at a ratio of 2% by weight of the quantity of methyl oleate used, i.e. 500 mg.

Then, the medium was heated to 80° C. by a continuous bubbling air flow at atmospheric pressure. The air flow rate was controlled by a ball flow meter and was 30 ml/min. In the case of hexanal and benzaldehyde, after 6 hours of reaction, the air flow rate was stopped and the reaction medium was placed in an inert atmosphere (nitrogen). In the case of decanal, the same operation was carried out after 10 hours of reaction time. In all cases, the time necessary for total conversion of the aldehyde was allotted. Then, the reaction temperature was increased to 150° C. These parameters were maintained for 20 additional hours in the case of hexanal, 15 hours for decanal and 9 hours for benzaldehyde. Samples of the reaction medium were taken at regular intervals in order to determine the progress of the reactions. The composition of the various reaction media after each reaction step is shown in Table 2:

TABLE 2

| Type of aldehyde | Time (hours) | Conversion to methyl oleate (%) | Conversion to aldehyde (%) | Epoxide yield (%) | Functionalized products yield (%) |
|---|---|---|---|---|---|
| hexanal | 6 | 63 | 100 | 47 | 0 |
|  | 20 | 76 | 100 | 11 | 10 |
| decanal | 10 | 92 | 100 | 45 | 2 |
|  | 25 | 95 | 100 | 10 | 7 |
| benz-aldehyde | 6 | 100 | 93 | 56 | 0 |
|  | 15 | 100 | 96 | 7 | 17 |

The composition of the reaction medium was determined by gas phase chromatographic analysis. The Agilent Technologies 6870N chromatograph used is as described in Example 1.

Two different temperature programs were used. The first was as follows: 50° C. (5 min.)-10° C./min.-100° C. (5 min.)-10° C./min.-150° C. (5 min.)-10° C./min.-220° C. (5 min.)-10° C./min.-250° C. (5 min.).

This program allowed hexanal in particular to be detected. The hold time of the various products under the conditions described above, with a pressure level at the head of the column equal to 16.32 psi were as follows: hexanal (6.9 min.); dodecane (8.1 min.); methyl oleate (30.0 min.); methyl trans-9,10-epoxy-stearate (34.5 min); methyl cis-9,10-epoxy-stearate (34.9 min).

The conversion of the reagents at time t is expressed as described in Example 1. The epoxide yield at time t was calculated as described in Example 1.

The second temperature program for the furnace was as follows: 80° C. (0 min.)-13° C./min.-180° C. (6 min.)-13° C./min.-220° C. (6 min.)-17° C./min.-250° C. (10 min.). The functionalized products were detected upon completion of the analysis.

The hold time for the various products at the conditions described above were as follows: dodecane (2.9 min.); decanal (5.2 min.); benzaldehyde (5.4 min.); methyl oleate (12.6 min.); methyl trans-9,10-epoxy-stearate (18.9 min.); methyl cis-9,10-epoxy-stearate (19.2 min.); methyl 9-(hexanoyloxy)-10-hydroxyoctadecanoate and methyl methyl 10-(hexanoyloxy)-9-hydroxyoctadecanoate (29.8 et 29.9 min.); methyl 9-(decanoyloxy)-10-hydroxyoctadecanoate and methyl 10-(decanoyloxy)-9-hydroxyoctadecanoate (34.4 et 34.5 min.); methyl 9-(benzoyloxy)-10-hydroxyoctadecanoate and methyl 10-(benzoyloxy)-9-hydroxyoctadecanoate (38.7 et 38.9 min.).

Yields of functionalized products were calculated by assigning a response factor equal to one to a surface area of the corresponding chromatographic peaks related to that of the initial methyl oleate.

All functionalized products were identified by gas phase chromatographic analysis coupled with a mass spectrometer as well as steric exclusion chromatograph.

Example 3

This example describes the synthesis of compounds functionalized at the start by hexanal. Several unsaturated compounds were tested, such as 1-octene, 4-octene and cyclooctene. These three tests led to the formation of 2-hydroxyoctyl hexanoate, 1-hydroxyoctan-2-yl hexanoate and octane-1,2-diyl dihexanoate in the case of the reaction of 1-octene with hexanal; 5-hydroxyoctan-4-yl hexanoate and dihexanoate of cyclooctane; 1,2 diyl for cyclooctene. These three reactions are illustrated in Diagrams 6, 7 and 8, below.

Diagram 6: Diagram of functionalization of 1-octene in the presence of hexanal by successive epoxidation and acylation.

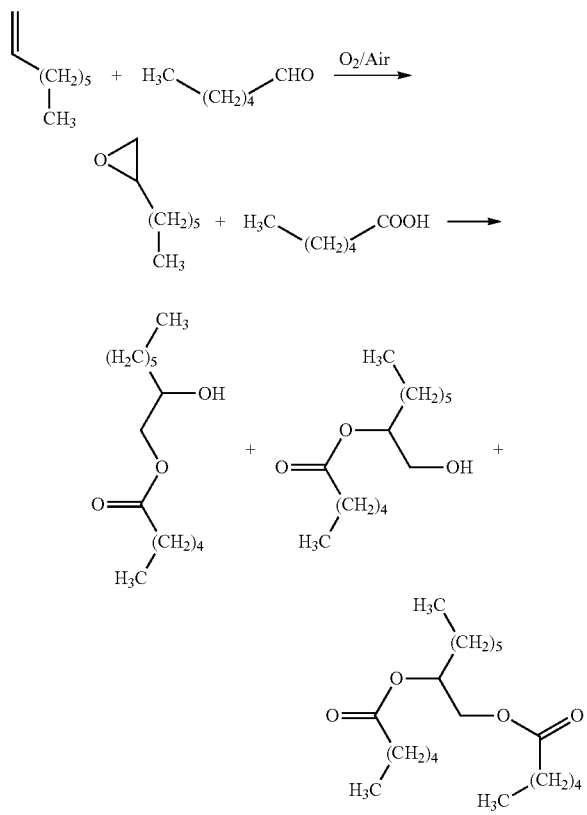

Diagram 7: Diagram of the functionalization of 4-octene in the presence of hexanal via successive epoxidation and acylation.

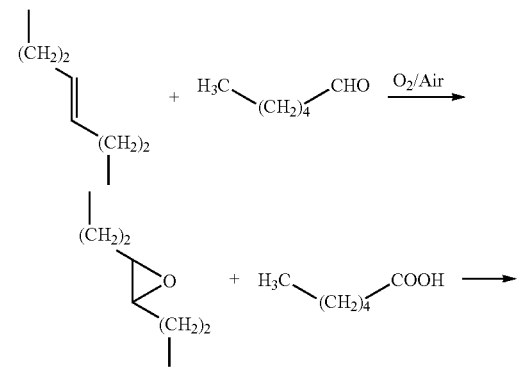

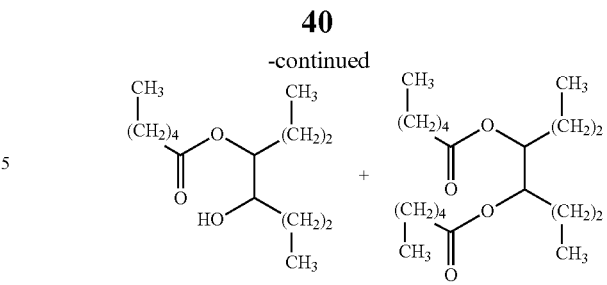

Diagram 8: Diagram of the functionalization of cyclooctene in the presence of hexanal by successive epoxidation and acylation.

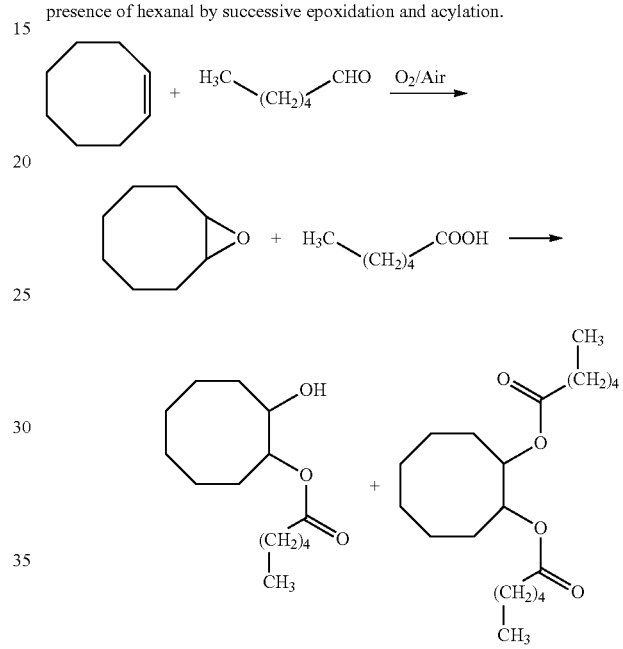

The reaction was conducted in a 100 ml glass reactor equipped with mechanical agitation. In all three cases, a weight of 15.0 g of the unsaturated compound was placed in the reactor. In the first case, the 1-octene (Sigma-Aldrich-purity: 98%-batch 0001452135); in the second, 4-octene (Sigma-Aldrich-purity: 90%-batch 10325JE); and in the third case cyclooctene (Sigma-Aldrich-purity: 95%-batch 7238917). Then, 20.5 g of hexanal (Sigma-Aldrich-purity: 98%-batch S88145-279) were placed in each reactor, along with 300 mg of solid catalyst of the ruthenium on silica, containing 1.5% by weight of ruthenium. The medium was heated to 80° C. under a constant bubbling air flow. The air flow rate was controlled by a ball flow meter and was 30 ml/min. After 7 hours of reaction time, the air flow was stopped and the reaction medium was placed in an inert atmosphere (nitrogen). At the same time, the reaction temperature was increased to 120° C. These parameters were maintained for 15 additional hours in all cases and for 70 hours in the case of the 4-octene. Samples of the reaction medium were taken at regular intervals in order to determine the progress of the reaction. The composition of the various reaction media after each reaction step is shown in Table 3, while the kinetic conversion curves for reagents and product yield in the case of 4-octene are shown in the graph of FIG. 1:

TABLE 3

| Type of olefin | Time (hours) | Conversion to olefin (%) | Conversion to hexanal (%) | Epoxide yield (%) | Functionalized products yield (%) | Difunctionalized products yield (%) |
|---|---|---|---|---|---|---|
| 1-octene | 7 | 78 | 100 | 10 | 3 | 6 |
|  | 22 | 90 | 100 | 0 | 7 | 5 |
| 4-octene | 7 | 84 | 100 | 51 | 2 | 0 |
|  | 22 | 96 | 100 | 27 | 26 | 2 |
|  | 77 | 100 | 100 | 0 | 10 | 10 |
| cyclooctene | 7 | 100 | 100 | 74 | 4 | not avail. |
|  | 22 | 100 | 100 | 69 | 3 | not avail. |

The quantitative composition of the various reaction media was determined by gas phase chromatographic analysis. The Agilent Technologies 6870N chromatograph used is as described in Example 1.

The temperature program of the furnace was as follows: 50° C. (5 min.)-10° C./min.-100° C. (5 min.)-10° C./min.-150° C. (5 min.)-10° C./min.-220° C. (5 min.)-10° C./min.-250° C. (5 min.).

The hold times of the various products under the conditions described previously, with a pressure level at the top of the column equal to 16.32 psi, were as follows: 4-octene (2.9 min.); 1-octene (2.9 min.); cyclooctene (5.1 min.); hexanal (6.9 min.); dodecane (8.1 min.); 4,5-epoxyoctane (8.1 min.); 1,2-epoxyoctane (9.6 min.); epoxycyclooctane (15.8 min.); 5-hydroxyoctan-4-yl hexanoate (26.6 min.); octane-4,5-diyl dihexanoate (29.0 min.); octane-1,2-diyl dihexanoate (30.3 min.); 2-hydroxyoctyl hexanoate and 1-hydroxyoctan-2-yl hexanoate (29.7 and 31.6 min.); 2-hydroxycyclooctyl hexanoate (31.9 min.).

The conversion of reagents at time t is expressed as described in Example 1. The epoxidated product yield at time t was calculated as follows: (number of moles of product at time t/(initial number of moles of the corresponding reagent*relative response coefficient of the product in relation to the reagent)*100.

The yield values of functionalized compounds were calculated in the same manner but by assigning a response coefficient equal to one.

All the functionalized products were identified by gas phase chromatographic analysis coupled with mass spectrometry.

Example 4

This example relates to the synthesis of functionalized molecules from a compound of formula (II) and (III) which are the same, since the molecule used is 3-cyclohexene-1-carboxaldehyde with both functionalities, unsaturation and aldehyde. The successive epoxidation and acylation reactions of this molecule lead first to the production of the intermediate epoxy-acid and then to the formation of dimers, trimers and oligomers of the initial compound, as shown in Diagram 9.

Diagram 9: Functionalization of 3-cyclohexene-1-carboxaldehyde by successive epoxidation and acylation.

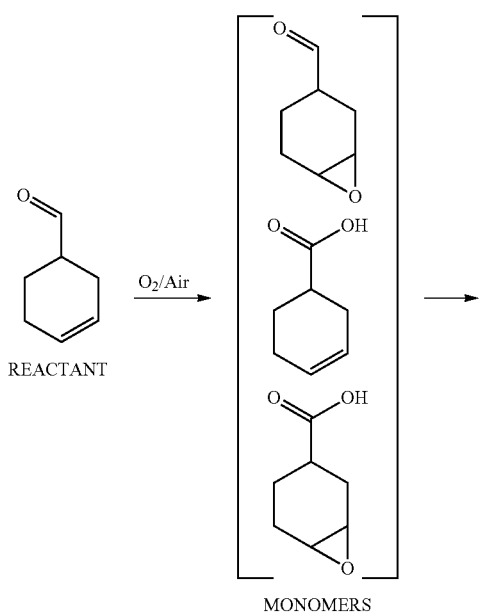

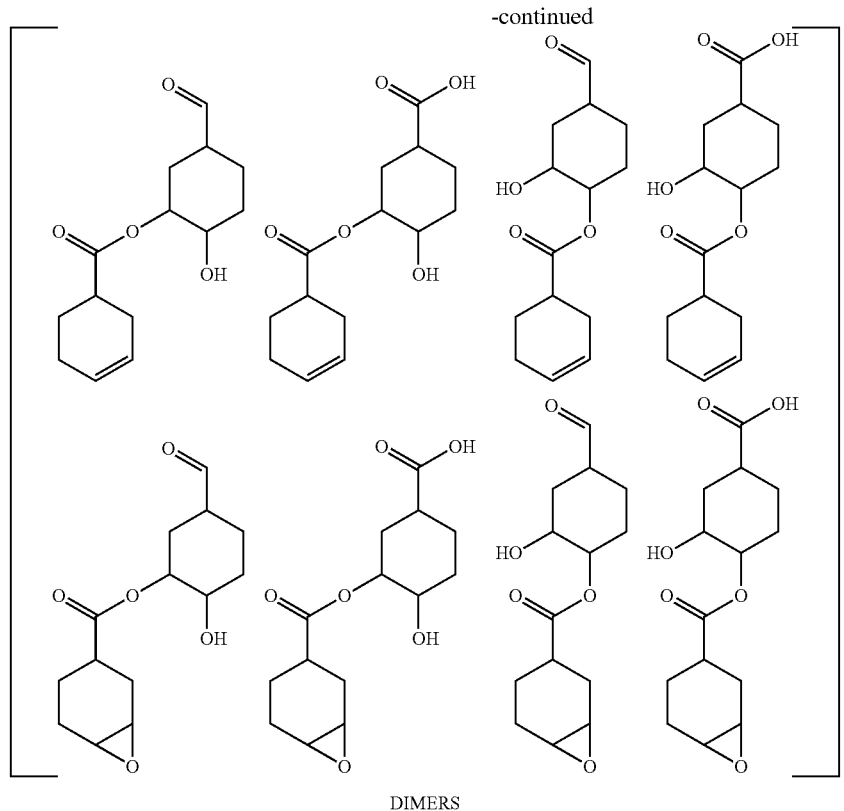

DIMERS

Figure 2:
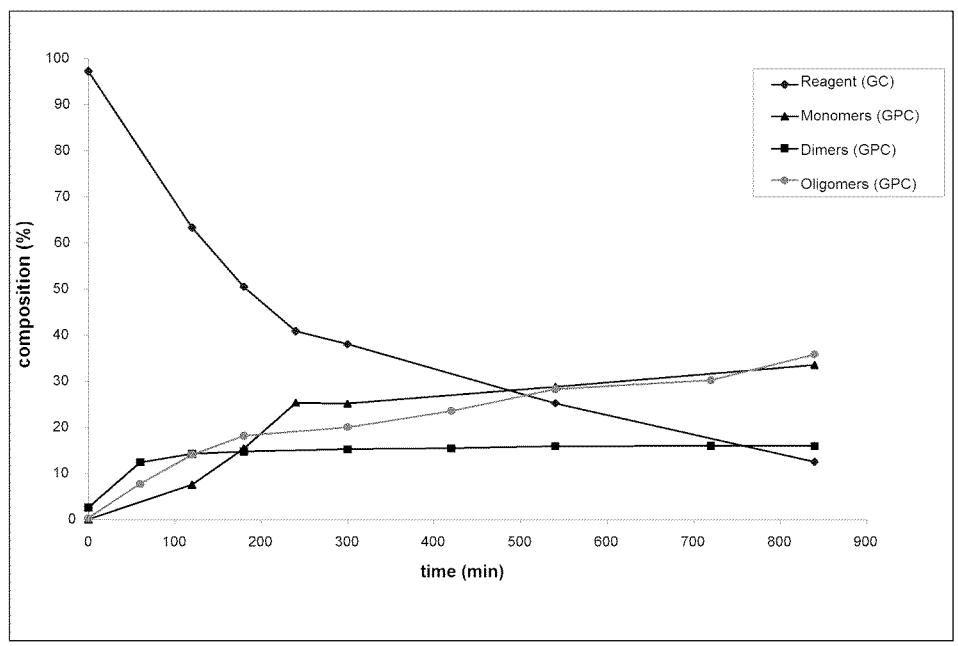
FIG. 2 presents a graph showing the evolution of the composition of the reaction medium as a function of time for the reaction of Example 4.

The reaction was carried out in a 100 ml glass reactor equipped with mechanical agitation. A weight of 30.0 g of 3-cyclohexene-1-carboxaldehyde (Sigma-Aldrich-purity: 97%-batch MKBD1569) was placed in the reactor. The solid ruthenium on silica catalyst, containing 1.5% by weight of ruthenium, was added to the reaction mixture at a rate of 1% by weight of the quantity of reagent engaged, i.e. 300 mg. The medium was heated to 80° C. in a continuous bubbling air flow. The air flow rate was controlled by a ball flow meter and was 70 ml/min. The reaction was conducted over 14 hours without replacement of the air with nitrogen. The reaction temperature was maintained during the entire duration of the test at 80° C. Samples of the reaction medium were taken at regular intervals in order to determine the status of the reaction. In this case, the status of the reaction was determined by steric exclusion chromatography. The results are presented in the form of a graph summarizing the kinetic curves of the status of the reaction in FIG. 2.

The composition of the reaction medium was determined by steric exclusion chromatography. The Alliance 2695 chromatograph from Waters was equipped with a refraction index detector (RI 410) and two different columns (Styragel®-HR 0.5 and Styragel®-HR 1). The temperature of the furnace containing the columns was set at 30° C. and tetrahydrofurane (THF) was used as the eluent at a flow rate of 0.8 ml/min.

A calibration curve was plotted using polystyrene standards on a signal measurement base of the refraction index detector. These standards comprised styrene polymers with a known molecular weight. This calibration curve was plotted on a graph showing the base-10 logarithm of the molar weight in function of hold time. So, the various by-products of the reaction were able to be identified by measuring their respective molecular weight.

Under the conditions for analysis described above, the hold times were as follows: The term "monomers" used in the graph in FIG. 2 includes the reagent and the monomer products of the reaction; 3-cyclohexene-1-carboxaldehyde (22.84 min.), 3-cyclohexene-1-carboxylic acid (21.54 min.), 3,4-epoxycyclohexane-1-carboxaldehyde (21.54 min.) and 3,4-epoxycyclohexane-1-carboxylic acid (20.90 min.). The term "dimers" includes all dimeric compounds (19.63+19.13+18.63 min.). Lastly, the term "trimers and oligomers" covers the compounds with the highest molecular mass (18.32+17.75 min.).

Quantification was carried out based on the signal of the refraction index detector, by assigning all components in the reaction medium a response coefficient equal to one. Therefore it was the proportion, in terms of peak surface area, of each of them (or group of peaks) in relation to the total surface area of all the peaks that was calculated.

Example 5

This example describes the synthesis of a thermoplastic polyurethane obtained starting with a diol synthesized by the process that is the subject of the invention. The diol in question was completely biosourced and comes from the reaction of methyl oleate and hydroxycitronellal. The application of the process to two reagents led to the synthesis of methyl 9-hydroxy-10-(7-hydroxy-3,7-dimethyloctanoyloxy)octadecanoate and of methyl 10-hydroxy-9-(7-hydroxy-3,7-dimethyloctanoyloxy)octadecanoate as shown in Example No. 1. These two molecules are position isomers and represent the source of diol for the fabrication of polyurethane, the source of diisocyanate being the 1,6-diisocyanatohexane (HMDI).

The functionalization reaction of the methyl oleate was conducted in a closed reactor equipped with mechanical agitation, pressurized with pure oxygen and in the absence of any solvent. A weight of 10.0 g of methyl oleate (Sigma Aldrich-purity: 99%-ref. 311111) as well as 29.0 g of hydroxy-citronellal (FCC grade-purity: ≥95-Sigma-Aldrich-ref. W258318) were placed in the reactor. The solid metal catalyst supported on silica contains 1.5% by weight of metal and was added to the rectional mixture at a ratio of 2% by weight of the methyl oleate quantity, i.e. 200 mg. The medium was heated to 70° C. and oxygen was introduced to a pressure level of 4 bars. This pressure level was kept constant by regular additions of oxygen. The epoxidation reaction, the first step of the one pot process, was terminated after 2 hours (no further oxygen consumption). At that moment, the epoxide yield was 90% with a selectivity of 95% (evaluated by gas chromatography using the method described in Example No. 1). Then the reactor was returned to atmospheric pressure, the reaction medium was degassed and any residual oxygen was vented by adding nitrogen. The temperature was increased to 120° C. and the second step of the one pot process, the epoxide opening reaction, began. This step was much slower and took 48 hours.

Once the functionalization reaction was completed, the excess citronellic acid present in the reaction medium was eliminated by liquid-liquid extraction. The reaction medium was diluted in diethyl ether then centrifuged in order to eliminate the solid catalyst. The ethereal organic phase was then placed in a vial in order to be decanted and an aqueous NaOH solution with a concentration of 0.3 M was added. Several successive washings of the organic phase were carried out with a basic solution, ending with a 0.05 M HCl solution. Lastly, a final washing was carried out with an NaCl saturated solution until the acidity was removed. The organic phase then was dried with sodium carbonate and the diethyl ether was evaporated via a rotary evaporator. At this point, the reaction medium consisted of 72% of the opening product (diol) according to the steric exclusion chromatography analysis (analysis method described in Example No. 1).

The polymerization reaction was also conducted in an inert (nitrogen) atmosphere. The diol obtained in the previous step was heated to 120° C. and the 1,6-diisocyanatohexane was added in a semi-molar quantity in relation to the diol. After 2 hours of reaction time, the temperature was increased to 150° C. and a quantity of diisocyanate was added in order to make the total quantity equimolar in relation to the diol. The reaction continued for 2 additional hours.

In order to demonstrate the formation of a polyurethane, two analytical techniques were used: steric exclusion chromatography and infrared spectrometry. The former showed the evolution of the molar weight of the product, and the second demonstrated the formation of urethane bonds.

Steric exclusion chromatography analyses were conducted using a Waters Alliance 2695 chromatograph equipped with a refraction index detector (RI 410) and three different columns (Styrage® columns—HR 0.5-HR 1-HR 3). The temperature of the furnace containing the columns was set at 30° C. and tetrahydrofurane (THF) was used as an eluent at a flow rate or 0.8 ml/min.

A calibration curve, based on the molar weight logarithm for polystyrene standards as a function of hold time was established. Four standards having a known molecular weight and molecular structure similar to that of the functionalization product in question were analyzed in order to determine the correction factor. The first part of Table 4 below summarizes the results of the analysis of the functionalized product before polymerization and the second part of the table, the results obtained upon completion of the polymerization step.

TABLE 4

| | Hold time (min.) | Percentage peak area | Measured molecular weight | Corrected molecular weight |
|---|---|---|---|---|
| Before polymerization | 27.411 | 71.99 | 830 | 538 |
| | 28.538 | 12.97 | 564 | 388 |
| | 29.680 | 12.07 | 418 | 301 |
| | 31.703 | 2.97 | 284 | 217 |
| After 4 hours | 19.312 | 5.05 | 120,324 | 35,946 |
| | 20.549 | 19.52 | 18,012 | 7,229 |
| | 22.359 | 35.51 | 5,313 | 2,578 |
| | 23.987 | 13.56 | 2,961 | 1,574 |
| | 25.125 | 5.53 | 1,989 | 1,124 |
| | 26.104 | 7.79 | 1,372 | 822 |
| | 27.749 | 5.43 | 734 | 485 |
| | 29.743 | 7.62 | 412 | 298 |

The initial mixture contained approximately 70% of the functionalized product. After the polymerization reaction, the most representative oligomers contain from 5 to 10 monomeric units with about 5% of oligomers containing 50 units. Longer polymer chains are also probably present.

Figure 3:
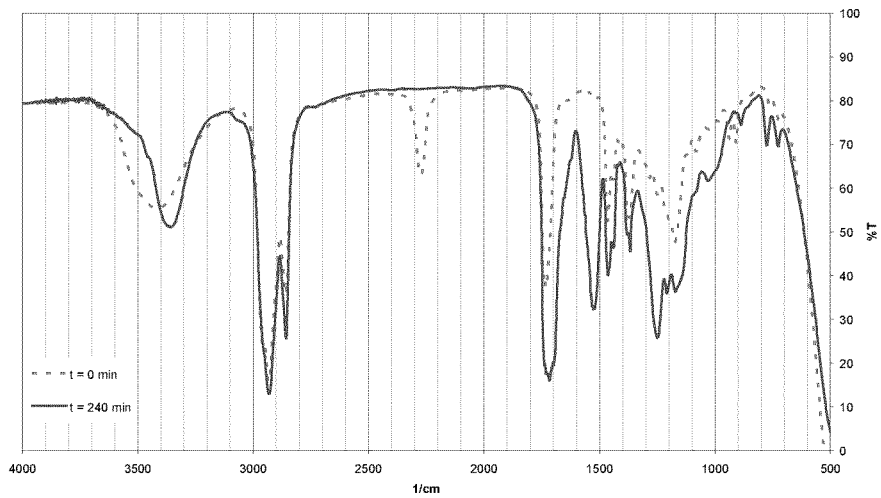
FIG. 3 presents the infrared spectra of the functionalized product from Example 5, in the presence of di-isocyanate before polymerization (t=0 min) and after polymerization (t=240 min).

FIG. 3 shows the infrared spectra of the functionalized product in the presence of diisocyanate before polymerization (t=0 min) and after polymerization (t=240 min).

One can observe the disappearance of the O—H bond absorption band towards 3400 cm$^{-1}$ to the benefit of the N—H bond band of the secondary amino acid around 3,350 cm$^{-1}$. The disappearance of the peak characterizing isocyanates between 2,300 and 2,200 cm$^{-1}$ shows their conversion. The increase in intensity of the C═O absorption band of esters between 17,30 and 1,715 cm$^{-1}$ is due to the contribution of the C═O double bonds of the urethane functions. Lastly, the appearance of peaks at 1,520 cm$^{-1}$ and 1,250 cm$^{-1}$, characteristic of urethane bonds, may be observed.

Example 6

This example describes the synthesis of a thermo-hardening polyurethane obtained from functionalized soy oil. The polyol obtained by functionalization of the soy oil in the presence of butyraldehyde was used to produce polyurethane, and the diisocyanate was 1,6-diisocyanatohexane (HMDI).

The functionalization reaction was conducted in a closed reactor equipped with mechanical agitation, pressurized with pure oxygen and in the absence of any solvent. A weight of 10.0 g of refined soy oil (iodine index: 112.5 g $I_2$/100 g) as well as 30.0 g if butyraldehyde (Sigma-Aldrich-purity: 99%-ref. 538191) were placed into the reactor. The solid metal-type catalyst supported on silica contains 1.5% by weight of metal and was also added to the reaction mixture at a ratio of 2% by weight of the quantity of methyl oleate used, i.e. 200 mg. The medium was heated to 70° C. and oxygen was introduced until a pressure level of 4 bars was reached. This pressure level was kept constant by the regular addition of oxygen. The epoxidation reaction, the first step of the one pot process, was halted after 4 hours (no further oxygen consumption). Then the reactor was brought back to atmospheric pressure, the reaction medium was degassed and the residual oxygen was displaced by the nitrogen. the temperature was increased to 120° C. and the second step of the one pot process began, i.e. the opening reaction of the epoxide that required 48 hours.

Once the functionalization reaction was completed, the excess butyric acid present in the reaction medium was eliminated by liquid-liquid extraction according to the protocol described in Example No. 5.

The polymerization reaction was conducted in an inert atmosphere (nitrogen). The polyol obtained in the preceding step was heated to 100° C. and 1,6 diisocyanatohexane was added in a very small quantity in order to cause the polymerization reaction while keeping the mixture in the liquid state necessary for chromatographic and spectrometric analyses.

Steric exclusion chromatography analyses were conducted according to the protocol of Example No. 5. The first part of Table 5 below summarizes the results of the analysis of the functionalized product before polymerization and the second part of the table summarizes the results obtained after partial polymerization (since the thermohardened sample was not soluble in THF).

TABLE 5

|  | Hold time (min.) | Percentage peak area | Measured molecular weight | Corrected molecular weight |
|---|---|---|---|---|
| Before polymerization | 22.729 | 23.02 | 4,580 | 2,274 |
|  | 23.501 | 19.62 | 3,486 | 1,806 |
|  | 25.075 | 57.37 | 2,026 | 1,142 |
| After 30 minutes | 19.196 | 22.01 | 154,860 | 44,484 |
|  | 20.346 | 20.14 | 22,620 | 8,763 |
|  | 22.273 | 18.23 | 5,513 | 2,660 |
|  | 23.301 | 12.57 | 3,731 | 1,913 |
|  | 25.115 | 27.04 | 1,996 | 1,128 |

The initial mixture contained approximately 77% of the functionalized oil, which could contain up to 9 butyranoate functions. After the partial polymerization reaction, the most representative oligomers contained just 32 monomeric units. At this step, there remained approximately 40% of monomers but beyond this proportion, the mixture became solid and non-analyzable. For total polymerization, it is apparent that the molar weights are higher than those indicated.

Figure 4:
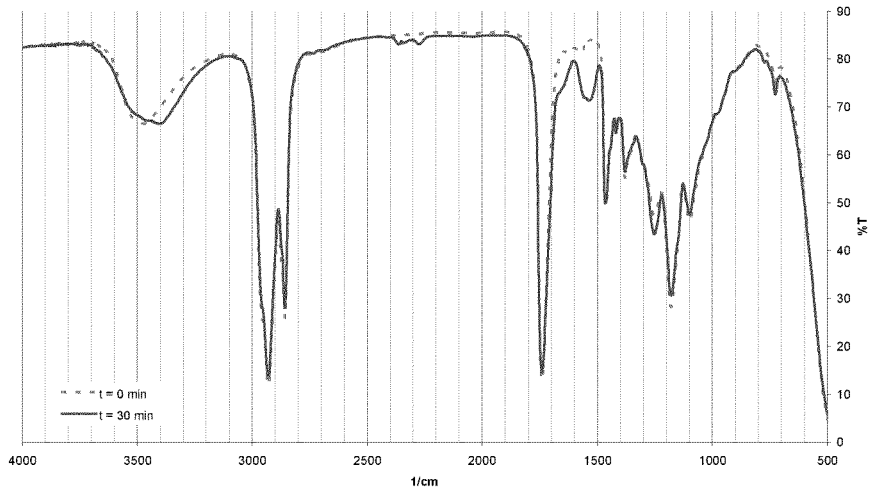
FIG. 4 presents the infrared spectra of the product functionalized from Example 6 before polymerization (t=0 min) and after polymerization (t=30 min).

FIG. 4 below shows the infrared spectra of the functionalized product before polymerization (t=0 min) and after polymerization (t=30 min.).

An attenuation of the absorption band of the of the O—H bond towards 3,475 cm$^{-1}$ for the benefit of the band of the N—H bond of the secondary amine towards 3,400 cm$^{-1}$ was observed. The appearance of peaks at 1,520 cm$^{-1}$ and 1,250 cm$^{-1}$ that are characteristic of urethane bonds, were also observed.

Example 7

This example illustrates the use of a catalyst for the second step of the one pot process between methyl oleate and hexanal, in order to form methyl 9-(hexanoyloxy)-10-hydroxyoctadecanoate methyl 10-(hexanoyloxy)-9-hydroxyoctadecanoate. The catalysts tested were:
  solid acid catalysts. An Amberlyst® 15 (A15) polymer resin functionalized by sulfonic functions (strong acid resin) and four different Montmorillonites: One Montmorillonite (M) has a specific surface area of 330 m²/g and a PZC (zero charge point) of 2.8-3.8; a second (MAl) with a specific surface area of 250 m²/g and the PZC between 4 and 5; a third (MK10) with a specific surface area of 250 m²/g and a PZC of 3.6; and the last one (MKSF) having a specific surface area of between 20 and 40 m²/g.
  solid basic catalysts. Two Amberlyst® polymer resins, one of Type 21 (A21) functionalized by amino alkyls (low base resin) and the other of Type 26 (A26) functionalized by quaternary ammoniums (strong base resin). Calcium oxide (CaO) was also tested, as was synthetic hydrotalcite (Mg$_6$Al$_2$(CO$_3$)(OH)$_{16}$.4H$_2$O).
  homogenous catalysts. These are hexylamine, dihexylamine, trihexylamine, and potassium hydroxide.

Each reaction was conducted in a 100 ml glass reactor equipped with mechanical agitation. In all cases, a weight of 20.0 g of hexanal (purity: 98%-Sigma Aldrich-ref. 115606) were placed into the reactor. The metal solid catalyst supported on silica contains 1.5% by weight of ruthenium and was added to the reaction mix at a ratio of 1% by weight of the volume of methyl ester engaged, i.e. 200 mg.

Then, the medium was heated to 80° C. with a flow of pure oxygen at atmospheric pressure. The air flow rate was controlled by a ball flow meter and was 10 ml/min. After 7 hours of reaction, the methyl oleate conversion was at 89%, the hexanal conversion was at 96% and the epoxide yield was at 72%. At this moment, the air flow was stopped and the reaction medium was placed in an inert atmosphere (nitrogen). The reaction medium was maintained at 80° C. and the opening catalyst was added at a ratio of 5% by weight for solid catalysts and 50 μl in the case of hexylamines. In regards to potassium hydroxide, 50 μl of a methanolic solution with a concentration of 0.5 M were added. The medium was agitated for 24 additional hours.

Figure 5:
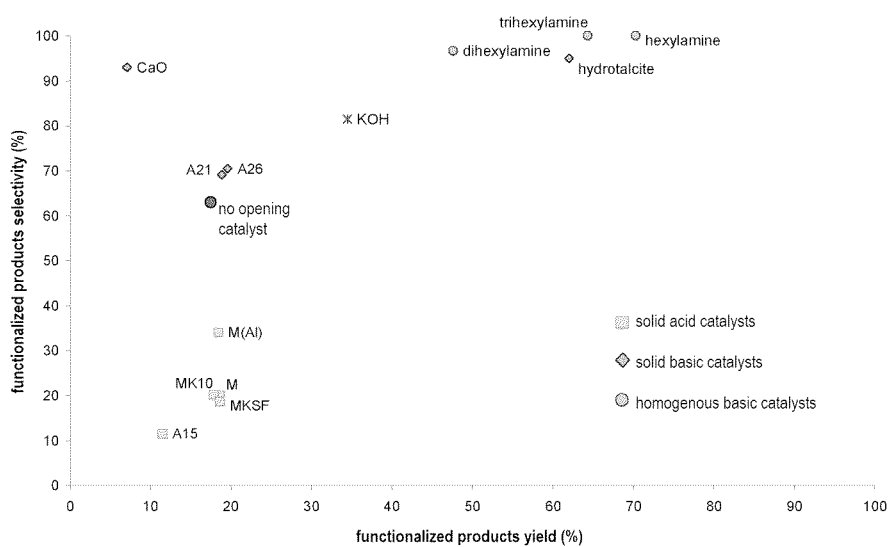
FIG. 5 presents a graph showing selectivity of functionalized products as a function of the yield for the catalysts tested in Example 7.

FIG. 5 shows in graphical form the results obtained regarding the selectivity of functionalized products based on yield, upon completion of the one pot reaction, after 31 hours.

The composition of the reaction medium was determined by gas phase chromatographic analysis according to the protocol described in Example No. 2.

The invention claimed is:
1. A process for synthesizing multifunctional compounds comprising a reaction of a compound of formula (II) with atmospheric or molecular oxygen, in the presence of at least one aldehyde of formula (III), and optionally in the presence of at least one catalyst or at least one radical initiator;

(II)

(III)

wherein:
  $R^{10}$ is H, or is selected from the group consisting of $C_1$-$C_{20}$ alkyl, $C_2$-$C_{20}$ alkenyl, and $C_6$-$C_{12}$ aryl, with each group optionally being substituted by one or several groups, that are either identical or different, selected from the group consisting of a halogen atom, —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CO$_2$R$^{60}$;
  $R^{20}$ is H, cyano, a halogen atom, or —CHO, or is selected from the group consisting of $C_1$-$C_{20}$ alkyl, $C_2$-$C_{20}$ alkenyl, $C_6$-$C_{12}$ aryl, and $C_6$-$C_{12}$ aryl$C_1$-$C_6$ alkyl with each group optionally being substituted by one or several groups, that are either identical or different, selected from the group consisting of a halogen atom, —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CO$_2$R$^{60}$;

R$^{30}$is selected from the group consisting of epoxy, —OCOR$^8$, —CHO$_2$R$^8$, $C_1$-$C_{20}$ alkyl, $C_2$-$C_{20}$ alkenyl, $C_6$-$C_{12}$ aryl, and $C_6$-$C_{12}$ aryl $C_1$-$C_6$ alkyl, with each group optionally being substituted by one or several groups, that are either identical or different, selected from the group consisting of a halogen atom, —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CHO$_2$R$^{60}$;

R$^{40}$is H, cyano, a halogen atom, or —CHO, or is selected from the group consisting of $C_1$-$C_{20}$ alkyl, $C_2$-$C_{20}$ alkenyl, and $C_6$-$C_{12}$ aryl, with each group optionally being substituted by one or several groups, that are either identical or different, selected from the group consisting of a halogen atom, —OH, —CHO, oxo, cyano, —NR$^9_2$, epoxy, $C_1$-$C_4$ alkoxy, —OCOL$^2$R$^{50}$, $C_1$-$C_6$ alkyl, $C_6$-$C_{12}$ aryl, —OCOR$^8$, and —CHO$_2$R$^{60}$;

or R$^{10}$and R$^{30}$may, with the carbons to which they are bound, form a group selected from the group consisting of a $C_5$-$C_{12}$ cycloalkyl and a $C_5$-$C_{12}$ cycloalkenyl, with each group optionally being substituted by one or several groups, that are either identical or different, selected from the group consisting of a halogen atom, —OH, —CHO, cyano, oxo, epoxy, —OCOR$^8$, —CHO$_2$R$^{60}$, —OCOL$^2$R$^{50}$, $C_1$-$C_6$ alkyl, $C_1$-$C_6$ hydroxyalkyl, and $C_2$-$C_6$ alkenyl;

R$^{50}$is selected from the group consisting of H, —CHO, epoxy, a halogen atom, —OH, —SR$^8$, cyano, nitro, isocyanate, $C_1$-$C_{20}$ alkyl, $C_1$-$C_4$ alkoxy, $C_2$-$C_{20}$ alkenyl, $C_2$-$C_{20}$ alkynyl, heterocycloalkyl, —CHO$_2$R$^8$, and —NR$^9_2$;

L$^2$ is a single covalent bond, or is selected from the group consisting of $C_1$-$C_{20}$ alkylene, $C_3$-$C_{12}$ cycloalkylene, $C_2$-$C_{12}$ alkenylene, $C_5$-$C_{12}$ cycloalkenylene, $C_6$-$C_{12}$ arylene, heteroarylene, and heterocycloalkylene, with each group optionally being substituted by one or several groups, that are either identical or different, selected from the group consisting of a halogen atom, oxo, nitro, —CHO, —OH, —NR$^9_2$, $C_1$-$C_6$ alkyl, $C_1$-$C_4$ alkoxy, $C_6$-$C_{12}$ aryl $C_1$-$C_6$ alkyl, $C_6$-$C_{12}$ aryloxy, $C_1$-$C_6$ alkyl $C_6$-$C_{12}$ aryl, $C_1$-$C_6$ hydroxyalkyl, and $C_6$-$C_{12}$ aryl;

R$^{60}$is selected from the group consisting of H and $C_1$-$C_6$ alkyl optionally substituted by one or several groups, that are either identical or different, selected from the group consisting of —OH, —CHO, —O—CHOR$^7$, and $C_1$-$C_6$ alkyl;

R$^7$ is selected from the group consisting of $C_1$-$C_{24}$ alkyl, $C_2$-$C_{20}$ alkenyl, and $C_6$-$C_{12}$ aryl, with each group being optionally substituted by one or several groups, that are either identical or different, selected from the group consisting of —OH, epoxy and —OCOL$^1$R$^5$;

R$^8$ is H or $C_1$-$C_6$ alkyl;

each identical or different R$^9$ is selected from H, $C_1$-$C_6$ alkyl, or $C_6$-$C_{12}$ aryl L$^1$ is a single covalent bond, or is selected from the group consisting of $C_1$-$C_{20}$ alkylene, $C_3$-$C_{12}$ cycloalkylene, $C_2$-$C_{12}$ alkenylene, $C_5$-$C_{12}$cycloalkenylene, $C_6$-$C_{12}$ arylene, heteroarylene, and heterocycloalkylene, with each group optionally being substituted by one or several groups, that are either identical or different, selected from the group consisting of a halogen atom, —OH, oxo, nitro, —CHO, —OCOL$^1$R$^5$, —CO$_2$R$^{60}$, —NR$^9_2$, $C_1$-$C_6$ alkyl, $C_1$-$C_4$ alkoxy, $C_6$-$C_{12}$ aryl, $C_6$-$C_{12}$ aryloxy, $C_6$-$C_{12}$ aryl $C_1$-$C_6$ alkyl, $C_1$-$C_6$ hydroxyalkyl, and $C_1$-$C_6$alkyl $C_6$-$C_{12}$ aryl; and R$^5$ is selected from the group consisting of H, a halogen atom, —OH, —CHO, epoxy, —SR$^8$, cyano, nitro, isocyanate, $C_1$-$C_{20}$ alkyl, $C_1$-$C_4$ alkoxy, $C_2$-$C_{20}$ alkenyl, $C_2$-$C_{20}$ alkynyl, heterocycloalkyl, —CHO$_2$R$^8$, and —NR$^9_2$;

wherein the reaction involves two successive steps comprising:

an epoxidation of the compound of formula (II), generating an epoxide ring, in the presence of molecular or atmospheric oxygen and of at least one aldehyde of formula (III) and optionally in the presence of at least one catalyst, and an opening of the epoxide ring, optionally in the presence of at least one catalyst.

2. The process according to claim 1, wherein the multifunctional compound is a compound having formula (Ia) or (Ib), a stereoisomer, a mixture thereof, an oligomer and/or a polymer thereof:

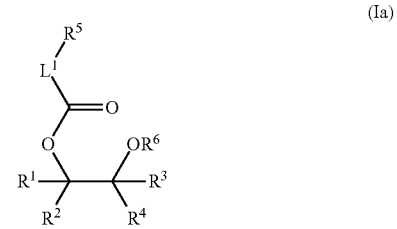

(Ia)

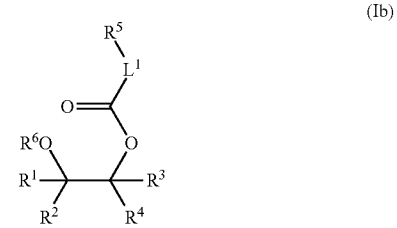

(Ib)

wherein:

R$^1$ is H or is selected from the group consisting of $C_1$-$C_{20}$ alkyl, $C_2$-$C_{20}$ alkenyl, and $C_6$-$C_{12}$ aryl, with each group optionally being substituted by one or several groups, that are either identical or different, selected from the group consisting of a halogen atom, —OH, —CHO, oxo, cyano, —NR$^9_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$;

R$^2$ is H, cyano, or a halogen atom, or is selected from the group consisting of $C_1$-$C_{20}$ alkyl, $C_2$-$C_{20}$ alkenyl, $C_6$-$C_{12}$ aryl, and $C_6$-$C_{12}$ aryl $C_1$-$C_6$ alkyl, with each group optionally being substituted by one or several groups, that are either identical or different, selected from the group consisting of a halogen atom, —OH, —CHO, oxo, cyano, —NR$^9_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CO$_2$R$^{60}$;

R$^3$ is selected from the group consisting of epoxy, —OCOR$^8$, —CO$_2$R$^8$, $C_1$-$C_{20}$ alkyl, $C_2$-$C_{20}$ alkenyl, $C_6$-$C_{12}$ aryl, and $C_6$-$C_{12}$ aryl $C_1$-$C_6$ alkyl, with each group optionally being substituted by one or several groups, that are either identical or different, selected from the group consisting of a halogen atom, —OH, —CHO, oxo, cyano, —NR$^9_2$, epoxy, $C_1$-$C_4$ alkoxy, $C_1$-$C_6$ alkyl, $C_6$-$C_{12}$ aryl, —OCOL$^1$R$^5$, —OCOR$^8$, and —CHO$_2$R$^{60}$;

R⁴ is H, cyano, a halogen atom, or is selected from the group consisting of $C_1$-$C_{20}$ alkyl, $C_2$-$C_{20}$ alkenyl, and $C_6$-$C_{12}$ aryl, with each group optionally being substituted by one or several groups, that are either identical or different, selected from the group consisting of a halogen atom, —OH, —CHO, oxo, cyano, —NR⁹₂, epoxy, $C_1$-$C_4$ alkoxy, $C_1$-$C_6$ alkyl, $C_6$-$C_{12}$ aryl, —OCOL¹R⁵, —OCOR⁸, and —CHO₂R⁶⁰;

or R¹ and R³ may, with the carbons to which they are bound, form a group selected from the group consisting of a $_{C5}$-$C_{12}$ cycloalkyl, and a $_{C5}$-$C_{12}$ cycloalkenyl, with each group optionally being substituted by one or several groups, that are either identical or different, selected from the group consisting of a halogen atom,—OH, oxo, cyano, epoxy, —OCOL¹R⁵, —OCOR⁸, —CO₂R⁶⁰, $C_1$-$C_6$ alkyl, $C_1$-$C_6$ hydroxyalkyl, and $C_2$-$C_6$ alkenyl;

R⁵ is selected from the group consisting of H, a halogen atom, —OH, —CHO, epoxy,—SR⁸, cyano, nitro, isocyanate, $C_1$-$C_{20}$ alkyl, $C_1$-$C_4$ alkoxy, $C_2$-$C_{20}$ alkenyl, $C_2$-$C_{20}$ alkynyl, heterocycloalkyl, —CO₂R⁸, and —NR⁹₂;

R⁶ is H or —CHO-L¹-R⁵;

L¹ is a single covalent bond, or is selected from the group consisting of $C_1$-$C_{20}$ alkylene, $C_3$-$C_{12}$ cycloalkylene, $C_2$-$C_{12}$ alkenylene, $C_5$-$C_{12}$ cycloalkenylene, $C_6$-$C_{12}$ arylene, heteroarylene, and heterocycloalkylene, with each group optionally being substituted by one or several groups, that are either identical or different, selected from the group consisting of a halogen atom, —OH, oxo, nitro, —CHO, —OCOL¹R⁵, —CHO₂R⁶⁰, —NR⁹₂, $C_1$-$C_6$ alkyl, $C_1$-$C_4$ alkoxy, $C_6$-$C_{12}$ aryl, $C_6$-$C_{12}$ aryloxy, $C_6$-$C_{12}$ aryl $C_1$-$C_6$ alkyl, $C_1$-$C_6$ hydroxyalkyl, and $C_1$-$C_6$alkyl $C_6$-$C_{12}$ aryl.

3. The process according to claim 1, wherein the reaction takes place in the presence of a catalyst.

4. The process according to claim 3, wherein the catalyst is selected from the group consisting of catalysts with a basis of ruthenium, palladium, platinum, cobalt, manganese, nickel, copper, zinc, iron, and activated carbons.

5. The process according to claim 3, wherein the catalyst is a supported ruthenium-based catalyst.

6. The process according to claim 1, wherein the compound of formula (II) is a $C_3$-$C_{20}$ alkene, or a $C_5$-$C_{12}$ cycloalkene, with each alkene or cycloalkene being optionally substituted by one or several identical or different groups selected from the group consisting of a halogen atom, —CHO, —OH, cyano, oxo, epoxy, —OCOR⁸, $C_1$-$C_6$ alkyl, $C_2$-$C_6$ alkenyl, $C_6$-$C_{12}$ aryl, —OCOL²R⁵⁰, and—CHO₂R⁶⁰; with each alkyl, alkenyl or aryl being optionally substituted by one or several groups, that are identical or different, selected from the group consisting of a halogen atom, oxo, —CHO, —OH, $C_1$-$C_6$ alkyl, $C_6$-$C_{12}$ aryl, —OCOL²R⁵⁰, —OCOR⁸, and —CO₂R⁶⁰.

7. The process according to claim 1, wherein the aldehyde of formula (III) is selected from the group consisting of formaldehyde, acetaldehyde, propanal, butyraldehyde, valeraldehyde, hexanal, heptanaldehyde, octanal, nonanaldehyde, decanal, undecanaldehyde, laurinaldehyde, tridecanaldehyde, isobutyraldehyde, isovaleraldehyde, 2-methylbutyraldehyde, pivalaldehyde, 2-ethylbutaraldehyde, 2ethylhexanaldehyde, isodecanaldehyde, acroleine, crotonaldehyde, trans-2-hexen-1-al, trans,trans-2,4-hexadien-1-al, cis-4-heptenal, trans-2-nonen-1-al, cis-4-decenal, citronellal, hydroxycitronellal, 1-cyclohexene-1-carboxaldehyde, 3-cyclohexene-1-carboxaldehyde, benzaldehyde, 3- hydroxybenzaldehyde, 4-hydroxybenzaldehyde, 4-methyl-2-phenyl-2-pentenal, aldehyde para-tertiarybutyl-alpha-methyl hydrocinnamic, amylcinnamic aldehyde, glyoxal, glutaraldehyde, furfuraldehyde, 3-(methylthio)propionaldehyde, 2-ethylacroleine, 3-methylcrotonaldehyde, 2-methyl-2-butenal, methyl 4-oxobutanoate, cinnamaldehyde, 3-dimethylaminoacroleine, cyclopentanecarboxaldehyde, 2,3,4,5,6-pentafluorobenzaldehyde, 4-bromo-2,6-difluorobenzaldehyde, 3,5-dibromobenzaldehyde, 3,5-dibromo-4-hydroxybenzaldehyde, 2,6-dinitrobenzaldehyde, 4-chlorobenzaldehyde, 2-chloro-4- hydroxybenzaldehyde, 4-fluorobenzaldehyde, 5-fluorosalicylaldehyde, 4-nitrobenzaldehyde, 4-hydroxy-3-nitrobenzaldehyde, 3,5-dihydroxybenzaldehyde, 2,4,6-trihydroxybenzaldehyde, 2-aminobenzaldehyde, 2,4-heptadienal, 2,2-dimethyl-4-pentenal, 2-cyanobenzaldehyde, isophtalaldehyde, terephthalaldehyde, 4-formylbenzoic acid, 5-formylsalicylic acid, o,m,p-tolualdehyde, phenylacetaldehyde, 2,4-dihydroxy-6-methylbenzaldehyde, 3-vinylbenzaldehyde, hydrocinnamaldehyde, 4-hydroxy-3,5-dimethylbenzaldehyde, mesitaldehyde, 2,4,6-trimethoxybenzaldehyde, 1-naphtaldehyde, biphenyl-4-carboxaldehyde, 3- phenoxybenzaldehyde, 4-(4-formylphenoxy)benzaldehyde, diphenylacetaldehyde, 9-anthracenecarboxaldehyde, 9-phenanthrenecarboxaldehyde, 5-(hydroxymethyl)furfural, and tris(4-formylphenyl)amine.

8. The process according to claim 1, wherein the epoxidation step is carried out at a temperature of between 0 and 200° C.

9. The process according to claim 8, wherein the epoxide opening step is carried out at a temperature of between 0 and 300° C.

10. The process according to claim 1, characterized in that it is carried out in the absence of any solvent.

* * * * *